United States Patent
Oda et al.

(10) Patent No.: US 9,453,103 B2
(45) Date of Patent: *Sep. 27, 2016

(54) METHOD FOR PRODUCING AROMATIC COMPOUND

(71) Applicant: Sumitomo Chemical Company, Limited, Tokyo (JP)

(72) Inventors: Seiji Oda, Osaka (JP); Takashi Kamikawa, Osaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 25 days.

This patent is subject to a terminal disclaimer.

(21) Appl. No.: 14/410,388

(22) PCT Filed: Jul. 5, 2013

(86) PCT No.: PCT/JP2013/069075
§ 371 (c)(1),
(2) Date: Dec. 22, 2014

(87) PCT Pub. No.: WO2014/007405
PCT Pub. Date: Jan. 9, 2014

(65) Prior Publication Data
US 2015/0322199 A1 Nov. 12, 2015

(30) Foreign Application Priority Data

Jul. 6, 2012 (JP) ................. 2012-152169

(51) Int. Cl.
*C08G 61/12* (2006.01)
*C08G 61/10* (2006.01)
*C07F 15/00* (2006.01)
(Continued)

(52) U.S. Cl.
CPC .......... *C08G 61/128* (2013.01); *C07C 209/68* (2013.01); *C07F 5/025* (2013.01); *C07F 9/5022* (2013.01); *C07F 9/5442* (2013.01); *C07F 15/006* (2013.01); *C08G 61/02* (2013.01); *C08G 61/10* (2013.01); *C08G 61/12* (2013.01); *C08G 61/123* (2013.01); *B01J 31/24* (2013.01); *C07C 2103/18* (2013.01); *C07C 2531/24* (2013.01); *C07F 9/5004* (2013.01); *C07F 9/5018* (2013.01); *C07F 9/5045* (2013.01); *C07F 9/5407* (2013.01); *C07F 15/0066* (2013.01); *C08G 2261/12* (2013.01); *C08G 2261/228* (2013.01); *C08G 2261/312* (2013.01); *C08G 2261/3142* (2013.01); *C08G 2261/3162* (2013.01); *C08G 2261/411* (2013.01)

(58) Field of Classification Search
CPC .... C08G 61/128; C08G 61/123; C08G 1/02; C08G 1/10; C08G 1/12; C07F 5/025; C07F 15/006; C07F 9/5442; C07F 9/5022; C07C 209/68

USPC ................. 528/8; 556/22; 568/9, 13, 17
See application file for complete search history.

(56) References Cited

U.S. PATENT DOCUMENTS 5,514,805 A  5/1996 Broger et al.
9,238,665 B2 * 1/2016 Oda .................. C08G 61/12
(Continued)

FOREIGN PATENT DOCUMENTS

CN 101952298 A 1/2011
EP 1997844 A1 12/2008
(Continued)

OTHER PUBLICATIONS

International Search Report issued Aug. 6, 2013 in International Application No. PCT/JP2013/069075.
(Continued)

*Primary Examiner* — Porfirio Nazario Gonzalez
(74) *Attorney, Agent, or Firm* — Panitch Schwarze Belisario & Nadel LLP

(57) ABSTRACT

A method is provided for producing an aromatic compound, including a step of mixing a compound represented by formula (A) and a compound represented by formula (B):

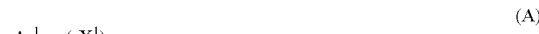

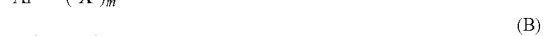

in the presence of at least one phosphine compound selected from the group consisting of a phosphine represented by formula (C) and a phosphonium salt represented by formula (D):

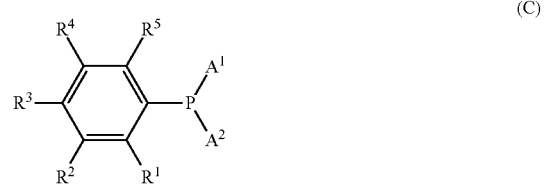

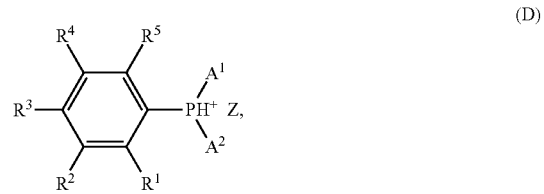

a base, a palladium compound, and an aprotic organic solvent.

9 Claims, No Drawings

(51) Int. Cl.
*C07F 9/50* (2006.01)
*C08G 61/02* (2006.01)
*C07C 209/68* (2006.01)
*C07F 5/02* (2006.01)
*B01J 31/24* (2006.01)
*C07F 9/54* (2006.01)

(56) References Cited

U.S. PATENT DOCUMENTS

| | | | |
|---|---|---|---|
| 2009/0048413 | A1 | 2/2009 | Oda et al. |
| 2010/0041898 | A1 | 2/2010 | Busacca et al. |
| 2010/0144999 | A1 | 6/2010 | Yokozawa et al. |
| 2010/0176376 | A1 | 7/2010 | Suzuki et al. |
| 2011/0105796 | A1 | 5/2011 | Moradi et al. |
| 2012/0116036 | A1 | 5/2012 | Nozaki et al. |

FOREIGN PATENT DOCUMENTS

| | | | |
|---|---|---|---|
| JP | 2007119709 | A | 5/2007 |
| JP | 2007277534 | A | 10/2007 |
| JP | 2008045110 | A | 2/2008 |
| WO | 0064841 | A2 | 11/2000 |
| WO | 2004052939 | A2 | 6/2004 |
| WO | 2007101820 | A1 | 9/2007 |
| WO | 2009076622 | A2 | 6/2009 |
| WO | 2012133874 | A1 | 10/2012 |

OTHER PUBLICATIONS

Lü et al., "Application of Dicyclohexyl-(S)-trimethoxyphenyl Phosphine-HBF4 Salt for the Highly Selective Suzuki Coupling of the C-Cl Bond in b-Chlorobutenolides Over the More Reactive Allylic C-O Bond," Chemistry—A European Journal, vol. 16, pp. 6434-6437 (2010).

Grabulosa et al., "Palladium complexes of bulky ortho-trifluoromethylphenyl-substituted phosphines: Unusually regioselective catalysts for the hydroxycarbonylation and alkoxycarbonylation of alkenes," Journal of Molecular Catalysis A: Chemical, vol. 330, pp. 18-25 (2010).

Partial Supplementary Search Report issued Nov. 23, 2015 in EP Application No. 13812454.0.

Guram et al., "New Catalysts for Suzuki-Miyaura Coupling Reactions of Heteroatom-Substituted Heteroaryl Chlorides," Journal of Organic Chemistry, vol. 72, pp. 5104-5112 (2007).

Fu et al., "Air-Stable Trialkylphosphonium Salts: Simple, Practical, and Versatile Replacements for Air-Sensitive Trialkylphosphines. Applications in Stoichiometric and Catalytic Processes," Organic Letters, vol. 3, No. 26, pp. 1295-4298 (2001).

Extended Search Report issued Apr. 13, 2016 in Int'l Application No. PCT/JP2013/069075.

Goryunov et al., "Di- and Trifluorobenzenes in Reactions with Me2EM (E=P, N; M=SiMe3t SnMe3t Li) Reagents: Evidence for a Concerted Mechanism of Aromatic Nucleophilic Substitution", European Journal of Organic Chemistry, vol. 2010, No. 6, pp. 1111-1123 (Feb. 12, 2010).

Goryunov et al., "Compounds R1R2EMMe3 (E=P, As; M=Si. Sn)—Convenient and Versatile Reagents for the Syntheses of Tertiary (Fluoroaryl) Phosphanes and -Arsanes", Collection of Czechoslovak Chemical Commun., vol. 73, No. 12, pp. 1612-1622 (Jan. 1, 2008).

Marchenko et al., "Effect of Lewis Acidity on the Synthesis of RuHCl (CO) (phosphine) 2 : Subtle Influence of Steric and Electronic Effects among P i Pr 3, Pi Pr 2 (3,5-(CF 3) 2 C 6 H 3 ), and P i Pr 2 Me", Inorganic Chemistry, vol. 40, No. 25, pp. 6444-6450 (Dec. 1, 2001).

Extended Search Report issued Dec. 9, 2015 in EP Appliction No. 13813597.5.

Suzuki, "Recent Advances in the Cross-Coupling Reactions of Organoboron Derivatives with Organic Electrophiles, 1995-1998", Journ. of Organo. Chemistry, vol. 576, pp. 147-168 (1999).

Office Action issued Jan. 29, 2016 in CN Application No. 201380044332.3.

Garcia-Fortanet et al., "Asymmetric Palladium-Catalyzed Intramolecular a-Arylation of Aldehydes", Angew. Chem., vol. 120, pp. 8228-8231 (2008).

Murata, et al., "A General and Efficient Method for the Palladium-Catalyzed Cross-Coupling of Thiols and Secondary Phosphines", Tetrahedron, vol. 60, pp. 7397-7403 (2004).

Office Action issued Jan. 22, 2016 in CN Application No. 201380044368.1.

\* cited by examiner

METHOD FOR PRODUCING AROMATIC COMPOUND

CROSS-REFERENCE TO RELATED APPLICATION

This application is a Section 371 of International Application No. PCT/JP2013/069075, filed July 5, 2013, which was published in the Japanese language on January 9, 2014, under International Publication No. WO 2014/007405 A9, and the disclosure of which is incorporated herein by reference.

TECHNICAL FIELD

The present invention relates to a production method of an aromatic compound.

BACKGROUND ART

An aromatic compound having a structure in which two or more aromatic rings are π-conjugated is useful, for example, for an organic electronics material. As a method for producing the aromatic compound, a method of production by the Suzuki coupling reaction is known.

Specifically, Patent document 1 describes a method of polymerizing bis(4-bromophenyl)[4-(2-butyl)phenyl]amine and a boronate formed of 9,9-di-n-octylfluorene-2,7-diboronic acid and pinacol (tetramethyl ethylene glycol) in the presence of palladium acetate, tris(2-methoxyphenyl)phosphine, a tetraethylammonium hydroxide aqueous solution and toluene, to produce the corresponding aromatic compound.

PRIOR ART DOCUMENT

Patent Document

[Patent document 1] JP-A No. 2007-126652

SUMMARY OF THE INVENTION

Problem to be Solved by the Invention

The present invention has an object of providing a novel method of producing an aromatic compound.

Means for Solving the Problem

Under such conditions, the present inventors have intensively studied a method for producing an aromatic compound, resultantly leading to the present invention.

That is, the present invention provides

[1] A method of producing an aromatic compound, comprising a step of mixing a compound represented by the formula (A):

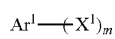

(wherein, $X^1$ represents a group represented by the formula (1), (2), (3), (4), (5) or (6):

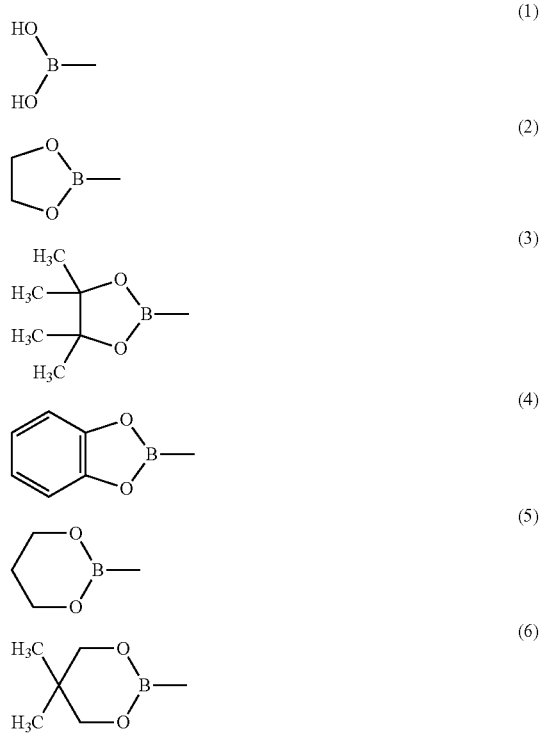

$Ar^1$ represents a monovalent or divalent aromatic hydrocarbon group having a number of carbon atoms of 6 to 36, and m represents 1 or 2. A carbon atom contained in the aromatic hydrocarbon group may be substituted with a hetero atom or a carbonyl group, and a hydrogen atom contained in the aromatic hydrocarbon group may be substituted with a fluorine atom, an alkyl group, a cycloalkyl group, an alkoxy group, a cycloalkoxy group, an alkylthio group, a cycloalkylthio group, an aryl group, an aryloxy group, an arylthio group, an arylalkyl group, an arylcycloalkyl group, an arylalkenyl group, an arylalkynyl group, a heterocyclic group which may have a substituent, an amino group which may have a substituent, a silyl group which may have a substituent, an acyl group, a group having a carbon atom-nitrogen atom double bond as a partial structure, an acid imide group, an alkoxycarbonyl group, a cycloalkoxycarbonyl group, an aryloxycarbonyl group, a carboxyl group, a cyano group or a nitro group.)

and a compound represented by the formula (B):

(wherein, $X^2$ represents a chlorine atom, a bromine atom, an iodine atom, an alkylsulfonyloxy group, a fluorine-substituted alkylsulfonyloxy group or an arylsulfonyloxy group, $Ar^2$ represents a monovalent or divalent aromatic hydrocarbon group having a number of carbon atoms of 6 to 36, and n represents 1 or 2. A carbon atom contained in the aromatic hydrocarbon group may be substituted with a hetero atom or a carbonyl group, and a hydrogen atom contained in the aromatic hydrocarbon group may be substituted with a fluorine atom, an alkyl group, a cycloalkyl group, an alkoxy group, a cycloalkoxy group, an alkylthio group, a cycloalkylthio group, an aryl group, an aryloxy group, an arylthio group, an arylalkyl group, an arylcycloalkyl group, an arylalkenyl group, an arylalkynyl group, a heterocyclic group which may have a substituent, an amino group which may have a substituent, a silyl group which may have a substituent, an acyl group, a group having a carbon atom-nitrogen atom double bond as a partial structure, an acid imide group, an alkoxycarbonyl group, a cycloalkoxycarbonyl group, an aryloxycarbonyl group, a carboxyl group, a cyano group or a nitro group.)

in the presence of at least one phosphine compound selected from the group consisting of a phosphine represented by the formula (C):

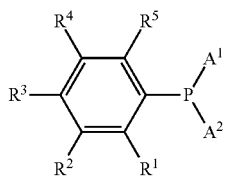

(C)

(wherein, $A^1$ and $A^2$ represent each independently an alkyl group having a number of carbon atoms of 1 to 20 or a saturated alicyclic hydrocarbon group having a number of carbon atoms of 6 to 20. $R^1$ and $R^5$ represent each independently a hydrogen atom, an alkoxy group having a number of carbon atoms of 1 to 20 or a cycloalkoxy group having a number of carbon atoms of 3 to 20, and $R^2$, $R^3$ and $R^4$ represent each independently a hydrogen atom, a fluorine atom, an alkyl group having a number of carbon atoms of 1 to 20, a cycloalkyl group having a number of carbon atoms of 3 to 20, an alkoxy group having a number of carbon atoms of 1 to 20, a cycloalkoxy group having a number of carbon atoms of 3 to 20, a fluoroalkoxy group having a number of carbon atoms of 1 to 20, a fluorocycloalkoxy group having a number of carbon atoms of 3 to 30 or an aryl group having a number of carbon atoms of 6 to 20. Here, all of $R^1$ to $R^5$ do not simultaneously represent a hydrogen atom. Further, $R^2$ and $R^3$ may be linked to form a ring together with a carbon atom to which they are linked and $R^3$ and $R^4$ may be linked to form a ring together with a carbon atom to which they are linked.) and a phosphonium salt represented by the formula (D):

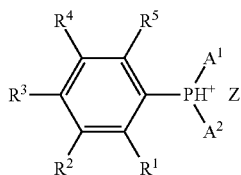

(D)

(wherein, $A^1$, $A^2$, $R^1$ to $R^5$ represent the same meaning as described above, and Z represents an anion.), a base, a palladium compound and an aprotic organic solvent;

[2] The production method of an aromatic compound according to [1], wherein the phosphine compound is at least one selected from the group consisting of a phosphine represented by the formula (E):

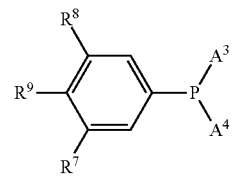

(E)

(wherein, $A^3$ and $A^4$ represent each independently an alkyl group having a number of carbon atoms of 1 to 20 or a saturated alicyclic hydrocarbon group having a number of carbon atoms of 6 to 20. $R^5$ and $R^8$ represent each independently a fluorine atom, an alkyl group having a number of carbon atoms of 1 to 20, a cycloalkyl group having a number of carbon atoms of 3 to 20, an alkoxy group having a number of carbon atoms of 1 to 20, a cycloalkoxy group having a number of carbon atoms of 3 to 20, a fluoroalkoxy group having a number of carbon atoms of 1 to 20 or an aryl group having a number of carbon atoms of 6 to 20, and $R^9$ represents a hydrogen atom, a fluorine atom, an alkyl group having a number of carbon atoms of 1 to 20, a cycloalkyl group having a number of carbon atoms of 3 to 20, an alkoxy group having a number of carbon atoms of 1 to 20, a cycloalkoxy group having a number of carbon atoms of 3 to 20, a fluoroalkoxy group having a number of carbon atoms of 1 to 20 or an aryl group having a number of carbon atoms of 6 to 20.)

and a phosphonium salt represented by the formula (F):

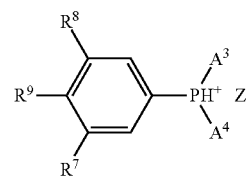

(F)

(wherein, $A^3$, $A^4$, $R^9$, $R^8$, $R^9$ and Z represent the same meaning as described above.);

[3] The production method of an aromatic compound according to [2], wherein $R^7$ and $R^8$ represent each independently a fluorine atom, an alkyl group having a number of carbon atoms of 1 to 6, an alkoxy group having a number of carbon atoms of 1 to 6, a fluoroalkoxy group having a number of carbon atoms of 1 to 6 or an aryl group having a number of carbon atoms of 6 to 20;

[4] The production method of an aromatic compound according to [2] or [3], wherein $R^9$ is a hydrogen atom;

[5] The production method of an aromatic compound according to anyone of [1] to [4], wherein the aprotic organic solvent is at least one selected from the group consisting of ether solvents, aromatic hydrocarbon solvents and aliphatic hydrocarbon solvents;

[6] The production method of an aromatic compound according to any one of [1] to [5], wherein the palladium compound is a palladium (0) complex or a palladium(II) complex;

[7] A phosphine represented by the formula (E):

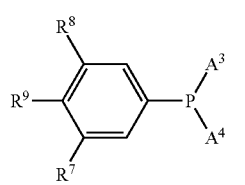
(E)

(wherein, $A^3$ and $A^4$ represent each independently an alkyl group having a number of carbon atoms of 1 to 20 or a saturated alicyclic hydrocarbon group having a number of carbon atoms of 6 to 20. $R^7$ and $R^8$ represent each independently a fluorine atom, an alkyl group having a number of carbon atoms of 1 to 20, a cycloalkyl group having a number of carbon atoms of 3 to 20, an alkoxy group having a number of carbon atoms of 1 to 20, a cycloalkoxy group having a number of carbon atoms of 3 to 20, a fluoroalkoxy group having a number of carbon atoms of 1 to 20 or an aryl group having a number of carbon atoms of 6 to 20, and $R^9$ represents a hydrogen atom, a fluorine atom, an alkyl group having a number of carbon atoms of 1 to 20, a cycloalkyl group having a number of carbon atoms of 3 to 20, an alkoxy group having a number of carbon atoms of 1 to 20, a cycloalkoxy group having a number of carbon atoms of 3 to 20, a fluoroalkoxy group having a number of carbon atoms of 1 to 20 or an aryl group having a number of carbon atoms of 6 to 20.);

[8] The phosphine according to [7], wherein $R^9$ and $R^8$ are each independently a fluorine atom, an alkyl group having a number of carbon atoms of 1 to 6, an alkoxy group having a number of carbon atoms of 1 to 6, a fluoroalkoxy group having a number of carbon atoms of 1 to 6 or an aryl group having a number of carbon atoms of 6 to 20;

[9] The phosphine according to [7] or [8], wherein $R^9$ is a hydrogen atom;

[10] A phosphonium salt represented by the formula (F):

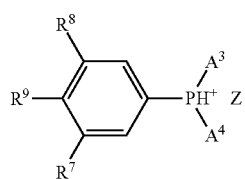
(F)

(wherein, $A^3$ and $A^4$ represent each independently an alkyl group having a number of carbon atoms of 1 to 20 or a saturated alicyclic hydrocarbon group having a number of carbon atoms of 6 to 20. $R^9$ and $R^8$ represent each independently a fluorine atom, an alkyl group having a number of carbon atoms of 1 to 20, a cycloalkyl group having a number of carbon atoms of 3 to 20, an alkoxy group having a number of carbon atoms of 1 to 20, a cycloalkoxy group having a number of carbon atoms of 3 to 20, a fluoroalkoxy group having a number of carbon atoms of 1 to 20 or an aryl group having a number of carbon atoms of 6 to 20, and $R^9$ represents a hydrogen atom, a fluorine atom, an alkyl group having a number of carbon atoms of 1 to 20, a cycloalkyl group having a number of carbon atoms of 3 to 20, an alkoxy group having a number of carbon atoms of 1 to 20, a cycloalkoxy group having a number of carbon atoms of 3 to 20, a fluoroalkoxy group having a number of carbon atoms of 1 to 20 or an aryl group having a number of carbon atoms of 6 to 20. Z represents an anion.);

[11] The phosphonium salt according to [10], wherein $R^7$ and $R^8$ are each independently a fluorine atom, an alkyl group having a number of carbon atoms of 1 to 6, an alkoxy group having a number of carbon atoms of 1 to 6, a fluoroalkoxy group having a number of carbon atoms of 1 to 6 or an aryl group having a number of carbon atoms of 6 to 20;

[12] A transition metal complex obtained by contacting the phosphine according to any one of [7] to [9] and a group X transition metal compound;

and the like.

Effect of the Invention

According to the production method of the present invention, an aromatic compound can be produced.

MODES FOR CARRYING OUT THE INVENTION

<Compound Represented by the Formula (A) and Compound Represented by the Formula (B)>

The compound represented by the formula (A) used in the production method of the present invention includes a compound represented by the formula (A-1):

(hereinafter, referred to as a compound (A-1) in some cases) and a compound represented by the formula (A-2):

(hereinafter, referred to as a compound (A-2) in some cases), and the compound represented by the formula (B) includes a compound represented by the formula (B-1):

(hereinafter, referred to as a compound (B-1) in some cases) and a compound represented by the formula (B-2):

(hereinafter, referred to as a compound (B-2) in some cases).

$Ar^1$ and $Ar^2$ represent each independently a monovalent or divalent aromatic hydrocarbon group having a number of carbon atoms of 6 to 36. The monovalent or divalent aromatic hydrocarbon group includes a monovalent or divalent monocyclic aromatic hydrocarbon group, a monovalent or divalent condensed aromatic hydrocarbon group, and a monovalent or divalent group formed by linking two or more monocyclic aromatic hydrocarbon groups via a single bond, a hetero atom (an oxygen atom, a nitrogen atom, a sulfur atom or the like) or a carbonyl group (—CO—). Specific examples thereof include monovalent monocyclic aromatic hydrocarbon groups such as a phenyl group and the like, divalent monocyclic aromatic hydrocarbon groups such as a phenylene group and the like, monovalent condensed aromatic hydrocarbon groups such as a naphthyl group, an anthracenyl group, a fluorenyl group and the like, divalent condensed aromatic hydrocarbon groups such as a naphthalenediyl group, an anthracenediyl group, a fluorenediyl group and the like, monovalent groups formed by linking two or more monocyclic aromatic hydrocarbon groups via a single bond, a hetero atom (an oxygen atom, a nitrogen atom, a sulfur atom or the like) or carbonyl group such as a biphenyl group and the like, and divalent groups formed by linking two or more monocyclic aromatic hydrocarbon groups via a single bond, a hetero atom (an oxygen atom, a nitrogen atom, a sulfur atom or the like) or a carbonyl group such as a biphenylene group and the like. A carbon atom contained in the aromatic hydrocarbon group may be substituted with a hetero atom such as an oxygen atom, a nitrogen atom, a sulfur atom and the like or a carbonyl group.

A hydrogen atom contained in the above-described monovalent or divalent aromatic hydrocarbon group having a number of carbon atoms of 6 to 36 may be substituted with a fluorine atom, an alkyl group, a cycloalkyl group, an alkoxy group, a cycloalkoxy group, an alkylthio group, a cycloalkylthio group, an aryl group, an aryloxy group, an arylthio group, an arylalkyl group, an arylcycloalkyl group, an arylalkenyl group, an arylalkynyl group, a heterocyclic group which may have a substituent, an amino group which may have a substituent, a silyl group which may have a substituent, an acyl group, a group having a carbon atom-nitrogen atom double bond as a partial structure, an acid imide group, an alkoxycarbonyl group, a cycloalkoxycarbonyl group, an aryloxycarbonyl group, a carboxyl group, a cyano group or a nitro group. A hydrogen atom contained in these substituents may be substituted with a fluorine atom, an alkoxy group having a number of carbon atoms of 1 to 20, an aryl group having a number of carbon atoms of 6 to 20, an aryloxy group having a number of carbon atoms of 6 to 20, an acyl group having a number of carbon atoms of 2 to 20 or a cyano group.

"Alkyl group" includes an alkyl group having a number of carbon atoms of 1 to 20, and may be linear or branched. Specific examples thereof include a methyl group, an ethyl group, a n-propyl group, an isopropyl group, a n-butyl group, an isobutyl group, a sec-butyl group, a tert-butyl group, a n-pentyl group, a 2,2-dimethylpropyl group, a n-hexyl group, a n-heptyl group, a 2-methylpentyl group, a n-octyl group, a 2-ethylhexyl group, a n-nonyl group, a n-decyl group, a n-undecyl group, a n-dodecyl group, a n-tridecyl group, a n-tetradecyl group, a n-pentadecyl group, a n-hexadecyl group, a n-heptadecyl group, a n-octadecyl group, a n-nonadecyl group and a n-icosyl group.

"Cycloalkyl group" includes a cycloalkyl group having a number of carbon atoms of 3 to 20, and specifically includes a cyclopropyl group, a cyclopentyl group, a cyclohexyl group, a cycloheptyl group and a cyclooctyl group.

"Alkoxy group" includes an alkoxy group having a number of carbon atoms of 1 to 20, and may be linear or branched. Specific examples thereof include a methoxy group, an ethoxy group, a n-propoxy group, an isopropoxy group, a n-butoxy group, a sec-butoxy group, a tert-butoxy group, a n-pentyloxy group, a 2,2-dimethylpropoxy group, a n-hexyloxy group, a n-heptyloxy group, a n-octyloxy group, a n-nonyloxy group, a n-decyloxy group, a n-undecyloxy group, a n-dodecyloxy group, a n-tridecyloxy group, a n-tetradecyloxy group, a n-pentadecyloxy group, a n-hexadecyloxy group, a n-heptadecyloxy group, a n-octadecyloxy group, a n-nonadecyloxy group and a n-eicosyl oxy group.

"Cycloalkoxy group" includes a cycloalkoxy group having a number of carbon atoms of 3 to 20, and specifically includes a cyclopropoxy group, a cyclopentyloxy group, a cyclohexyloxy group, a cycloheptyloxy group and a cyclooctyloxy group.

"Alkylthio group" includes an alkylthio group having a number of carbon atoms of 1 to 20, and may be linear or branched. Specific examples thereof include a methylthio group, an ethylthio group, a n-propylthio group, an isopropylthio group, a n-butylthio group, an isobutylthio group, a sec-butylthio group, a tert-butylthio group, a n-pentylthio group, a n-hexylthio group, a n-heptylthio group, a n-octylthio group, a 2-ethylhexylthio group, a n-nonylthio group, a n-decylthio group, a 3,7-dimethyloctylthio group and a n-dodecylthio group.

"Cycloalkylthio group" includes a cycloalkylthio group having a number of carbon atoms of 3 to 20, and specifically includes a cyclopropylthio group, a cyclopentylthio group, a cyclohexylthio group, a cycloheptylthio group and a cyclooctylthio group.

"Aryl group" includes an aryl group having a number of carbon atoms of 6 to 20, and the like, and specifically includes a phenyl group, a 4-methylphenyl group, a 2-methylphenyl group, a 1-naphthyl group, a 2-naphthyl group, a 3-phenanthryl group, a 2-anthryl group and the like.

"Aryloxy group" includes a group formed by linking an oxygen atom to the above-described aryl group having a number of carbon atoms of 6 to 20. Specific examples thereof include a phenoxy group, a naphthyloxy group, a phenanthryloxy group and an anthryloxy group and the like.

"Arylthio group" includes a group formed by linking a sulfur atom to the above-described aryl group having a number of carbon atoms of 6 to 20. Specific examples thereof include a phenylthio group and a naphthylthio group.

"Arylalkyl group" includes a group obtained by substituting a hydrogen atom of the above-described alkyl group having a number of carbon atoms of 1 to 20 with an aryl group having a number of carbon atoms of 6 to 20, and specifically includes a phenylmethyl group, a naphthylmethyl group and the like.

"Arylcycloalkyl group" includes a phenylcyclohexyl group, a naphthylcyclohexyl group, a phenylcyclopentyl group and the like.

"Arylalkenyl group" includes a phenylalkenyl group and a naphthylalkenyl group. "Alkenyl group" includes an alkenyl group having a number of carbon atoms of 2 to 8 such as a vinyl group, a 1-propenyl group, a 2-propenyl group, a 1-butenyl group, a 2-butenyl group, a 1-pentenyl group, a 2-pentenyl group, a 1-hexenyl group, a 2-hexenyl group, a 1-octenyl group and the like.

"Arylalkynyl group" includes a phenylalkynyl group and a naphthylalkynyl group. "Alkynyl group" includes an alkynyl group having a number of carbon atoms of 2 to 8 such as an ethynyl group, a 1-propynyl group, a 2-propynyl group, a 1-butynyl group, a 2-butynyl group, a 1-pentynyl group, a 2-pentynyl group, a 1-hexynyl group, a 2-hexynyl group, a 1-octynyl group and the like.

"Heterocyclic group which may have a substituent" denotes a group obtained by converting one hydrogen atom in a heterocyclic compound which may have a substituent into a connecting bond. The heterocyclic group includes a thienyl group, an alkylthienyl group, a pyrrolyl group, a furyl group, a pyridyl group, an alkylpyridyl group, a pyridazinyl group, a pyrimidyl group, a pyrazinyl group, a triazinyl group, a pyrrolidinyl group, a piperidinyl group, a quinolyl group and an isoquinolyl group. The substituent carried on the above-described heterocyclic group includes an alkyl group, and specifically, the above-described alkyl group having a number of carbon atoms of 1 to 20.

"Amino group which may have a substituent" denotes a group represented by —N(R')$_2$, and two R' represent each independently a hydrogen atom or a substituent. The substituent includes a hydrocarbon group having a number of carbon atoms of 1 to 20 such as an alkyl group, a cycloalkyl group, an aryl group and the like, and a heterocyclic group which may have a substituent. Preferably, it is an amino group having a substituent, namely, an amino group in which at least one R' is a substituent. Specific examples of "amino group which may have a substituent" include a methylamino group, a dimethylamino group, an ethylamino group, a diethylamino group, a n-propylamino group, a di-n-propylamino group, an isopropylamino group, a diisopropylamino group, a n-butylamino group, an isobutylamino group, a sec-butylamino group, a tert-butylamino group, a n-pentylamino group, a n-hexylamino group, a n-heptylamino group, a n-octylamino group, a 2-ethylhexylamino group, a n-nonylamino group, a n-decylamino group, a 3,7-dimethyloctylamino group, a n-dodecylamino group, a cyclopentylamino group, a dicyclopentylamino group, a cyclohexylamino group, a dicyclohexylamino group, a bis(trifluoromethyl)amino group, a phenylamino group, a diphenylamino group, a naphthylamino group, a pyridylamino group, a pyridazinylamino group, a pyrimidinylamino group, a pyrazinylamino group and a triazinylamino group.

"Silyl group which may have a substituent" denotes a group represented by —Si(R')$_3$, and three R' represent each independently a hydrogen atom or a substituent. R' includes a hydrocarbon group having a number of carbon atoms of 1 to 20 such as an alkyl group, a cycloalkyl group, an aryl group and the like, and a heterocyclic group which may have a substituent. Preferably, it is a silyl group which has a substituent, namely, a silyl group in which at least one R' is a substituent. Specific examples of "silyl group which may have a substituent" include a trimethylsilyl group, a triethylsilyl group, a tri-n-propylsilyl group, a triisopropylsilyl group, a dimethylisopropylsilyl group, a diethylisopropylsilyl group, a tert-butylsilyldimethylsilyl group, a n-pentyldimethylsilyl group, a n-hexyldimethylsilyl group, a n-heptyldimethylsilyl group, a n-octyldimethylsilyl group, a 2-ethylhexyldimethylsilyl group, a n-nonyldimethylsilyl group, a n-decyldimethylsilyl group, a 3,7-dimethyloctyldimethylsilyl group, a n-dodecyldimethylsilyl group, a phenylalkylsilyl group, an alkoxyphenylalkylsilyl group, an alkylphenylalkylsilyl group, a naphthylalkylsilyl group, a phenylallyldimethylsilyl group, a triphenylsilyl group, a tri-p-xylylsilyl group, a tribenzylsilyl group, a diphenylmethylsilyl group, a tert-butyldiphenylsilyl group and a dimethylphenylsilyl group.

"Acyl group" includes an aliphatic acyl group such as an acetyl group, a propionyl group, a butylyl group, an isobutylyl group and the like and an aromatic acyl group such as a benzoyl group, a naphthoyl group and the like.

"Group having a carbon atom-nitrogen atom double bond as a partial structure" denotes a group formed by removing from an imine compound having a partial structure represented by at least one of the formula: H—N=C< and the formula: —N=CH— a hydrogen atom in the partial structure (hereinafter, referred to as imine residue in some cases), and includes those in which a ring is not formed based on the above-described "carbon atom-nitrogen atom double bond". "Imine compound" includes an aldimine, a ketimine and a compound obtained by substituting a hydrogen atom linked to a nitrogen atom in an aldimine with a substituent such as an alkyl group, an aryl group, an arylalkyl group, an arylalkenyl group, an arylalkynyl group and the like. The imine residue has a number of carbon atoms of usually 2 to 20, preferably 2 to 18, more preferably 2 to 16.

"Imine residue" includes a group represented by the formula: —CR''=N—R''' and a group represented by the formula: —N=C(R''')$_2$ (wherein, R'' represents a hydrogen atom, an alkyl group, an aryl group, an arylalkyl group, an arylalkenyl group or an arylalkynyl group, and a plurality of R''' represent each independently an alkyl group, a cycloalkyl group, an aryl group, an arylalkyl group, an arylcycloalkyl group, an arylalkenyl group or an arylalkynyl group. Here, when two R''' exist, two R''' are mutually linked to form a divalent group, specifically, an alkylene group having a number of carbon atoms of 2 to 18 such as an ethylene group, a trimethylene group, a tetramethylene group, a pentamethylene group, a hexamethylene group and the like.).

Specific examples of "imine residue" include groups shown below.

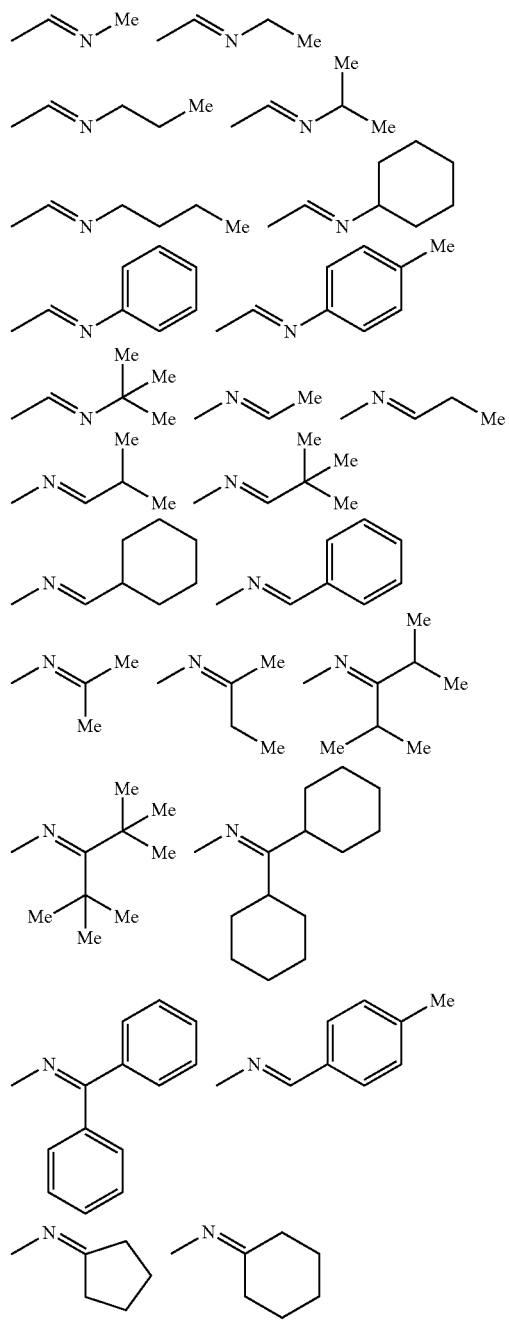

"Acid imide group" denotes a residue obtained by converting a hydrogen atom linking to a nitrogen atom contained in an acid imide into a connecting bond. The acid imide group has a number of carbon atoms of preferably 4 to 20, more preferably 4 to 18, further preferably 4 to 16. Specific examples of "acid imide group" include groups shown below.

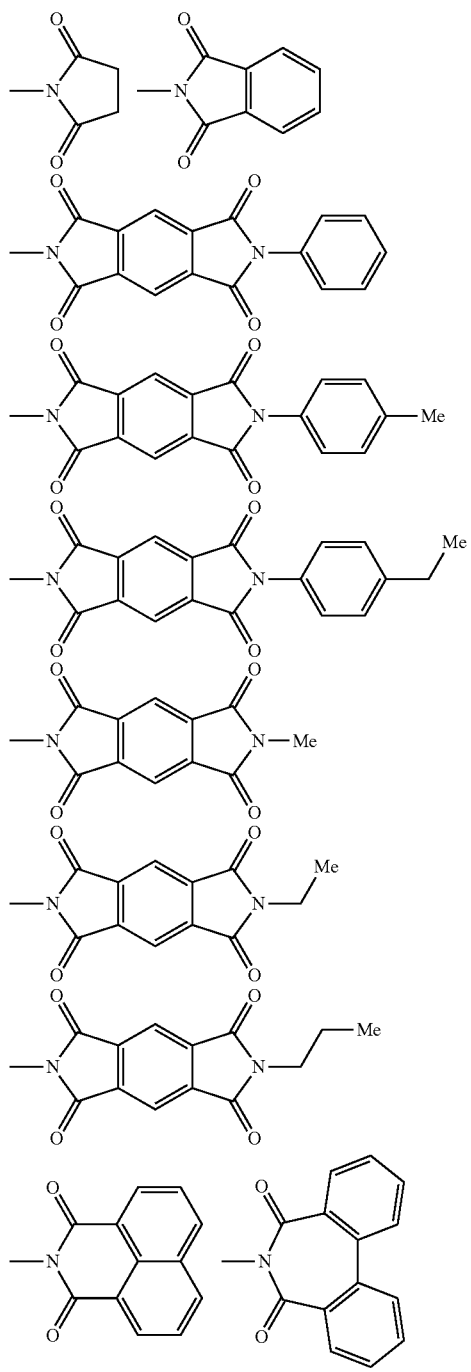

"Alkoxycarbonyl group" includes a group formed by linking a carbonyl group to the above-described alkoxy group. Specific examples thereof include a methoxycarbonyl group, an ethoxycarbonyl group, a n-propoxycarbonyl group, an isopropoxycarbonyl group, a n-butoxycarbonyl group, an isobutoxycarbonyl group, a sec-butoxycarbonyl group, a tert-butoxycarbonyl group, a n-pentyloxycarbonyl group, a n-hexyloxycarbonyl group, a n-heptyloxycarbonyl group, a n-octyloxycarbonyl group, a 2-ethylhexyloxycar- bonyl group, a n-nonyloxycarbonyl group, a n-decyloxycarbonyl group, a 3,7-dimethyloctyloxycarbonyl group, a n-dodecyloxycarbonyl group, a trifluoromethoxycarbonyl group, a pentafluoroethoxycarbonyl group, a perfluorobutoxycarbonyl group, a perfluorohexyloxycarbonyl group and a perfluorooctyloxycarbonyl group.

"Cycloalkoxycarbonyl group" includes a group formed by linking a carbonyl group to the above-described cycloalkoxy group. Specifically, a cyclohexyloxycarbonyl group is mentioned.

"Aryloxycarbonyl group" includes a group formed by linking a carbonyl group to the above-described aryloxy group. Specific examples thereof include a phenoxycarbonyl group, a naphthoxycarbonyl group and a pyridyloxycarbonyl group.

The aromatic hydrocarbon group includes monovalent or divalent groups represented by the formulae (a-1) to (e-1) and the formulae (a-2) to (e-2).

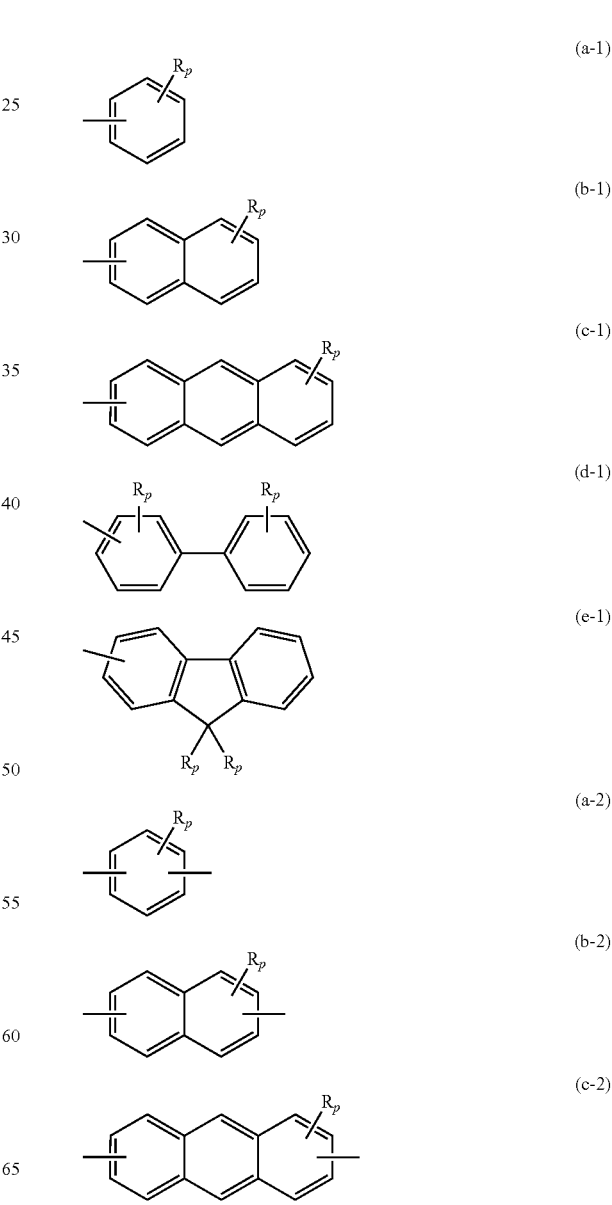

-continued

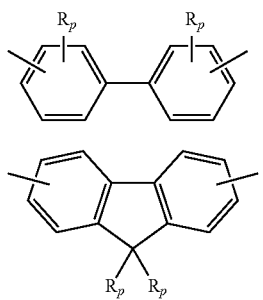
(d-2)

(e-2)

(wherein, R represents a substituent, and p represents an integer of 0 to 4.)

The above-described substituent includes the same groups as exemplified as the substituent of $Ar^1$ and $Ar^2$.

The aromatic hydrocarbon group obtained by substituting a carbon atom contained in an aromatic hydrocarbon group with a hetero atom or a carbonyl group includes monovalent or divalent groups represented by the formulae (f-1) to (z-1) and the formulae (f-2) to (z-2).

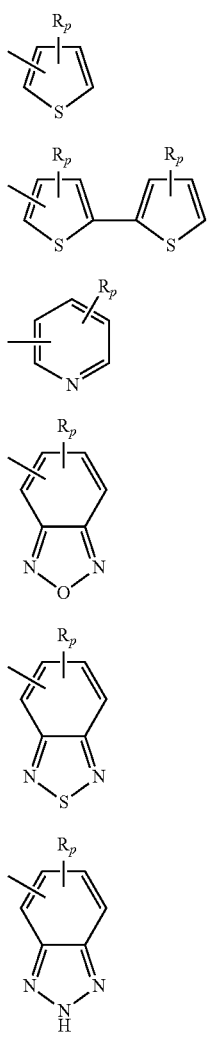

-continued

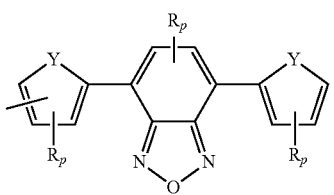
(l-1)

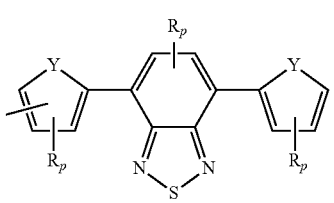
(m-1)

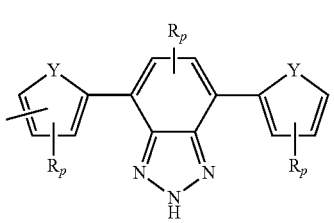
(n-1)

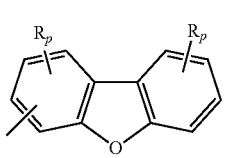
(o-1)

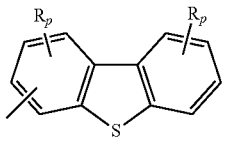
(p-1)

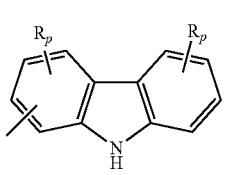
(q-1)

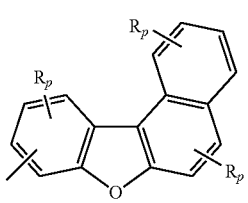
(r-1)

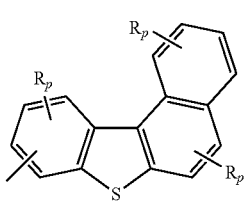
(s-1)

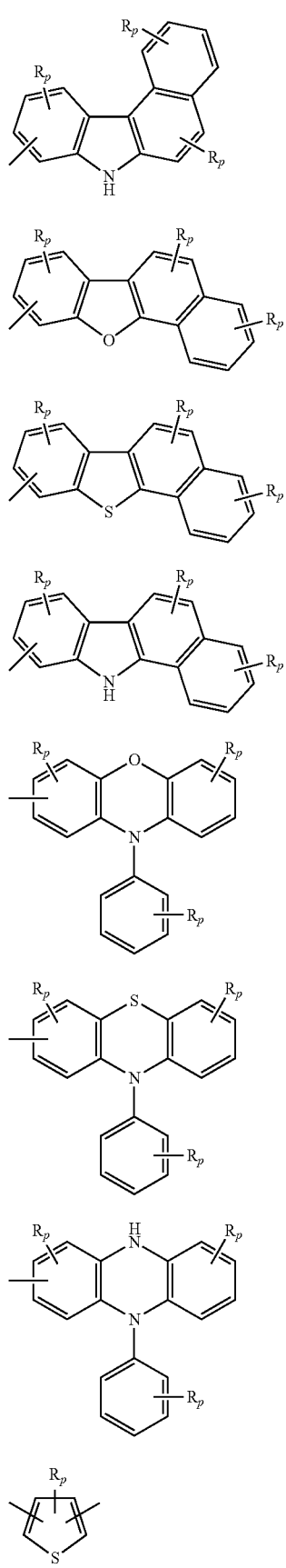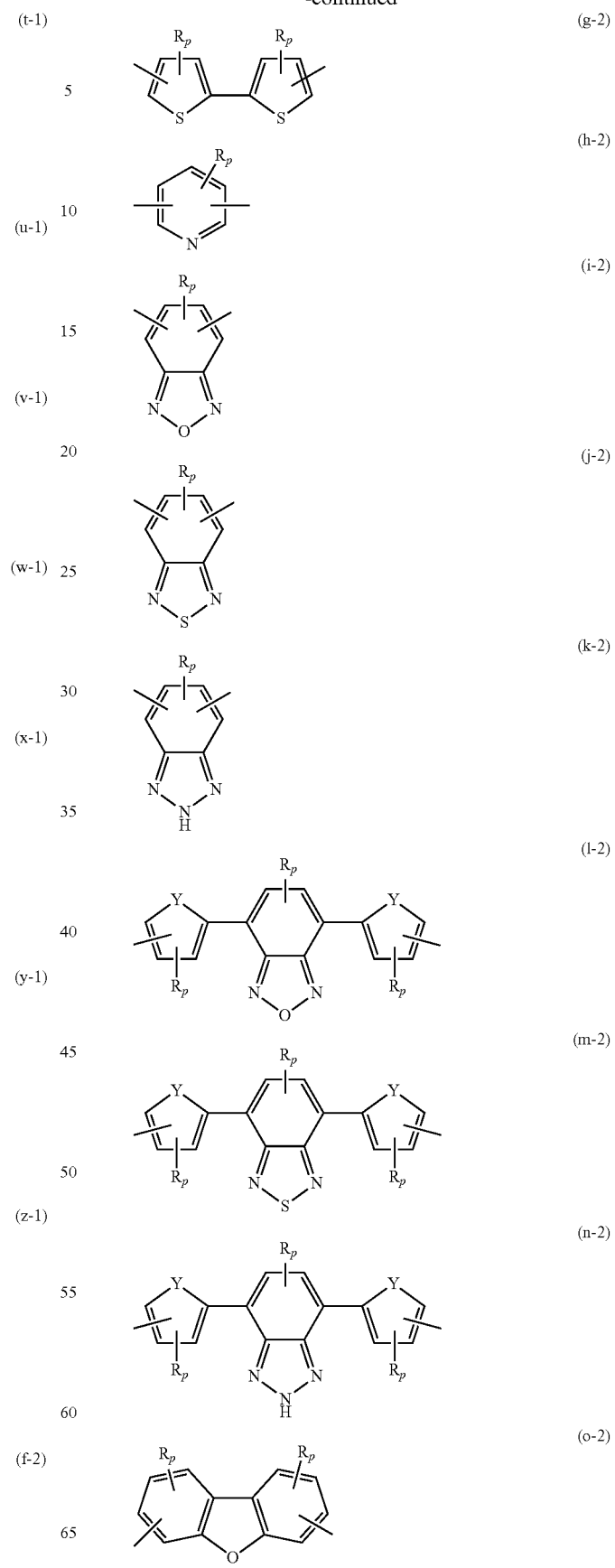

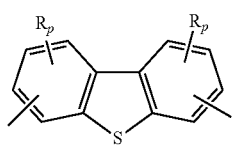
(p-2)

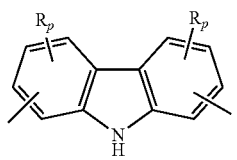
(q-2)

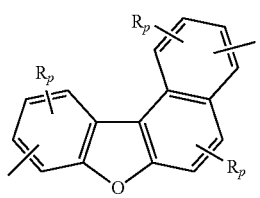
(r-2)

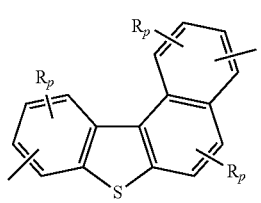
(s-2)

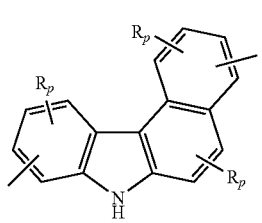
(t-2)

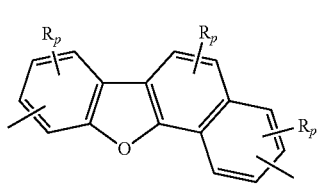
(u-2)

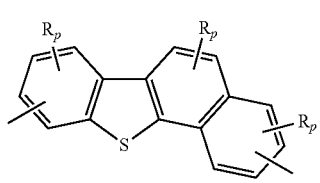
(v-2)

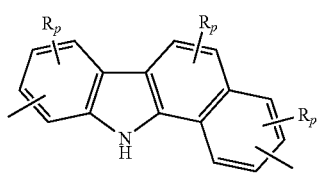
(w-2)

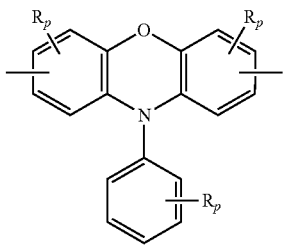
(x-2)

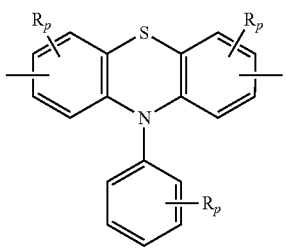
(y-2)

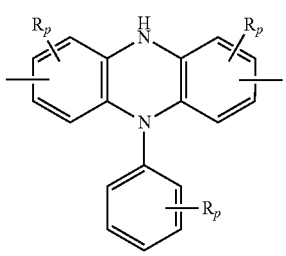
(z-2)

(wherein, R represents a substituent, p represents an integer of 0 to 4, and Y represents N, S or C=O.)

The above-described substituent includes the same groups as exemplified as the substituent of Ar¹ and Ar².

The monovalent or divalent group formed by linking two or more monocyclic aromatic hydrocarbon groups via a single bond, a hetero atom or a carbonyl group includes monovalent or divalent groups represented by the formulae (aa-1) to (ae-1) or the formulae (aa-2) to (ae-2).

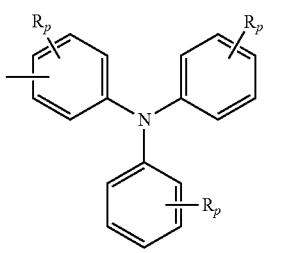
(aa-1)

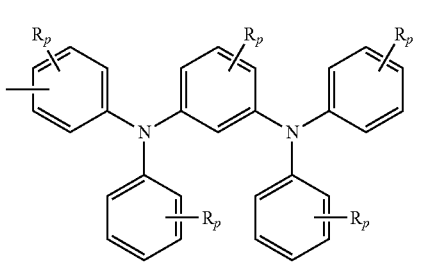
(ab-1)

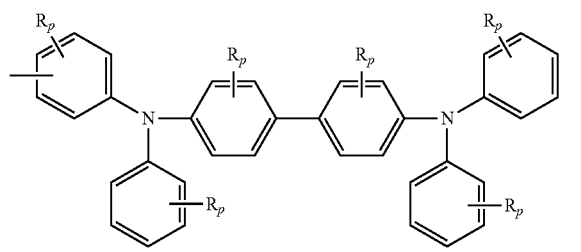
(ac-1)

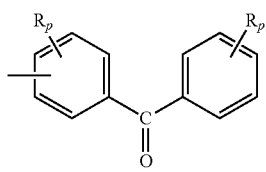
(ad-1)

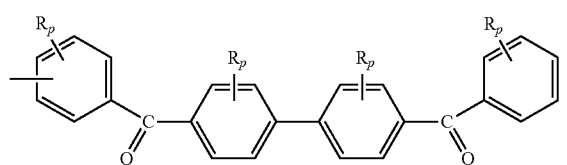
(ae-1)

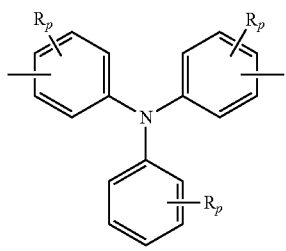
(aa-2)

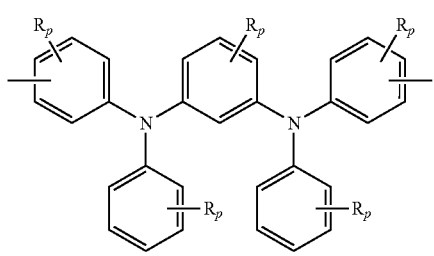
(ab-2)

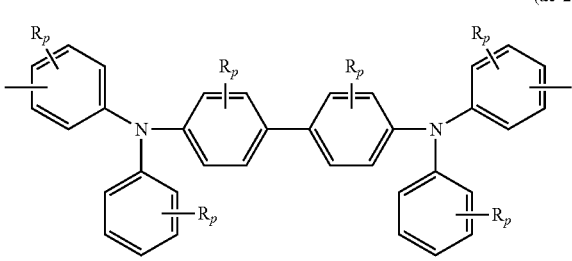
(ac-2)

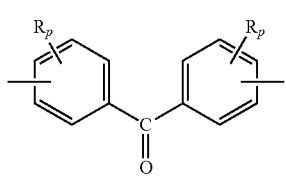
(ad-2)

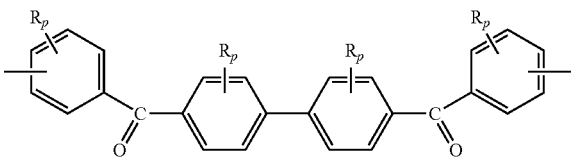
(ae-2)

(wherein, R represents a substituent, and p represents an integer of 0 to 4.)

The above-described substituent includes the same groups as exemplified as the substituent of $Ar^1$ and $Ar^2$.

$Ar^1$ in the above-described formula (A) and $Ar^2$ in the above-described formula (B) may be the same or different.

Preferable examples of $Ar^1$ and $Ar^2$ include groups represented by the formula (a-1), (a-2), (b-1), (b-2), (c-1), (c-2)), (d-1), (d-2), (e-1), (e-2), (m-1), (m-2) (Y in (m-1) and (m-2) is preferably S), (y-1), (y-2), (aa-1) or (aa-2).

$X^1$ in the above-described formula (A) represents a group represented by the formula (1), (2), (3), (4), (5) or (6).

(1)

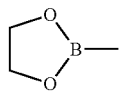
(2)

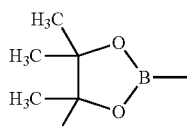
(3)

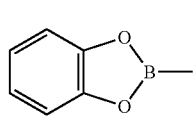
(4)

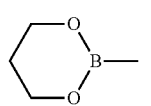
(5)

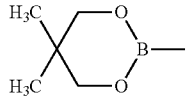
(6)

Preferably, $X^1$ is a group represented by the formula (1), (2), (3) or (5).

The compound represented by the above-described formula (A-1) includes phenylboronic acid, o-tolylboronic acid, m-tolylboronic acid, p-tolylboronic acid, 2,3-dimethylphenylboronic acid, 2,4-dimethylphenylboronic acid, 2,5-dimethylphenylboronic acid, 2,6-dimethylphenylboronic acid, 2,4,6-trimethylphenylboronic acid, 2,3,5,6-tetramethylphenylboronic acid, 2-ethylphenylboronic acid, 4-n-propylphenylboronic acid, 4-isopropylphenylboronic acid, 4-n-butylphenylboronic acid, 4-tert-butylphenylboronic acid, 1-naphthylboronic acid, 2-naphthylboronic acid, 2-biphenylboronic acid, 3-biphenylboronic acid, 4-biphenylboronic acid, 2-fluoro-4-biphenylboronic acid, 2-fluorenylboronic acid, 9-phenanthrenylboronic acid, 9-anthracenylboronic acid, 1-pyrenylboronic acid, 2-trifluoromethylphenylboronic acid, 3-trifluoromethylphenylboronic acid, 4-trifluoromethylphenylboronic acid, 3,5-bis(trifluoromethyl)phenylboronic acid, 2-methoxyphenylboronic acid, 3-methoxyphenylboronic acid, 4-methoxyphenylboronic acid, 2,4-dimethoxyphenylboronic acid, 2,5-dimethoxyphenylboronic acid, 2,6-dimethoxyphenylboronic acid, 3,4-dimethoxyphenylboronic acid, 2-ethoxyphenylboronic acid, 3-ethoxyphenylboronic acid, 4-ethoxyphenylboronic acid, 2-(benzyloxy)phenylboronic acid, 2-phenoxyphenylboronic acid, 4-phenoxyphenylboronic acid, 3,4-methylenedioxyphenylboronic acid, 2-fluorophenylboronic acid, 3-fluorophenylboronic acid, 4-fluorophenylboronic acid, 2,4-difluorophenylboronic acid, 2,5-difluorophenylboronic acid, 2,6-difluorophenylboronic acid, 3,4-difluorophenylboronic acid, 3,5-difluorophenylboronic acid, 2-formylphenylboronic acid, 3-formylphenylboronic acid, 4-formylphenylboronic acid, 3-formyl-4-methoxyphenylboronic acid, 2-cyanophenylboronic acid, 3-cyanophenylboronic acid, 4-cyanophenylboronic acid, 2-acetylphenylboronic acid, 3-acetylphenylboronic acid, 4-acetylphenylboronic acid, 4-vinylphenylboronic acid, 3-carboxyphenylboronic acid, 4-carboxyphenylboronic acid, 3-aminophenylboronic acid, 2-(N,N-dimethylamino)phenylboronic acid, 3-(N,N-dimethylamino)phenylboronic acid, 4-(N,N-dimethylamino)phenylboronic acid, 2-(N,N-diethylamino)phenylboronic acid, 3-(N,N-diethylamino)phenylboronic acid, 4-(N,N-diethylamino)phenylboronic acid, 2-(N,N-diethylaminomethyl)phenylboronic acid, furan-2-boronic acid, furan-3-boronic acid, 5-formylfuran-2-boronic acid, 3-formylfuran-2-boronic acid, benzofuran-2-boronic acid, dibenzofuran-4-boronic acid, thiophene-2-boronic acid, thiophene-3-boronic acid, 4-methylthiophene-2-boronic acid, 5-methylthiophene-2-boronic acid, 5-chlorothiophene-2-boronic acid, 2-acetylthiophene-5-boronic acid, 3-formylthiophene-2-boronic acid, benzothiophene-2-boronic acid, dibenzothiophene-4-boronic acid, pyrazole-4-boronic acid, 3-methylpyrazole-4-boronic acid, 3,5-dimethylpyrazole-4-boronic acid, thiazole-2-boronic acid, pyridine-3-boronic acid, pyridine-4-boronic acid, pyrimidine-5-boronic acid, quinoline-8-boronic acid, isoquinoline-4-boronic acid, 1,4-benzenediboronic acid, 4,4'-biphenyldiboronic acid, vinylboronic acid, 3-methyl-2-buten-2-ylboronic acid and the like.

The compound represented by the above-described formula (A-2) includes 2,2'-(9,9-dihexyl-9H-fluorene-2,7-diyl)bis(1,3,2-dioxaborolane), 2,2'-(9,9-dihexyl-9H-fluorene-2,7-diyl)bis(1,3,2-dioxaborinane), 2,2'-(9,9-dihexyl-9H-fluorene-2,7-diyl)bis(4,4,5,5-tetramethyl-1,3,2-dioxaborolane), 2,2'-(9,9-dihexyl-9H-fluorene-2,7-diyl)bis(5,5-dimethyl-1,3,2-dioxaborinane), 2,2'-(9,9-dioctyl-9H-fluorene-2,7-diyl)bis(1,3,2-dioxaborolane), 2,2'-(9,9-dioctyl-9H-fluorene-2,7-diyl)bis(1,3,2-dioxaborinane), 2,2'-(9,9-dioctyl-9H-fluorene-2,7-diyl)bis(4,4,5,5-tetramethyl-1,3,2-dioxaborolane), 2,2'-(9,9-dioctyl-9H-fluorene-2,7-diyl)bis(5,5-dimethyl-1,3,2-dioxaborinane), 2,2'-(9,9-didodecyl-9H-fluorene-2,7-diyl)bis(1,3,2-dioxaborolane), 2,2'-(9,9-didodecyl-9H-fluorene-2,7-diyl)bis(1,3,2-dioxaborinane), 2,2'-(9,9-didodecyl-9H-fluorene-2,7-diyl)bis(4,4,5,5-tetramethyl-1,3,2-dioxaborolane), 2,2'-(9,9-didodecyl-9H-fluorene-2,7-diyl)bis(5,5-dimethyl-1,3,2-dioxaborinane), 2,2'-(3,5-dimethoxy-9,9-dihexyl-9H-fluorene-2,7-diyl)bis(4,4,5,5-tetramethyl-1,3,2-dioxaborolane), 2,2'-(9-octyl-9H-carbazole-3,6-diyl)bis(1,3,2-dioxaborolane), 2,2'-(1,4-phenylene)bis(5,5-dimethyl-1,3,2-dioxaborinane), 2,2'-(2,5-dimethyl-1,4-phenylene)bis(1,3,2-dioxaborolane), 2,2'-(2-methyl-5-octyl-1,4-phenylene)bis(4,4,5,5-tetramethyl-1,3,2-dioxaborolane), 2,2'-(2,5-butyl-1,4-phenylene)bis(5,5-dimethyl-1,3,2-dioxaborinane), 2,2'-[2,5-bis(hexyloxy)-1,4-phenylene]bis(5,5-dimethyl-1,3,2-dioxaborinane), 2,5-bis(1,3,2-dioxaborolane-2-yl)thiophene, 2,5-bis(4,4,5,5-tetramethyl-1,3,2-dioxaborolane-2-yl)thiophene, 2,5-bis(1,3,2-dioxaborinane-2-yl)thiophene, 2,5-bis(5,5-dimethyl-1,3,2-dioxaborinane-2-yl)thiophene, 1,1'-bis(4,4,5,5-tetramethyl-1,3,2-dioxaborolane-2-yl)-4,4'-biphenyl, 1,1'-bis(1,3,2-dioxaborolane-2-yl)-4,4'-biphenyl, 1,1'-bis(1,3,2-dioxaborinane-2-yl)-4,4'-biphenyl, 1,1'-bis(5,5-dimethyl-1,3,2-dioxaborinane-2-yl)-4,4'-biphenyl and 5,5'-bis(4,4,5,5-tetramethyl-1,3,2-dioxaborolane-2-yl)-2,2'-bithiophene.

Of them, 2,2'-(9,9-dihexyl-9H-fluorene-2,7-diyl)bis(4,4,5,5-tetramethyl-1,3,2-dioxaborolane), 2,2'-(9,9-dioctyl-9H-fluorene-2,7-diyl)bis(4,4,5,5-tetramethyl-1,3,2-dioxaborolane), 2,2'-(9,9-didodecyl-9H-fluorene-2,7-diyl)bis(4,4,5,5-tetramethyl-1,3,2-dioxaborolane), 2,2'-(3,5-dimethoxy-9,9-dihexyl-9H-fluorene-2,7-diyl)bis(4,4,5,5-tetramethyl-1,3,2-dioxaborolane), 2,2'-(2-methyl-5-octyl-1,4-phenylene)bis(4,4,5,5-tetramethyl-1,3,2-dioxaborolane), 2,5-bis(4,4,5,5-tetramethyl-1,3,2-dioxaborolane-2-yl)thiophene, 1,1'-bis(4,4,5,5-tetramethyl-1,3,2-dioxaborolane-2-yl)-4,4'-biphenyl and 5,5'-bis(4,4,5,5-tetramethyl-1,3,2-dioxaborolane-2-yl)-2,2'-bithiophene are preferable.

In the production method of the present invention, two or more compounds represented by the formula (A) may be used in combination.

$X^2$ in the above-described formula (B) includes a chlorine atom, a bromine atom, an iodine atom, an alkylsulfonyloxy group, a fluorine-substituted alkylsulfonyloxy group or an arylsulfonyloxy group. Such $X^2$ links to a monovalent or divalent aromatic hydrocarbon group.

"Alkylsulfonyloxy group" includes a methanesulfonyloxy group and the like.

"Fluorine-substituted alkylsulfonyloxy group" includes a trifluoromethanesulfonyloxy group and the like.

"Arylsulfonyloxy group" includes a p-toluenesulfonyloxy group and the like.

The compound represented by the (B-1) includes phenyl bromide, o-tolyl bromide, m-tolyl bromide, p-tolyl bromide, 4-tert-butylphenyl bromide, 2,6-dimethylphenyl bromide, 2,4-dimethylphenyl bromide, 3,5-dimethylphenyl bromide, 2-(2-hydroxyethyl)phenyl bromide, 4-cyclohexylphenyl bromide, 3-bromobenzo trifluoride, 3-bromo-4-chlorobenzo trifluoride, 2-naphthyl bromide, 9-bromoanthracene, 9,10-dibromoanthracene, m-methoxyphenyl bromide, 4-bromobenzaldehyde, methyl 2-bromophenylacetate, methyl 3-bromophenylacetate, ethyl 4-bromophenylacetate, methyl 3-bromocinnamate, methyl 5-bromosalicylate, 4-bromobenzamide, 4-bromobenzonitrile, 9-bromophenanthrene, 2-bromofluorene, 5-bromoindanone, 6-bromo-2-naphthol, 2-pyridyl bromide, 2-bromofuran, 3-bromofuran, 2-bromothiophene, 4-bromopyrazole, 2-bromothiazole, 2-methyl-5-bromobenzothiazole, 5-bromouracil, 8-bromoquinoline, 4-bromoisoquinoline, 1-benzyl-5-bromotetrazole, phenyl chloride, o-tolyl chloride, 4-tert-butylphenyl chloride, 3-chlorotoluene, 4-chlorotoluene, 2,6-dimethylphenyl chloride, 3,5-dimethylphenyl chloride, 4-cyclohexyl chloride, 2-chloroacetophenone, 4-chloroacetophenone, 2-chloro-4-fluorotoluene, methyl 2-chlorophenylacetate, methyl 3-chlorophenylacetate, ethyl 4-chlorophenylacetate, 3-chlorobenzophenone, 4-chloro-1-naphthol, 4-chloro-N,N-dimethylaniline, 4-chloro-N,N-diphenylaniline, 5-chloro-N,N-dimethylaniline, 5-chloro-2-methoxyaniline, methyl 2-chlorobenzoate, ethyl 4-chlorobenzoate, phenyl 2-chlorobenzoate, N-(2-chlorophenyl)acetamide, N-(4-chlorophenyl)acetamide, 2-chlorobenzyl cyanide, 1-naphthyl chloride, 2-naphthyl chloride, 9-chloroanthracene, 2-methoxyphenyl chloride, 3-methoxyphenyl chloride, 4-methoxyphenyl chloride, 3,5-dimethoxy-2-chlorotoluene, 3-chlorobenzonitrile, 2-chloro-3-morpholino-1,4-naphthoquinone, 3-chlorobenzaldehyde, 2-pyridyl chloride, 2-chloro-6-trifluoropyridine, 2-chloro-3-picoline, 1-(3-chlorophenyl)-3-methyl-2-pyrazolin-5-one, 3-chlorothiophene, 2-chloro-3-methylthiophene, 5-chloro-1-methylimidazole, 5-chloro-1-methylbenzotriazole, 5-chloro-1-phenyl-1H-tetrazole, 4-chloro-1-methylindole, 2-chlorobenzoimidazole, 8-chloro-5-methoxyquinoline, 2-chlorobenzooxazole, 2-methyl-5-chlorobenzooxazole, 2-chlorobenzothiazole, 2-methyl-5-chlorobenzothiazole, 6-chloro-9-methyl-9H-purine, 2-chloropyrazine, phenyl iodide, o-tolyl iodide, 4-tert-butylphenyl iodide, 2,6-dimethylphenyl iodide, 3,5-dimethylphenyl iodide, 4-iodoacetophenone, ethyl 2-iodobenzoate, 2-naphthyl iodide, 9-iodoanthracene, 3-methoxyphenyl iodide, N-tert-butoxycarbonyl-4-iodophenylalanine methyl ester, 2-methyl-5-iodobenzooxazole, 2-methyl-5-iodobenzothiazole, 2-pyridyl iodide, 2-methyl-5-(p-toluenesulfonyloxy)benzooxazole, phenyl trifluoromethane sulfonate, 4-methylphenyl trifluoromethane sulfonate, 2,6-dimethylphenyl trifluoromethane sulfonate, 2-methane sulfonate, 2-methyl-5-(trifluoromethanesulfonyloxy)benzothiazole and the like.

The compound represented by the formula (B-2) includes 2,7-dibromo-9,9-dihexyl-9H-fluorene, 2,7-dibromo-9,9-dioctyl-9H-fluorene, 2,7-dibromo-9,9-didodecyl-9H-fluorene, 2,7-dichloro-9,9-dihexyl-9H-fluorene, 2,7-dichloro-9,9-dioctyl-9H-fluorene, 2,7-dichloro-9,9-didodecyl-9H-fluorene, 2-bromo-7-chloro-9,9-dihexyl-9H-fluorene, 2-bromo-7-chloro-9,9-dioctyl-9H-fluorene, 2-bromo-7-chloro-9,9-didodecyl-9H-fluorene, 1,4-dibromobenzene, 1,3-dibromobenzene, 1,4-dibromo-2-ethylbenzene, 1,4-dibromo-2-methoxybenzene, dimethyl 2,5-dibromo terephthalate, 1,4-dibromonaphthalene, 3,5-dibromopyridine, 1,1'-dibromo-4,4'-biphenyl, 2,5-dibromopyridine, 1,4-dibromo-2,5-dihexyloxybenzene, 1-bromo-4-chlorobenzene, 1-bromo-4-chlorotoluene, 1-bromo-4-chloro-2-propylbenzene, 2,5-dibromo-4'-phenoxybenzophenone, 2,5-dibromo-3-hexylthiophene, 2,5-dibromo-3,2,5-dibromo-3-octylthiophene-dodecylthiophene, 2,5-dichloro-3-hexylthiophene, 5,5'-dibromo-2,2'-bithiophene, 5,5'-dibromo-3,3'-dihexyl-2,2'-bithiophene, bis(4-bromophenyl)-4-(4-t-butyl)benzeneamine, bis(4-bromophenyl)-4-(1-methylpropyl)benzeneamine, bis(4-bromophenyl)-4-benzeneamine, N,N'-bis(4-bromophenyl)-N,N'-bis(4-n-butylphenyl)-1,4-benzenediamine, N,N'-bis(4-bromophenyl)-bicyclo[4,2,0]octa-1,3,5-triene-3-amine, N,N'-bis(4-bromophenyl)-N,N'-bis(4-butylphenyl)-1,4-benzenediamine, N,N'-bis(4-bromophenyl)-N,N'-bis[4-(1,1-dimethylethyl)-2,6-dimethylphenyl]-1,4-benzenediamine, 4,7-dibromo-2,1,3-benzothiadiazole, 4,7-dibromo-2,1,3-benzoselenadiazole, 4,7-bis(5-bromo-2-thienyl)-2,1,3-benzothiadiazole, 4,7-bis(5-bromo-4-methyl-2-thienyl)-2,1,3-benzothiadiazole, 4,7-bis(5-bromo-3-methyl-2-thienyl)-2,1,3-benzothiadiazole, 3,7-dibromo-10-(4-n-butylphenyl)-10H-phenothiazine, 3,7-dibromo-10-(4-n-butylphenyl)-10H-phenoxazine, 3,3'-[1,1'-biphenyl]-4,4'-diylbis[[4-bromophenyl]imino]]bisbenzoic acid diethyl ester and 4,4'-bis[(4-bromophenyl)phenylamino]biphenyl.

Of them, 2,7-dibromo-9,9-dihexyl-9H-fluorene, 2,7-dibromo-9,9-dioctyl-9H-fluorene, 2,7-dibromo-9,9-didodecyl-9H-fluorene, 1,4-dibromobenzene, 1,3-dibromobenzene, 2,5-dibromo-3-hexylthiophene and bis(4-bromophenyl)-4-benzeneamine are preferable.

In the production method of the present invention, two or more compounds represented by the formula (B) may be used in combination.

The use amount of the compound represented by the formula (B) is usually in the range of 0.8 mol to 1.2 mol, preferably in the range of 0.9 mol to 1.1 mol with respect to 1 mol of a compound represented by the formula (A).

<Base>

The base includes inorganic bases and organic bases.

The inorganic base includes alkali metal hydroxides, alkaline earth metal hydroxides, alkali metal carboxylic acid salts, alkaline earth metal carboxylic acid salts, alkali metal carbonates, alkaline earth metal carbonates, alkali metal hydrogen carbonates, alkaline earth metal hydrogen carbonates, alkali metal phosphates and alkaline earth metal phosphates, and alkali metal carbonates and alkali metal phosphates are preferable.

The inorganic base includes lithium hydroxide, sodium hydroxide, potassium hydroxide, cesium hydroxide, calcium hydroxide, barium hydroxide, sodium formate, potassium formate, calcium formate, sodium acetate, potassium acetate, sodium carbonate, potassium carbonate, cesium carbonate, calcium carbonate, sodium hydrogen carbonate, potassium hydrogen carbonate, sodium phosphate and potassium phosphate, and sodium carbonate, potassium carbonate, cesium carbonate, sodium phosphate and potassium phosphate are preferable.

The organic base includes alkylammonium hydroxides, alkylammonium carbonates, alkylammonium bicarbonates, alkylammonium boronic acid salts, 1,5-diazabicyclo[4.3.0]non-5-ene (DBN), 1,8-diazabicyclo[5.4.0]undec-7-ene (DBU), 1,4-diazabicyclo[2.2.2]octane (DABCO), dimethylaminopyridine (DMAP), pyridine, trialkylamine, and alkylammonium fluorides such as tetraalkylammonium fluoride and the like. Of them, tetraalkylammonium hydroxides such as tetramethylammonium hydroxides, tetraethylammonium hydroxides, tetra-n-propylammonium hydroxides and the like are preferable.

The use amount of the base is usually in the range of 0.5 equivalent to 20 equivalent, preferably in the range of 0.5 equivalent to 6 equivalent. Here, the equivalent signifies the ratio of the theoretical substance amount of a base necessary for neutralizing hydrogen ions equivalent to the total substance amount of $X^2$ contained in a compound represented by the formula (B) to the total substance amount of $X^2$ contained in a compound represented by the formula (B).

<Phase Transfer Catalyst>

When an inorganic base is used as the base in the production method of the present invention, a phase transfer catalyst may also be used together. The phase transfer catalyst includes tetraalkyl ammonium halide, tetraalkylammonium hydrogen sulfate and tetraalkylammonium hydroxide. Tetraalkylammonium halides such as tricaprylmethylammonium chloride (available as Aliquat (registered trademark) 336 from Sigma-Aldrich) and the like are preferable.

The use amount of the phase transfer catalyst is usually in the range of 0.001 equivalent to 1 equivalent, preferably in the range of 0.01 equivalent to 0.5 equivalent. Here, the equivalent signifies the ratio to the total substance amount of $X^2$ contained in a compound represented by the formula (B).

<Aprotic Organic Solvent>

"Aprotic organic solvent" denotes an organic solvent not having a group having active hydrogen such as a hydroxyl group (—OH), an amino group, a carboxyl group (—COOH) and the like in its molecule and capable of dissolving a compound represented by the formula (A) and a compound represented by the formula (B).

The aprotic organic solvent includes ether solvents such as an acyclic ether solvent, a cyclic ether solvent and the like, aprotic polar solvents, aromatic hydrocarbon solvents and aliphatic hydrocarbon solvents, and ether solvents, aromatic hydrocarbon solvents and aliphatic hydrocarbon solvents are preferable. The aprotic polar solvent includes N-methylpyrrolidone, N,N-dimethylformamide, N,N-dimethylacetamide, dimethyl sulfoxide and acetonitrile. The acyclic ether solvent includes diethyl ether, diisopropyl ether, ethylene glycol dimethyl ether and diethylene glycol dimethyl ether. The cyclic ether solvent includes 1,4-dioxane and tetrahydrofuran. The aromatic hydrocarbon solvent includes benzene, toluene, xylene and mesitylene. The aliphatic hydrocarbon solvent includes hexane, heptane and cyclohexane.

Preferable from the standpoint of the solubility of a compound represented by the formula (A) and a compound represented by the formula (B) are toluene, xylene, mesitylene, diethyl ether, diisopropyl ether, ethylene glycol dimethyl ether, diethylene glycol dimethyl ether, 1,4-dioxane and tetrahydrofuran. If necessary, two or more aprotic organic solvents may be used in combination, and specific examples thereof include a mixed solvent of tetrahydrofuran and toluene and a mixed solvent of ethylene glycol dimethyl ether and toluene.

<Palladium Compound>

The palladium compound is a compound in which an atom other than palladium is linked to palladium, and includes preferably a palladium(0) complex and a palladium (II) complex.

The palladium(0) complex includes a complex in which dibenzylideneacetone is coordinated to 0-valent palladium, what is called a dibenzylideneacetone-palladium(0) complex. Specific examples thereof include tris(dibenzylideneacetone)dipalladium(0), tris(dibenzylideneacetone)dipalladium(0) chloroform adduct and bis(dibenzylideneacetone)palladium(0).

The palladium(II) complex includes palladiumcarboxylic acid salts such as palladium(II) acetate, palladium(II) trifluoroacetate, palladium(II) acetylacetonate and the like, palladium halides such as palladium(II) chloride, palladium(II) bromide, palladium(II) iodide and the like, and palladium halide complexes such as allylpalladium(II) chloride dimer, bis(2-methylallyl)palladium(II) chloride dimer, dichloro(1,5-cyclooctadiene)palladium(II), dichlorobis(acetonitrile)palladium(II), dichlorobis(benzonitrile)palladium (II) and the like. Of them, tris(dibenzylideneacetone)dipalladium(0), bis(dibenzylideneacetone)palladium(0), palladium(II) chloride, palladium(II) bromide and palladium (II) acetate are preferable.

The use amount of the palladium compound is usually in the range of 0.00001 mol to 0.8 mol, preferably in the range of 0.00002 mol to 0.2 mol with respect to 1 mol of a compound represented by the formula (B).

<Phosphine Represented by the Formula (C)>

The phosphine represented by the formula (C) is represented by the following formula (C).

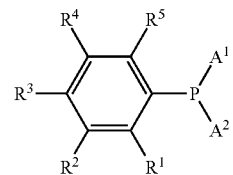

(C)

In the formula (C), $A^1$ and $A^2$ represent each independently an alkyl group having a number of carbon atoms of 1 to 20 or a saturated alicyclic hydrocarbon group having a number of carbon atoms of 6 to 20.

$A^1$ and $A^2$ may be the same or different. Preferably, $A^1$ and $A^2$ are the same.

The alkyl group having a number of carbon atoms of 1 to 20 includes a methyl group, an ethyl group, a n-propyl group, an isopropyl group, a n-butyl group, an isobutyl group, a sec-butyl group, a tert-butyl group, a n-pentyl group, a 2,2-dimethylpropyl group, a n-hexyl group, a n-heptyl group, a 2-methylpentyl group, a n-octyl group, a 2-ethylhexyl group, a n-nonyl group, a n-decyl group, a n-undecyl group, a n-dodecyl group, a n-tridecyl group, a n-tetradecyl group, a n-pentadecyl group, a n-hexadecyl group, a n-heptadecyl group, a n-octadecyl group, a n-nonadecyl group and a n-icosyl group, and an alkyl group having a number of carbon atoms of 1 to 6 is preferable, a tert-butyl group is more preferable. The saturated alicyclic hydrocarbon group having a number of carbon atoms of 6 to 20 includes a cyclohexyl group, a cycloheptyl group, a cyclooctyl group, a cyclononyl group and a 1-adamantyl group, and a cycloalkyl group having a number of carbon atoms of 6 to 8 is preferable, a cyclohexyl group is more preferable.

In the formula (C), $R^1$ and $R^5$ represent each independently a hydrogen atom, an alkoxy group having a number of carbon atoms of 1 to 20 or a cycloalkoxy group having a number of carbon atoms of 3 to 20.

The alkoxy group having a number of carbon atoms of 1 to 20 includes a methoxy group, an ethoxy group, a n-propoxy group, an isopropoxy group, a n-butoxy group, a sec-butoxy group, a tert-butoxy group, a n-pentyloxy group, a 2,2-dimethylpropoxy group, a n-hexyloxy group, a n-heptyloxy group, a n-octyloxy group, a n-nonyloxy group, a n-decyloxy group, a n-undecyloxy group, a n-dodecyloxy group, a n-tridecyloxy group, a n-tetradecyloxy group, a n-pentadecyloxy group, a n-hexadecyloxy group, a n-heptadecyloxy group, a n-octadecyloxy group, a n-nonadecyloxy group and a n-icosyloxy group, and an alkoxy group having a number of carbon atoms of 1 to 6 is preferable.

The cycloalkoxy group having a number of carbon atoms of 3 to 20 includes a cyclopentyloxy group and a cyclohexyloxy group, and a cycloalkoxy group having a number of carbon atoms of 3 to 8 is preferable.

$R^1$ and $R^5$ preferably represent each independently a hydrogen atom or an alkoxy group having a number of carbon atoms of 1 to 6. It is more preferable that $R^1$ and $R^5$ are both a hydrogen atom.

In the formula (C), $R^2$, $R^3$ and $R^4$ represent each independently a hydrogen atom, a fluorine atom, an alkyl group having a number of carbon atoms of 1 to 20, a cycloalkyl group having a number of carbon atoms of 3 to 20, an alkoxy group having a number of carbon atoms of 1 to 20, a cycloalkoxy group having a number of carbon atoms of 3 to 20, a fluoroalkoxy group having a number of carbon atoms of 1 to 20, a fluorocycloalkoxy group having a number of carbon atoms of 3 to 30, or an aryl group having a number of carbon atoms of 6 to 20.

The alkyl group having a number of carbon atoms of 1 to 20 includes a methyl group, an ethyl group, a n-propyl group, an isopropyl group, a n-butyl group, an isobutyl group, a sec-butyl group, a tert-butyl group, a n-pentyl group, a 2,2-dimethylpropyl group, a n-hexyl group, a n-heptyl group, a 2-methylpentyl group, a n-octyl group, a 2-ethylhexyl group, a n-nonyl group, a n-decyl group, a n-undecyl group, a n-dodecyl group, a n-tridecyl group, a n-tetradecyl group, a n-pentadecyl group, a n-hexadecyl group, a n-heptadecyl group, a n-octadecyl group, a n-nonadecyl group and a n-icosyl group, and an alkyl group having a number of carbon atoms of 1 to 6 is preferable.

The cycloalkyl group having a number of carbon atoms of 3 to 20 includes a cyclopentyl group and a cyclohexyl group.

The alkoxy group having a number of carbon atoms of 1 to 20 includes a methoxy group, an ethoxy group, a n-propoxy group, an isopropoxy group, a n-butoxy group, a sec-butoxy group, a tert-butoxy group, a n-pentyloxy group, a 2,2-dimethylpropoxy group, a n-hexyloxy group, a n-heptyloxy group, a n-octyloxy group, a n-nonyloxy group, a n-decyloxy group, a n-undecyloxy group, a n-dodecyloxy group, a n-tridecyloxy group, a n-tetradecyloxy group, a n-pentadecyloxy group, a n-hexadecyloxy group, a n-heptadecyloxy group, a n-octadecyloxy group, a n-nonadecyloxy group and a n-icosyloxy group, and an alkoxy group having a number of carbon atoms of 1 to 6 is preferable.

The cycloalkoxy group having a number of carbon atoms of 3 to 20 includes a cyclopentyloxy group and a cyclohexyloxy group.

The fluoroalkoxy group having a number of carbon atoms of 1 to 20 includes a monofluoromethoxy group, a difluoromethoxy group, a trifluoromethoxy group, a 2,2,2-trifluoroethoxy group, a pentafluoroethoxy group, a perfluoro-n-propoxy group and a perfluoroisopropoxy group, and a fluoroalkoxy group having a number of carbon atoms of 1 to 6 is preferable.

The fluorocycloalkoxy group having a number of carbon atoms of 3 to 30 includes a 4-fluorocyclohexyloxy group, a 4,4-dicyclohexyloxy group and the like.

The aryl group having a number of carbon atoms of 6 to 20 includes a phenyl group, a 4-methylphenyl group, a 2-methylphenyl group, a 1-naphthyl group, a 2-naphthyl group, a 3-phenanthryl group and a 2-anthryl group.

It is preferable that $R^2$, $R^3$ and $R^4$ represent each independently a hydrogen atom, a fluorine atom, an alkyl group having a number of carbon atoms of 1 to 20, an alkoxy group having a number of carbon atoms of 1 to 20, a fluoroalkoxy group having a number of carbon atoms of 1 to 20 or an aryl group having a number of carbon atoms of 6 to 20, and it is more preferable that $R^2$, $R^3$ and $R^4$ represent each independently a hydrogen atom, a fluorine atom, an alkyl group having a number of carbon atoms of 1 to 6, an alkoxy group having a number of carbon atoms of 1 to 6, a fluoroalkoxy group having a number of carbon atoms of 1 to 6 or an aryl group having a number of carbon atoms of 6 to 20. It is preferable that $R^3$ represents a hydrogen atom, and it is preferable that $R^2$ and $R^4$ represent a hydrogen atom, a fluorine atom, an alkyl group having a number of carbon atoms of 1 to 6, an alkoxy group having a number of carbon atoms of 1 to 6, a fluoroalkoxy group having a number of carbon atoms of 1 to 6 or an aryl group having a number of carbon atoms of 6 to 20. It is more preferable that $R^3$ represents a hydrogen atom and $R^2$ and $R^4$ represent a hydrogen atom, a fluorine atom, an alkyl group having a number of carbon atoms of 1 to 6, an alkoxy group having a number of carbon atoms of 1 to 6, a fluoroalkoxy group having a number of carbon atoms of 1 to 6 or an aryl group having a number of carbon atoms of 6 to 20.

In the formula (C), all of $R^1$ to $R^5$ do not simultaneously represent a hydrogen atom. Further, $R^2$ and $R^3$ may be linked to form a ring (for example, a benzene ring) together with a carbon atom to which they are linked, and $R^3$ and $R^4$ may be linked to form a ring (for example, a benzene ring) together with a carbon atom to which they are linked.

The phosphine represented by the formula (C) includes
a phosphine represented by the formula (C) in which $A^1$ and $A^2$ represent an alkyl group having a number of carbon atoms of 1 to 6, a phosphine represented by the formula (C) in which $A^1$ and $A^2$ represent a tert-butyl group, a phosphine represented by the formula (C) in which $A^1$ and $A^2$ represent a cycloalkyl group having a number of carbon atoms of 6 to 8, a phosphine represented by the formula (C) in which $A^1$ and $A^2$ represent a cyclohexyl group, a phosphine represented by the formula (C) in which $R^2$ and $R^4$ represent a fluorine atom, an alkyl group having a number of carbon atoms of 1 to 6, an alkoxy group having a number of carbon atoms of 1 to 6, a fluoroalkoxy group having a number of carbon atoms of 1 to 6 or an aryl group having a number of carbon atoms of 6 to 20, a phosphine represented by the formula (C) in which $A^1$ and $A^2$ represent an alkyl group having a number of carbon atoms of 1 to 6 and $R^2$ and $R^5$ represent a hydrogen atom, a phosphine represented by the formula (C) in which $A^1$ and $A^2$ represent a tert-butyl group and $R^2$ and $R^5$ represent a hydrogen atom, a phosphine represented by the formula (C) in which $A^1$ and $A^2$ represent a cycloalkyl group having a number of carbon atoms of 6 to 8 and $R^2$ and $R^5$ represent a hydrogen atom, a phosphine represented by the formula (C) in which $A^1$ and $A^2$ represent a cyclohexyl group and $R^2$ and $R^5$ represent a hydrogen atom, a phosphine represented by the formula (C) in which $A^1$ and $A^2$ represent an alkyl group having a number of carbon atoms of 1 to 6, $R^2$ represents a hydrogen atom and $R^5$ represents an alkoxy group having a number of carbon atoms of 1 to 6, a phosphine represented by the formula (C) in which $A^1$ and $A^2$ represent a tert-butyl group, $R^2$ represents a hydrogen atom and $R^5$ represents an alkoxy group having a number of carbon atoms of 1 to 6, a phosphine represented by the formula (C) in which $A^1$ and $A^2$ represent a cycloalkyl group having a number of carbon atoms of 6 to 8, $R^1$ represents a hydrogen atom and $R^5$ represents an alkoxy group having a number of carbon atoms of 1 to 6, a phosphine represented by the formula (C) in which $A^1$ and $A^2$ represent a cyclohexyl group, $R^1$ represents a hydrogen atom and $R^5$ represents an alkoxy group having a number of carbon atoms of 1 to 6, a phosphine represented by the formula (C) in which $A^1$ and $A^2$ represent an alkyl group having a number of carbon atoms of 1 to 6, $R^2$ and $R^4$ represent a hydrogen atom and $R^3$ represents a fluorine atom, an alkyl group having a number of carbon atoms of 1 to 6, an alkoxy group having a number of carbon atoms of 1 to 6, a fluoroalkoxy group having a number of carbon atoms of 1 to 6 or an aryl group having a number of carbon atoms of 6 to 20, a phosphine represented by the formula (C) in which $A^1$ and $A^2$ represent a tert-butyl group, $R^2$ and $R^4$ represent a hydrogen atom and $R^3$ represents a fluorine atom, an alkyl group having a number of carbon atoms of 1 to 6, an alkoxy group having a number of carbon atoms of 1 to 6, a fluoroalkoxy group having a number of carbon atoms of 1 to 6 or an aryl group having a number of carbon atoms of 6 to 20, a phosphine represented by the formula (C) in which $A^1$ and $A^2$ represent a cycloalkyl group having a number of carbon atoms of 6 to 8, $R^2$ and $R^4$ represent a hydrogen atom and $R^3$ represents a fluorine atom, an alkyl group having a number of carbon atoms of 1 to 6, an alkoxy group having a number of carbon atoms of 1 to 6, a fluoroalkoxy group having a number of carbon atoms of 1 to 6 or an aryl group having a number of carbon atoms of 6 to 20, a phosphine represented by the formula (C) in which $A^1$ and $A^2$ represent a cyclohexyl group, $R^2$ and $R^4$ represent a hydrogen atom and $R^3$ represents a fluorine atom, an alkyl group having a number of carbon atoms of 1 to 6, an alkoxy group having a number of carbon atoms of 1 to 6, a fluoroalkoxy group having a number of carbon atoms of 1 to 6 or an aryl group having a number of carbon atoms of 6 to 20, a phosphine represented by the formula (C) in which $A^1$ and $A^2$ represent an alkyl group having a number of carbon atoms of 1 to 6, $R^3$ represents a hydrogen atom and $R^2$ and $R^4$ represent a fluorine atom, an alkyl group having a number of carbon atoms of 1 to 6, an alkoxy group having a number of carbon atoms of 1 to 6, a fluoroalkoxy group having a number of carbon atoms of 1 to 6 or an aryl group having a number of carbon atoms of 6 to 20, a phosphine represented by the formula (C) in which $A^1$ and $A^2$ represent a tert-butyl group, $R^3$ represents a hydrogen atom and $R^2$ and $R^4$ represent a fluorine atom, an alkyl group having a number of carbon atoms of 1 to 6, an alkoxy group having a number of carbon atoms of 1 to 6, a fluoroalkoxy group having a number of carbon atoms of 1 to 6 or an aryl group having a number of carbon atoms of 6 to 20, a phosphine represented by the formula (C) in which $A^1$ and $A^2$ represent a cycloalkyl group having a number of carbon atoms of 6 to 8, $R^3$ represents a hydrogen atom and $R^2$ and $R^4$ represent a fluorine atom, an alkyl group having a number of carbon atoms of 1 to 6, an alkoxy group having a number of carbon atoms of 1 to 6, a fluoroalkoxy group having a number of carbon atoms of 1 to 6 or an aryl group having a number of carbon atoms of 6 to 20, a phosphine represented by the formula (C) in which $A^1$ and $A^2$ represent a cyclohexyl group, $R^3$ represents a hydrogen atom and $R^2$ and $R^4$ represent a fluorine atom, an alkyl group having a number of carbon atoms of 1 to 6, an alkoxy group having a number of carbon atoms of 1 to 6, a fluoroalkoxy group having a number of carbon atoms of 1 to 6 or an aryl group having a number of carbon atoms of 6 to 20, a phosphine represented by the formula (C) in which $A^1$ and $A^2$ represent an alkyl group having a number of carbon atoms of 1 to 6, $R^1$ represents a hydrogen atom, $R^5$ represents an alkoxy group having a number of carbon atoms of 1 to 6, $R^2$ and $R^4$ represent a hydrogen atom and $R^3$ represents a fluorine atom, an alkyl group having a number of carbon atoms of 1 to 6, an alkoxy group having a number of carbon atoms of 1 to 6, a fluoroalkoxy group having a number of carbon atoms of 1 to 6 or an aryl group having a number of carbon atoms of 6 to 20, a phosphine represented by the formula (C) in which $A^1$ and $A^2$ represent a tert-butyl group, $R^1$ represents a hydrogen atom, $R^5$ represents an alkoxy group having a number of carbon atoms of 1 to 6, $R^2$ and $R^4$ represent a hydrogen atom and $R^3$ represents a fluorine atom, an alkyl group having a number of carbon atoms of 1 to 6, an alkoxy group having a number of carbon atoms of 1 to 6, a fluoroalkoxy group having a number of carbon atoms of 1 to 6 or an aryl group having a number of carbon atoms of 6 to 20, a phosphine represented by the formula (C) in which $A^1$ and $A^2$ represent a cycloalkyl group having a number of carbon atoms of 6 to 8, $R^1$ represents a hydrogen atom, $R^5$ represents an alkoxy group having a number of carbon atoms of 1 to 6, $R^2$ and $R^4$ represent a hydrogen atom and $R^3$ represents a fluorine atom, an alkyl group having a number of carbon atoms of 1 to 6, an alkoxy group having a number of carbon atoms of 1 to 6, a fluoroalkoxy group having a number of carbon atoms of 1 to 6 or an aryl group having a number of carbon atoms of 6 to 20, a phosphine represented by the formula (C) in which $A^1$ and $A^2$ represent a cyclohexyl group, $R^1$ represents a hydrogen atom, $R^5$ represents an alkoxy group having a number of carbon atoms of 1 to 6, $R^2$ and $R^4$ represent a hydrogen atom and $R^3$ represents a fluorine atom, an alkyl group having a number of carbon atoms of 1 to 6, an alkoxy group having a number of carbon atoms of 1 to 6, a fluoroalkoxy group having a number of carbon atoms of 1 to 6 or an aryl group having a number of carbon atoms of 6 to 20, a phosphine represented by the formula (C) in which $A^1$ and $A^2$ represent an alkyl group having a number of carbon atoms of 1 to 6, $R^1$ and $R^5$ represent a hydrogen atom, $R^3$ represents a hydrogen atom and $R^2$ and $R^4$ represent a fluorine atom, an alkyl group having a number of carbon atoms of 1 to 6, an alkoxy group having a number of carbon atoms of 1 to 6, a fluoroalkoxy group having a number of carbon atoms of 1 to 6 or an aryl group having a number of carbon atoms of 6 to 20, a phosphine represented by the formula (C) in which $A^1$ and $A^2$ represent a tert-butyl group, $R^1$ and $R^5$ represent a hydrogen atom, $R^3$ represents a hydrogen atom and $R^2$ and $R^4$ represent a fluorine atom, an alkyl group having a number of carbon atoms of 1 to 6, an alkoxy group having a number of carbon atoms of 1 to 6, a fluoroalkoxy group having a number of carbon atoms of 1 to 6 or an aryl group having a number of carbon atoms of 6 to 20, a phosphine represented by the formula (C) in which $A^1$ and $A^2$ represent a cycloalkyl group having a number of carbon atoms of 6 to 8, $R^1$ and $R^5$ represent a hydrogen atom, $R^3$ represents a hydrogen atom and $R^2$ and $R^4$ represent a fluorine atom, an alkyl group having a number of carbon atoms of 1 to 6, an alkoxy group having a number of carbon atoms of 1 to 6, a fluoroalkoxy group having a number of carbon atoms of 1 to 6 or an aryl group having a number of carbon atoms of 6 to 20, a phosphine represented by the formula (C) in which $A^1$ and $A^2$ represent a cyclohexyl group, $R^1$ and $R^5$ represent a hydrogen atom, $R^3$ represents a hydrogen atom and $R^2$ and $R^4$ represent a fluorine atom, an alkyl group having a number of carbon atoms of 1 to 6, an alkoxy group having a number of carbon atoms of 1 to 6, a fluoroalkoxy group having a number of carbon atoms of 1 to 6 or an aryl group having a number of carbon atoms of 6 to 20, a phosphine represented by the formula (C) in which $A^1$ and $A^2$ represent an alkyl group having a number of carbon atoms of 1 to 6, $R^1$ represents a hydrogen atom, $R^5$ represents an alkoxy group having a number of carbon atoms of 1 to 6, $R^3$ represents a hydrogen atom and $R^2$ and $R^4$ represent a fluorine atom, an alkyl group having a number of carbon atoms of 1 to 6, an alkoxy group having a number of carbon atoms of 1 to 6, a fluoroalkoxy group having a number of carbon atoms of 1 to 6 or an aryl group having a number of carbon atoms of 6 to 20, a phosphine represented by the formula (C) in which $A^1$ and $A^2$ represent a tert-butyl group, $R^1$ represents a hydrogen atom, $R^5$ represents an alkoxy group having a number of carbon atoms of 1 to 6, $R^2$ and $R^4$ represent a hydrogen atom, $R^3$ represents a hydrogen atom and $R^2$ and $R^4$ represent a fluorine atom, an alkyl group having a number of carbon atoms of 1 to 6, an alkoxy group having a number of carbon atoms of 1 to 6, a fluoroalkoxy group having a number of carbon atoms of 1 to 6 or an aryl group having a number of carbon atoms of 6 to 20, a phosphine represented by the formula (C) in which $A^1$ and $A^2$ represent a cycloalkyl group having a number of carbon atoms of 6 to 8, $R^1$ represents a hydrogen atom, $R^5$ represents an alkoxy group having a number of carbon atoms of 1 to 6, $R^3$ represents a hydrogen atom and $R^2$ and $R^4$ represent a fluorine atom, an alkyl group having a number of carbon atoms of 1 to 6, an alkoxy group having a number of carbon atoms of 1 to 6, a fluoroalkoxy group having a number of carbon atoms of 1 to 6 or an aryl group having a number of carbon atoms of 6 to 20, a phosphine represented by the formula (C) in which $A^1$ and $A^2$ represent a cyclohexyl group, $R^1$ represents a hydrogen atom, $R^5$ represents an alkoxy group having a number of carbon atoms of 1 to 6, $R^2$ and $R^4$ represent a hydrogen atom, $R^3$ represents a hydrogen atom and $R^2$ and $R^4$ represent a fluorine atom, an alkyl group having a number of carbon atoms of 1 to 6, an alkoxy group having a number of carbon atoms of 1 to 6, a fluoroalkoxy group having a number of carbon atoms of 1 to 6 or an aryl group having a number of carbon atoms of 6 to 20, a phosphine represented by the formula (C) in which $A^1$ and $A^2$ represent an alkyl group having a number of carbon atoms of 1 to 6, $R^1$ and $R^5$ represent a hydrogen atom, $R^2$ and $R^3$ are linked to form a benzene ring together with a carbon atom to which they are linked and $R^4$ represents a hydrogen atom, a phosphine represented by the formula (C) in which $A^1$ and $A^2$ represent a tert-butyl group, $R^1$ and $R^5$ represent a hydrogen atom, $R^2$ and $R^3$ are linked to form a benzene ring together with a carbon atom to which they are linked and $R^4$ represents a hydrogen atom, a phosphine represented by the formula (C) in which $A^1$ and $A^2$ represent a cycloalkyl group having a number of carbon atoms of 6 to 8, $R^1$ and $R^5$ represent a hydrogen atom, $R^2$ and $R^3$ are linked to form a benzene ring together with a carbon atom to which they are linked and $R^4$ represents a hydrogen atom, and a phosphine represented by the formula (C) in which $A^1$ and $A^2$ represent a cyclohexyl group, $R^1$ and $R^5$ represent a hydrogen atom, $R^2$ and $R^3$ are linked to form a benzene ring together with a carbon atom to which they are linked and $R^4$ represents a hydrogen atom.

Specific examples of the phosphine represented by the formula (C) include di-(tert-butyl)(4-fluorophenyl)phosphine, di-(tert-butyl)(3-fluorophenyl)phosphine, di-(tert-butyl)(4-methylphenyl)phosphine, di-(tert-butyl)(3-methylphenyl)phosphine, di-(tert-butyl)(4-ethylphenyl)phosphine, di-(tert-butyl)(3-ethylphenyl)phosphine, di-(tert-butyl)(4-isopropylphenyl)phosphine, di-(tert-butyl)(3-isopropylphenyl)phosphine, di-(tert-butyl)(4-tert-butylphenyl)phosphine, di-(tert-butyl)(3-tert-butylphenyl)phosphine, di-(tert-butyl)(4-methoxyphenyl)phosphine, di-(tert-butyl)(3-methoxyphenyl)phosphine, di-(tert-butyl)(4-ethoxyphenyl)phosphine, di-(tert-butyl)(3-ethoxyphenyl)phosphine, di-(tert-butyl)(2-methoxyphenyl)phosphine, di-(tert-butyl)(2-ethoxyphenyl)phosphine, di-(tert-butyl)(4-trifluoromethoxyphenyl)phosphine, di-(tert-butyl)(3-trifluoromethoxyphenyl)phosphine, di-(tert-butyl)(4-pentafluoroethoxyphenyl)phosphine, di-(tert-butyl)(3-pentafluoroethoxyphenyl)phosphine, di-(tert-butyl)([1,1'-biphenyl]-4-yl)phosphine, di-(tert-butyl)([1,1'-biphenyl]-3-yl)phosphine, di-(tert-butyl)(2-naphthyl)phosphine, di-(tert-butyl)(3,5-difluorophenyl)phosphine, di-(tert-butyl)(3,5-dimethylphenyl)phosphine, di-(tert-butyl)(3,5-diethylphenyl)phosphine, di-(tert-butyl)(3,5-diisopropylphenyl)phosphine, di-(tert-butyl)(3,5-di-(tert-butyl)phenyl)phosphine, di-(tert-butyl)(3,5-dimethoxyphenyl)phosphine, di-(tert-butyl)(3,5-diethoxyphenyl)phosphine, di-(tert-butyl)(3,5-di-(trifluoromethoxy)phenyl)phosphine, di-(tert-butyl)(3,5-di-(trifluoroethoxy)phenyl)phosphine, di-(tert-butyl)((1,1':3',1"-terphenyl)-5'-yl)phosphine, dicyclohexyl(4-fluorophenyl)phosphine, dicyclohexyl(3-fluorophenyl)phosphine, dicyclohexyl(4-methylphenyl)phosphine, dicyclohexyl(3-methylphenyl)phosphine, dicyclohexyl(4-ethylphenyl)phosphine, dicyclohexyl(3-ethylphenyl)phosphine, dicyclohexyl(4-isopropylphenyl)phosphine, dicyclohexyl(3-isopropylphenyl)phosphine, dicyclohexyl(4-tert-butylphenyl)phosphine, dicyclohexyl(3-tert-butylphenyl)phosphine, dicyclohexyl(4-methoxyphenyl)phosphine, dicyclohexyl(3-methoxyphenyl)phosphine, dicyclohexyl(4-ethoxyphenyl)phosphine, dicyclohexyl(3-ethoxyphenyl)phosphine, dicyclohexyl(2-methoxyphenyl)phosphine, dicyclohexyl(2-ethoxyphenyl)phosphine, dicyclohexyl(4-trifluoromethoxyphenyl)phosphine, dicyclohexyl(3-trifluoromethoxyphenyl)phosphine, dicyclohexyl(4-pentafluoroethoxyphenyl)phosphine, dicyclohexyl(3-pentafluoroethoxyphenyl)phosphine, dicyclohexyl([1,1'-biphenyl]-4-yl)phosphine, dicyclohexyl([1,1'-biphenyl]-3-yl)phosphine, dicyclohexyl(2-naphthyl)phosphine, dicyclohexyl(3,5-difluorophenyl)phosphine, dicyclohexyl(3,5-dimethylphenyl)phosphine, dicyclohexyl(3,5-diethylphenyl)phosphine, dicyclohexyl(3,5-diisopropylphenyl)phosphine, dicyclohexyl(3,5-di-(tert-butyl)phenyl)phosphine, dicyclohexyl(3,5-dimethoxyphenyl)phosphine, dicyclohexyl(3,5-diethoxyphenyl)phosphine, dicyclohexyl(3,5-di-(trifluoromethoxy)phenyl)phosphine, dicyclohexyl(3,5-di-(trifluoroethoxy)phenyl)phosphine and dicyclohexyl((1,1':3',1"-terphenyl)-5'-yl)phosphine, and preferable are di-(tert-butyl)(4-fluorophenyl)phosphine, di-(tert-butyl)(3-fluorophenyl)phosphine, di-(tert-butyl)(4-methylphenyl)phosphine, di-(tert-butyl)(3-methylphenyl)phosphine, di-(tert-butyl)(4-ethylphenyl)phosphine, di-(tert-butyl)(3-ethylphenyl)phosphine, di-(tert-butyl)(4-isopropylphenyl)phosphine, di-(tert-butyl)(3-isopropylphenyl)phosphine, di-(tert-butyl)(4-tert-butylphenyl)phosphine, di-(tert-butyl)(3-tert-butylphenyl)phosphine, di-(tert-butyl)(4-methoxyphenyl)phosphine, di-(tert-butyl)(3-methoxyphenyl)phosphine, di-(tert-butyl)(4-ethoxyphenyl)phosphine, di-(tert-butyl)(3-ethoxyphenyl)phosphine, di-(tert-butyl)(4-trifluoromethoxyphenyl)phosphine, di-(tert-butyl)(3-trifluoromethoxyphenyl)phosphine, di-(tert-butyl)(4-pentafluoroethoxyphenyl)phosphine, di-(tert-butyl)(3-pentafluoroethoxyphenyl)phosphine, di-(tert-butyl)([1,1'-biphenyl]-4-yl)phosphine, di-(tert-butyl)([1,1'-biphenyl]-3-yl)phosphine, di-(tert-butyl)(2-naphthyl)phosphine, di-(tert-butyl)(3,5-difluorophenyl)phosphine, di-(tert-butyl)(3,5-dimethylphenyl)phosphine, di-(tert-butyl)(3,5-diethylphenyl)phosphine, di-(tert-butyl)(3,5-diisopropylphenyl)phosphine, di-(tert-butyl)(3,5-di-(tert-butyl)phenyl)phosphine, di-(tert-butyl)(3,5- dimethoxyphenyl)phosphine, di-(tert-butyl)(3,5-diethoxyphenyl)phosphine, di-(tert-butyl)(3,5-di-(trifluoromethoxy)phenyl)phosphine, di-(tert-butyl)(3,5-di-(trifluoroethoxy)phenyl)phosphine and di-(tert-butyl)((1,1':3',1''-terphenyl)-5'-yl)phosphine, more preferable are di-(tert-butyl)(3,5-difluorophenyl)phosphine, di-(tert-butyl)(3,5-dimethylphenyl)phosphine, di-(tert-butyl)(3,5-diethylphenyl)phosphine, di-(tert-butyl)(3,5-diisopropylphenyl)phosphine, di-(tert-butyl)(3,5-di-(tert-butyl)phenyl)phosphine, di-(tert-butyl)(3,5-dimethoxyphenyl)phosphine, di-(tert-butyl)(3,5-diethoxyphenyl)phosphine, di-(tert-butyl)(3,5-di-(trifluoromethoxy)phenyl)phosphine, di-(tert-butyl)(3,5-di-(trifluoroethoxy)phenyl)phosphine and di-(tert-butyl)((1,1':3',1''-terphenyl)-5'-yl)phosphine.

<Phosphonium Salt Represented by the Formula (D)>

The phosphonium salt represented by the formula (D) is represented by the following formula (D).

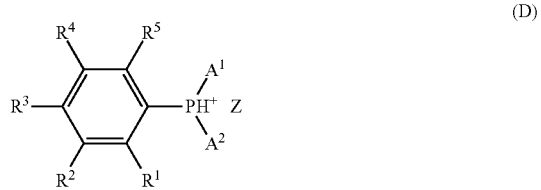

In the formula (D), $A^1$, $A^2$, $R^1$ to $R^5$ represent the same meaning as described above. Z represents an anion.

The anion represented by Z includes halogen ions such as $F^-$, $Cl^-$, $Br^-$ and $I^-$, a perchlorate ion, a hydrogen sulfate ion, a hexafluorophosphate ion, an anion represented by the formula (Y):

$[B(R^6)_4]^-$ (Y)

(wherein, $R^6$ represents an aryl group which may have a substituent, a monovalent aromatic heterocyclic group which may have a substituent, or a halogen atom.)
and the like, and an anion represented by the formula (Y) is preferable.

The aryl group which may have a substituent represented by $R^6$ includes a phenyl group, a 4-methylphenyl group, a 3-methylphenyl group, a 2-methylphenyl group, a 4-tert-butylphenyl group, a 4-fluorophenyl group, a pentafluorophenyl group and the like, preferably a phenyl group, a 4-methylphenyl group, a 4-fluorophenyl group and a pentafluorophenyl group, more preferably a phenyl group.

The monovalent aromatic heterocyclic group which may have a substituent represented by $R^6$ includes a 2-pyridyl group, a 3-pyridyl group, a 4-pyridyl group, a 4-tert-butyl-2-pyridyl group, a 2-thiophenyl group and the like, preferably a 2-pyridyl group, a 3-pyridyl group and a 4-pyridyl group, more preferably a 4-pyridyl group.

The halogen atom represented by $R^6$ includes a fluorine atom, a chlorine atom, a bromine atom and an iodine atom, preferably a fluorine atom.

As $R^6$, a phenyl group and a fluorine atom are particularly preferable, a fluorine atom is most preferable, among the above-described examples.

Specific examples of the phosphonium salt represented by the formula (D) include di-(tert-butyl)(4-fluorophenyl)phosphonium tetrafluoroborate, di-(tert-butyl)(3-fluorophenyl)phosphonium tetrafluoroborate, di-(tert-butyl)(4-methylphenyl)phosphonium tetrafluoroborate, di-(tert-butyl)(3-methylphenyl)phosphonium tetrafluoroborate, di-(tert-butyl)(4-ethylphenyl)phosphonium tetrafluoroborate, di-(tert-butyl)(3-ethylphenyl)phosphonium tetrafluoroborate, di-(tert-butyl)(4-isopropylphenyl)phosphonium tetrafluoroborate, di-(tert-butyl)(3-isopropylphenyl)phosphonium tetrafluoroborate, di-(tert-butyl)(4-tert-butylphenyl)phosphonium tetrafluoroborate, di-(tert-butyl)(3-tert-butylphenyl)phosphonium tetrafluoroborate, di-(tert-butyl)(4-methoxyphenyl)phosphonium tetrafluoroborate, di-(tert-butyl)(3-methoxyphenyl)phosphonium tetrafluoroborate, di-(tert-butyl)(4-ethoxyphenyl)phosphonium tetrafluoroborate, di-(tert-butyl)(3-ethoxyphenyl)phosphonium tetrafluoroborate, di-(tert-butyl)(2-methoxyphenyl)phosphonium tetrafluoroborate, di-(tert-butyl)(2-ethoxyphenyl)phosphonium tetrafluoroborate, di-(tert-butyl)(4-trifluoromethoxyphenyl)phosphonium tetrafluoroborate, di-(tert-butyl)(3-trifluoromethoxyphenyl)phosphonium tetrafluoroborate, di-(tert-butyl)(4-pentafluoroethoxyphenyl)phosphonium tetrafluoroborate, di-(tert-butyl)(3-pentafluoroethoxyphenyl)phosphonium tetrafluoroborate, di-(tert-butyl)([1,1'-biphenyl]-4-yl)phosphonium tetrafluoroborate, di-(tert-butyl)([1,1'-biphenyl]-3-yl)phosphonium tetrafluoroborate, di-(tert-butyl)(2-naphthyl)phosphonium tetrafluoroborate, di-(tert-butyl)(3,5-difluorophenyl)phosphonium tetrafluoroborate, di-(tert-butyl)(3,5-dimethylphenyl)phosphonium tetrafluoroborate, di-(tert-butyl)(3,5-diethylphenyl)phosphonium tetrafluoroborate, di-(tert-butyl)(3,5-diisopropylphenyl)phosphonium tetrafluoroborate, di-(tert-butyl)(3,5-di-(tert-butyl)phenyl)phosphonium tetrafluoroborate, di-(tert-butyl)(3,5-dimethoxyphenyl)phosphonium tetrafluoroborate, di-(tert-butyl)(3,5-diethoxyphenyl)phosphonium tetrafluoroborate, di-(tert-butyl)(3,5-di-(trifluoromethoxy)phenyl)phosphonium tetrafluoroborate, di-(tert-butyl)(3,5-di-(trifluoroethoxy)phenyl)phosphonium tetrafluoroborate, di-(tert-butyl)((1,1':3',1''-terphenyl)-5'-yl)phosphonium tetrafluoroborate, di-(tert-butyl)(3,5-difluorophenyl)phosphonium tetraphenyl borate, di-(tert-butyl)(3,5-dimethylphenyl)phosphonium tetraphenyl borate, di-(tert-butyl)(3,5-diethylphenyl)phosphonium tetraphenyl borate, di-(tert-butyl)(3,5-diisopropylphenyl)phosphonium tetraphenyl borate, di-(tert-butyl)(3,5-di-(tert-butyl)phenyl)phosphonium tetraphenyl borate, di-(tert-butyl)(3,5-dimethoxyphenyl)phosphonium tetraphenyl borate, di-(tert-butyl)(3,5-diethoxyphenyl)phosphonium tetraphenyl borate, di-(tert-butyl)(3,5-di-(trifluoromethoxy)phenyl)phosphonium tetraphenyl borate, di-(tert-butyl)(3,5-di-(trifluoroethoxy)phenyl)phosphonium tetraphenyl borate, di-(tert-butyl)((1,1':3',1''-terphenyl)-5'-yl)phosphonium tetraphenyl borate, di-(tert-butyl)(3,5-difluorophenyl)phosphonium tetramesityl borate, di-(tert-butyl)(3,5-dimethylphenyl)phosphonium tetramesityl borate, di-(tert-butyl)(3,5-diethylphenyl)phosphonium tetramesityl borate, di-(tert-butyl)(3,5-diisopropylphenyl)phosphonium tetramesityl borate, di-(tert-butyl)(3,5-di-(tert-butyl)phenyl)phosphonium tetramesityl borate, di-(tert-butyl)(3,5-dimethoxyphenyl)phosphonium tetramesityl borate, di-(tert-butyl)(3,5-diethoxyphenyl)phosphonium tetramesityl borate, di-(tert-butyl)(3,5-di-(trifluoromethoxy)phenyl)phosphonium tetramesityl borate, di-(tert-butyl)(3,5-di-(trifluoroethoxy)phenyl)phosphonium tetramesityl borate, di-(tert-butyl)((1,1':3',1''-terphenyl)-5'-yl)phosphonium tetramesityl borate, dicyclohexyl(4-fluorophenyl)phosphonium tetrafluoroborate, dicyclohexyl(3-fluorophenyl)phosphonium tetrafluoroborate, dicyclohexyl(4-methylphenyl)phosphonium tetrafluoroborate, dicyclohexyl(3-methylphenyl)phosphonium tetrafluoroborate, dicyclohexyl(4-ethylphenyl)phosphonium tetrafluoroborate, dicyclohexyl(3-ethylphenyl)phosphonium tetrafluoroborate, dicyclohexyl(4-isopropylphenyl)phosphonium tetrafluoroborate, dicyclohexyl(3-isopropylphenyl)phosphonium tetrafluoroborate, dicyclohexyl(4-tert-butylphenyl)phosphonium tetrafluoroborate, dicyclohexyl(3-tert-butylphenyl)phosphonium tetrafluoroborate, dicyclohexyl(4-methoxyphenyl)phosphonium tetrafluoroborate, dicyclohexyl(3-methoxyphenyl)phosphonium tetrafluoroborate, dicyclohexyl(4-ethoxyphenyl)phosphonium tetrafluoroborate, dicyclohexyl(3-ethoxyphenyl)phosphonium tetrafluoroborate, dicyclohexyl(2-methoxyphenyl)phosphonium tetrafluoroborate, dicyclohexyl(2-ethoxyphenyl)phosphonium tetrafluoroborate, dicyclohexyl(4-trifluoromethoxyphenyl)phosphonium tetrafluoroborate, dicyclohexyl(3-trifluoromethoxyphenyl)phosphonium tetrafluoroborate, dicyclohexyl(4-pentafluoroethoxyphenyl)phosphonium tetrafluoroborate, dicyclohexyl(3-pentafluoroethoxyphenyl)phosphonium tetrafluoroborate, dicyclohexyl([1,1'-biphenyl]-4-yl)phosphonium tetrafluoroborate, dicyclohexyl([1,1'-biphenyl]-3-yl)phosphonium tetrafluoroborate, dicyclohexyl(2-naphthylphosphonium tetrafluoroborate, dicyclohexyl(3,5-difluorophenyl)phosphonium tetrafluoroborate, dicyclohexyl(3,5-dimethylphenyl)phosphonium tetrafluoroborate, dicyclohexyl(3,5-diethylphenyl)phosphonium tetrafluoroborate, dicyclohexyl(3,5-diisopropylphenyl)phosphonium tetrafluoroborate, dicyclohexyl(3,5-di-(tert-butyl)phenyl)phosphonium tetrafluoroborate, dicyclohexyl(3,5-dimethoxyphenyl)phosphonium tetrafluoroborate, dicyclohexyl(3,5-diethoxyphenyl)phosphonium tetrafluoroborate, dicyclohexyl(3,5-di-(trifluoromethoxy)phenyl)phosphonium tetrafluoroborate, dicyclohexyl(3,5-di-(trifluoroethoxy)phenyl)phosphonium tetrafluoroborate and dicyclohexyl((1,1':3',1"-terphenyl)-5'-yl)phosphonium tetrafluoroborate, dicyclohexyl(3,5-difluorophenyl)phosphonium tetraphenyl borate, dicyclohexyl(3,5-dimethylphenyl)phosphonium tetraphenyl borate, dicyclohexyl(3,5-diethylphenyl)phosphonium tetraphenyl borate, dicyclohexyl(3,5-diisopropylphenyl)phosphonium tetraphenyl borate, dicyclohexyl(3,5-di-(tert-butyl)phenyl)phosphonium tetraphenyl borate, dicyclohexyl(3,5-dimethoxyphenyl)phosphonium tetraphenyl borate, dicyclohexyl(3,5-diethoxyphenyl)phosphonium tetraphenyl borate, dicyclohexyl(3,5-di-(trifluoromethoxy)phenyl)phosphonium tetraphenyl borate, dicyclohexyl(3,5-di-(trifluoroethoxy)phenyl)phosphonium tetraphenyl borate and dicyclohexyl((1,1':3',1"-terphenyl)-5'-yl)phosphonium tetraphenyl borate, dicyclohexyl(3,5-difluorophenyl)phosphonium tetramesityl borate, dicyclohexyl(3,5-dimethylphenyl)phosphonium tetramesityl borate, dicyclohexyl(3,5-diethylphenyl)phosphonium tetramesityl borate, dicyclohexyl(3,5-diisopropylphenyl)phosphonium tetramesityl borate, dicyclohexyl(3,5-di-(tert-butyl)phenyl)phosphonium tetramesityl borate, dicyclohexyl(3,5-dimethoxyphenyl)phosphonium tetramesityl borate, dicyclohexyl(3,5-diethoxyphenyl)phosphonium tetramesityl borate, dicyclohexyl(3,5-di-(trifluoromethoxy)phenyl)phosphonium tetramesityl borate, dicyclohexyl(3,5-di-(trifluoroethoxy)phenyl)phosphonium tetramesityl borate and dicyclohexyl((1,1':3',1"-terphenyl)-5'-yl)phosphonium tetramesityl borate, and preferable are di-(tert-butyl)(4-fluorophenyl)phosphonium tetrafluoroborate, di-(tert-butyl)(3-fluorophenyl-phosphonium tetrafluoroborate, di-(tert-butyl)(4-methylphenyl)phosphonium tetrafluoroborate, di-(tert-butyl)(3-methylphenyl)phosphonium tetrafluoroborate, di-(tert-butyl)(4-ethylphenyl)phosphonium tetrafluoroborate, di-(tert-butyl)(3-ethylphenyl)phosphonium tetrafluoroborate, di-(tert-butyl)(4-isopropylphenyl)phosphonium tetrafluoroborate, di-(tert-butyl)(3-isopropylphenyl)phosphonium tetrafluoroborate, di-(tert-butyl)(4-tert-butylphenyl)phosphonium tetrafluoroborate, di-(tert-butyl)(3-tert-butylphenyl)phosphonium tetrafluoroborate, di-(tert-butyl)(4-methoxyphenyl)phosphonium tetrafluoroborate, di-(tert-butyl)(3-methoxyphenyl)phosphonium tetrafluoroborate, di-(tert-butyl)(4-ethoxyphenyl)phosphonium tetrafluoroborate, di-(tert-butyl)(3-ethoxyphenyl)phosphonium tetrafluoroborate, di-(tert-butyl)(2-methoxyphenyl)phosphonium tetrafluoroborate, di-(tert-butyl)(2-ethoxyphenyl)phosphonium tetrafluoroborate, di-(tert-butyl)(4-trifluoromethoxyphenyl)phosphonium tetrafluoroborate, di-(tert-butyl)(3-trifluoromethoxyphenyl)phosphonium tetrafluoroborate, di-(tert-butyl)(4-pentafluoroethoxyphenyl)phosphonium tetrafluoroborate, di-(tert-butyl)(3-pentafluoroethoxyphenyl)phosphonium tetrafluoroborate, di-(tert-butyl)([1,1'-biphenyl]-4-yl)phosphonium tetrafluoroborate, di-(tert-butyl)([1,1'-biphenyl]-3-yl)phosphonium tetrafluoroborate, di-(tert-butyl)(2-naphthyl)phosphonium tetrafluoroborate, di-(tert-butyl)(3,5-difluorophenyl)phosphonium tetrafluoroborate, di-(tert-butyl)(3,5-dimethylphenyl)phosphonium tetrafluoroborate, di-(tert-butyl)(3,5-diethylphenyl)phosphonium tetrafluoroborate, di-(tert-butyl)(3,5-diisopropylphenyl)phosphonium tetrafluoroborate, di-(tert-butyl)(3,5-di-(tert-butyl)phenyl)phosphonium tetrafluoroborate, di-(tert-butyl)(3,5-dimethoxyphenyl)phosphonium tetrafluoroborate, di-(tert-butyl)(3,5-diethoxyphenyl)phosphonium tetrafluoroborate, di-(tert-butyl)(3,5-di-(trifluoromethoxy)phenyl)phosphonium tetrafluoroborate, di-(tert-butyl)(3,5-di-(trifluoroethoxy)phenyl)phosphonium tetrafluoroborate, di-(tert-butyl)((1,1':3',1"-terphenyl)-5'-yl)phosphonium tetrafluoroborate, di-(tert-butyl)(3,5-difluorophenyl)phosphonium tetraphenyl borate, di-(tert-butyl)(3,5-dimethylphenyl)phosphonium tetraphenyl borate, di-(tert-butyl)(3,5-diethylphenyl)phosphonium tetraphenyl borate, di-(tert-butyl)(3,5-diisopropylphenyl)phosphonium tetraphenyl borate, di-(tert-butyl)(3,5-di-(tert-butyl)phenyl)phosphonium tetraphenyl borate, di-(tert-butyl)(3,5-dimethoxyphenyl)phosphonium tetraphenyl borate, di-(tert-butyl)(3,5-diethoxyphenyl)phosphonium tetraphenyl borate, di-(tert-butyl)(3,5-di-(trifluoromethoxy)phenyl)phosphonium tetraphenyl borate, di-(tert-butyl)(3,5-di-(trifluoroethoxy)phenyl)phosphonium tetraphenyl borate, di-(tert-butyl)((1,1':3',1"-terphenyl)-5'-yl)phosphonium tetraphenyl borate, di-(tert-butyl)(3,5-difluorophenyl)phosphonium tetramesityl borate, di-(tert-butyl)(3,5-dimethylphenyl)phosphonium tetramesityl borate, di-(tert-butyl)(3,5-diethylphenyl)phosphonium tetramesityl borate, di-(tert-butyl)(3,5-diisopropylphenyl)phosphonium tetramesityl borate, di-(tert-butyl)(3,5-di-(tert-butyl)phenyl)phosphonium tetramesityl borate, di-(tert-butyl)(3,5-dimethoxyphenyl)phosphonium tetramesityl borate, di-(tert-butyl)(3,5-diethoxyphenyl)phosphonium tetramesityl borate, di-(tert-butyl)(3,5-di-(trifluoromethoxy)phenyl)phosphonium tetramesityl borate, di-(tert-butyl)(3,5-di-(trifluoroethoxy)phenyl)phosphonium tetramesityl borate and di-(tert-butyl)((1,1':3',1"-terphenyl)-5'-yl)phosphonium tetramesityl borate, more preferable are di-(tert-butyl)(3,5-difluorophenyl)phosphonium tetrafluoroborate, di-(tert-butyl)(3,5-dimethylphenyl)phosphonium tetrafluoroborate, di-(tert-butyl)(3,5-diethylphenyl)phosphonium tetrafluoroborate, di-(tert-butyl)(3,5-diisopropylphenyl)phosphonium tetrafluoroborate, di-(tert-butyl)(3,5-di-(tert-butyl)phenyl)phosphonium tetrafluoroborate, di-(tert-butyl)(3,5-dimethoxyphenyl)phosphonium tetrafluoroborate, di-(tert-butyl)

(3,5-diethoxyphenyl)phosphonium tetrafluoroborate, di-(tert-butyl)(3,5-di-(trifluoromethoxy)phenyl)phosphonium tetrafluoroborate, di-(tert-butyl)(3,5-di-(trifluoroethoxy)phenyl)phosphonium tetrafluoroborate, di-(tert-butyl)((1,1':3',1''-terphenyl)-5'-yl)phosphonium tetrafluoroborate, di-(tert-butyl)(3,5-difluorophenyl)phosphonium tetraphenyl borate, di-(tert-butyl)(3,5-dimethylphenyl)phosphonium tetraphenyl borate, di-(tert-butyl)(3,5-diethylphenyl)phosphonium tetraphenyl borate, di-(tert-butyl)(3,5-diisopropylphenyl)phosphonium tetraphenyl borate, di-(tert-butyl)(3,5-di-(tert-butyl)phenyl)phosphonium tetraphenyl borate, di-(tert-butyl)(3,5-dimethoxyphenyl)phosphonium tetraphenyl borate, di-(tert-butyl)(3,5-diethoxyphenyl)phosphonium tetraphenyl borate, di-(tert-butyl)(3,5-di-(trifluoromethoxy)phenyl)phosphonium tetraphenyl borate, di-(tert-butyl)(3,5-di-(trifluoroethoxy)phenyl)phosphonium tetraphenyl borate, di-(tert-butyl)((1,1':3',1''-terphenyl)-5'-yl)phosphonium tetraphenyl borate, di-(tert-butyl)(3,5-difluorophenyl)phosphonium tetramesityl borate, di-(tert-butyl)(3,5-dimethylphenyl)phosphonium tetramesityl borate, di-(tert-butyl)(3,5-diethylphenyl)phosphonium tetramesityl borate, di-(tert-butyl)(3,5-diisopropylphenyl)phosphonium tetramesityl borate, di-(tert-butyl)(3,5-di-(tert-butyl)phenyl)phosphonium tetramesityl borate, di-(tert-butyl)(3,5-dimethoxyphenyl)phosphonium tetramesityl borate, di-(tert-butyl)(3,5-diethoxyphenyl)phosphonium tetramesityl borate, di-(tert-butyl)(3,5-di-(trifluoromethoxy)phenyl)phosphonium tetramesityl borate, di-(tert-butyl)(3,5-di-(trifluoroethoxy)phenyl)phosphonium tetramesityl borate and di-(tert-butyl)((1,1':3',1''-terphenyl)-5'-yl)phosphonium tetramesityl borate.

<Phosphine Represented by the Formula (E)>

The phosphine represented by the formula (C) is preferably a phosphine represented by the formula (E).

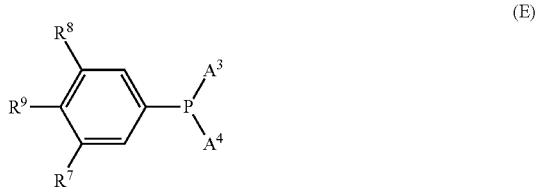

(E)

In the formula (E), $A^3$ and $A^4$ represent each independently an alkyl group having a number of carbon atoms of 1 to 20 or a saturated alicyclic hydrocarbon group having a number of carbon atoms of 6 to 20.

$A^3$ and $A^4$ may be the same or different. Preferably, $A^3$ and $A^4$ are the same.

The alkyl group having a number of carbon atoms of 1 to 20 includes the same groups as described above.

In the formula (E), $R^7$ and $R^8$ represent each independently a fluorine atom, an alkyl group having a number of carbon atoms of 1 to 20, a cycloalkyl group having a number of carbon atoms of 3 to 20, an alkoxy group having a number of carbon atoms of 1 to 20, a cycloalkoxy group having a number of carbon atoms of 3 to 20, a fluoroalkoxy group having a number of carbon atoms of 1 to 20, a fluorocycloalkoxy group having a number of carbon atoms of 3 to 30 or an aryl group having a number of carbon atoms of 6 to 20, and $R^9$ represents a hydrogen atom, a fluorine atom, an alkyl group having a number of carbon atoms of 1 to 20, a cycloalkyl group having a number of carbon atoms of 3 to 20, an alkoxy group having a number of carbon atoms of 1 to 20, a cycloalkoxy group having a number of carbon atoms of 3 to 20, a fluoroalkoxy group having a number of carbon atoms of 1 to 20 or an aryl group having a number of carbon atoms of 6 to 20.

The alkyl group having a number of carbon atoms of 1 to 20, the cycloalkyl group having a number of carbon atoms of 3 to 20, the alkoxy group having a number of carbon atoms of 1 to 20, the cycloalkoxy group having a number of carbon atoms of 3 to 20, the fluoroalkoxy group having a number of carbon atoms of 1 to 20, the fluorocycloalkoxy group having a number of carbon atoms of 3 to 30 and the aryl group having a number of carbon atoms of 6 to 20 include the same groups as described above.

It is preferable that $R^7$ and $R^8$ represent each independently a fluorine atom, an alkyl group having a number of carbon atoms of 1 to 20, an alkoxy group having a number of carbon atoms of 1 to 20, a fluoroalkoxy group having a number of carbon atoms of 1 to 20 or an aryl group having a number of carbon atoms of 6 to 20, it is more preferable that $R^7$ and $R^8$ represent each independently a fluorine atom, an alkyl group having a number of carbon atoms of 1 to 6, an alkoxy group having a number of carbon atoms of 1 to 6, a fluoroalkoxy group having a number of carbon atoms of 1 to 6 or an aryl group having a number of carbon atoms of 6 to 20, it is most preferable that $R^7$ and $R^8$ represent each independently an alkyl group having a number of carbon atoms of 1 to 6 or an aryl group having a number of carbon atoms of 6 to 20.

It is preferable that $R^9$ represents a hydrogen atom, a fluorine atom, an alkyl group having a number of carbon atoms of 1 to 20, an alkoxy group having a number of carbon atoms of 1 to 20, a fluoroalkoxy group having a number of carbon atoms of 1 to 20 or an aryl group having a number of carbon atoms of 6 to 20, it is more preferable that $R^9$ represents a hydrogen atom, a fluorine atom, an alkyl group having a number of carbon atoms of 1 to 6, an alkoxy group having a number of carbon atoms of 1 to 6, a fluoroalkoxy group having a number of carbon atoms of 1 to 6 or an aryl group having a number of carbon atoms of 6 to 20, it is most preferable that $R^9$ represents a hydrogen atom.

The phosphine represented by the formula (E) includes
a phosphine represented by the formula (E) in which $A^3$ and $A^4$ represent an alkyl group having a number of carbon atoms of 1 to 6,
a phosphine represented by the formula (E) in which $A^3$ and $A^4$ represent a tert-butyl group,
a phosphine represented by the formula (E) in which $A^3$ and $A^4$ represent a cycloalkyl group having a number of carbon atoms of 6 to 8,
a phosphine represented by the formula (E) in which $A^3$ and $A^4$ represent a cyclohexyl group,
a phosphine represented by the formula (E) in which $R^7$ and $R^8$ represent a fluorine atom, an alkyl group having a number of carbon atoms of 1 to 6, an alkoxy group having a number of carbon atoms of 1 to 6, a fluoroalkoxy group having a number of carbon atoms of 1 to 6 or an aryl group having a number of carbon atoms of 6 to 20,
a phosphine represented by the formula (E) in which $R^7$ and $R^8$ represent an alkyl group having a number of carbon atoms of 1 to 6 or an aryl group having a number of carbon atoms of 6 to 20,
a phosphine represented by the formula (E) in which $R^9$ represents a hydrogen atom,
a phosphine represented by the formula (E) in which $A^3$ and $A^4$ represent an alkyl group having a number of carbon atoms of 1 to 6 and $R^7$ and $R^8$ represent a fluorine atom, an alkyl group having a number of carbon atoms of 1 to 6, an alkoxy group having a number of carbon atoms of 1 to 6, a fluoroalkoxy group having a number of carbon atoms of 1 to 6 or an aryl group having a number of carbon atoms of 6 to 20, a phosphine represented by the formula (E) in which $A^3$ and $A^4$ represent an alkyl group having a number of carbon atoms of 1 to 6 and $R^7$ and $R^8$ represent an alkyl group having a number of carbon atoms of 1 to 6 or an aryl group having a number of carbon atoms of 6 to 20, a phosphine represented by the formula (E) in which $A^3$ and $A^4$ represent an alkyl group having a number of carbon atoms of 1 to 6, $R^7$ and $R^8$ represent an alkyl group having a number of carbon atoms of 1 to 6 or an aryl group having a number of carbon atoms of 6 to 20 and $R^9$ represents a hydrogen atom, a phosphine represented by the formula (E) in which $A^3$ and $A^4$ represent a tert-butyl group and $R^7$ and $R^8$ represent a fluorine atom, an alkyl group having a number of carbon atoms of 1 to 6, an alkoxy group having a number of carbon atoms of 1 to 6, a fluoroalkoxy group having a number of carbon atoms of 1 to 6 or an aryl group having a number of carbon atoms of 6 to 20, a phosphine represented by the formula (E) in which $A^3$ and $A^4$ represent a tert-butyl group and $R^7$ and $R^8$ represent an alkyl group having a number of carbon atoms of 1 to 6 or an aryl group having a number of carbon atoms of 6 to 20, a phosphine represented by the formula (E) in which $A^3$ and $A^4$ represent a tert-butyl group, $R^7$ and $R^8$ represent an alkyl group having a number of carbon atoms of 1 to 6 or an aryl group having a number of carbon atoms of 6 to 20 and $R^9$ represents a hydrogen atom, a phosphine represented by the formula (E) in which $A^3$ and $A^4$ represent a cycloalkyl group having a number of carbon atoms of 6 to 8 and $R^7$ and $R^8$ represent a fluorine atom, an alkyl group having a number of carbon atoms of 1 to 6, an alkoxy group having a number of carbon atoms of 1 to 6, a fluoroalkoxy group having a number of carbon atoms of 1 to 6 or an aryl group having a number of carbon atoms of 6 to 20, a phosphine represented by the formula (E) in which $A^3$ and $A^4$ represent a cycloalkyl group having a number of carbon atoms of 6 to 8 and $R^7$ and $R^8$ represent an alkyl group having a number of carbon atoms of 1 to 6 or an aryl group having a number of carbon atoms of 6 to 20, a phosphine represented by the formula (E) in which $A^3$ and $A^4$ represent a cycloalkyl group having a number of carbon atoms of 6 to 8, $R^7$ and $R^8$ represent an alkyl group having a number of carbon atoms of 1 to 6 or an aryl group having a number of carbon atoms of 6 to 20 and $R^9$ represents a hydrogen atom, a phosphine represented by the formula (E) in which $A^3$ and $A^4$ represent a cyclohexyl group and $R^7$ and $R^8$ represent a fluorine atom, an alkyl group having a number of carbon atoms of 1 to 6, an alkoxy group having a number of carbon atoms of 1 to 6, a fluoroalkoxy group having a number of carbon atoms of 1 to 6 or an aryl group having a number of carbon atoms of 6 to 20, a phosphine represented by the formula (E) in which $A^3$ and $A^4$ represent a cyclohexyl group and $R^7$ and $R^8$ represent an alkyl group having a number of carbon atoms of 1 to 6 or an aryl group having a number of carbon atoms of 6 to 20, and a phosphine represented by the formula (E) in which $A^3$ and $A^4$ represent a cyclohexyl group, $R^7$ and $R^8$ represent an alkyl group having a number of carbon atoms of 1 to 6 or an aryl group having a number of carbon atoms of 6 to 20 and $R^9$ represents a hydrogen atom.

Specific examples of the phosphine represented by the formula (E) include di-(tert-butyl)(3,5-difluorophenyl)phosphine, di-(tert-butyl)(3,5-dimethylphenyl)phosphine, di-(tert-butyl)(3,5-diethylphenyl)phosphine, di-(tert-butyl)(3,5-diisopropylphenyl)phosphine, di-(tert-butyl)(3,5-di-(tert-butyl)phenyl)phosphine, di-(tert-butyl)(3,5-dimethoxyphenyl)phosphine, di-(tert-butyl)(3,5-diethoxyphenyl)phosphine, di-(tert-butyl)(3,5-di-(trifluoromethoxy)phenyl)phosphine, di-(tert-butyl)(3,5-di-(trifluoroethoxy)phenyl)phosphine, di-(tert-butyl)((1,1':3',1''-terphenyl)-5'-yl)phosphine, dicyclohexyl(3,5-difluorophenyl)phosphine, dicyclohexyl(3,5-dimethylphenyl)phosphine, dicyclohexyl(3,5-diethylphenyl)phosphine, dicyclohexyl(3,5-diisopropylphenyl)phosphine, dicyclohexyl(3,5-di-(tert-butyl)phenyl)phosphine, dicyclohexyl(3,5-dimethoxyphenyl)phosphine, dicyclohexyl(3,5-diethoxyphenyl)phosphine, dicyclohexyl(3,5-di-(trifluoromethoxy)phenyl)phosphine, dicyclohexyl(3,5-di-(trifluoroethoxy)phenyl)phosphine and dicyclohexyl((1,1':3',1''-terphenyl)-5'-yl)phosphine, and preferable are di-(tert-butyl)(3,5-difluorophenyl)phosphine, di-(tert-butyl)(3,5-dimethylphenyl)phosphine, di-(tert-butyl)(3,5-diethylphenyl)phosphine, di-(tert-butyl)(3,5-diisopropylphenyl)phosphine, di-(tert-butyl)(3,5-di-(tert-butyl)phenyl)phosphine, di-(tert-butyl)(3,5-dimethoxyphenyl)phosphine, di-(tert-butyl)(3,5-diethoxyphenyl)phosphine, di-(tert-butyl)(3,5-di-(trifluoromethoxy)phenyl)phosphine, di-(tert-butyl)(3,5-di-(trifluoroethoxy)phenyl)phosphine and di-(tert-butyl)((1,1':3',1''-terphenyl)-5'-yl)phosphine.

The phosphonium salt represented by the formula (D) is preferably a phosphonium salt represented by the formula (F).

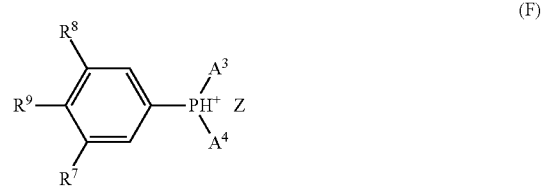

(F)

In the formula (F), $A^3$, $A^4$, $R^7$, $R^8$, $R^9$ and Z represent the same meaning as described above.

Specific examples of the phosphonium salt represented by the formula (F) include di-(tert-butyl)(3,5-difluorophenyl)phosphonium tetrafluoroborate, di-(tert-butyl)(3,5-dimethylphenyl)phosphonium tetrafluoroborate, di-(tert-butyl)(3,5-diethylphenyl)phosphonium tetrafluoroborate, di-(tert-butyl)(3,5-diisopropylphenyl)phosphonium tetrafluoroborate, di-(tert-butyl)(3,5-di-(tert-butyl)phenyl)phosphonium tetrafluoroborate, di-(tert-butyl)(3,5-dimethoxyphenyl)phosphonium tetrafluoroborate, di-(tert-butyl)(3,5-diethoxyphenyl)phosphonium tetrafluoroborate, di-(tert-butyl)(3,5-di-(trifluoromethoxy)phenyl)phosphonium tetrafluoroborate, di-(tert-butyl)(3,5-di-(trifluoroethoxy)phenyl)phosphonium tetrafluoroborate, di-(tert-butyl)((1,1':3',1''-terphenyl)-5'-yl)phosphonium tetrafluoroborate, di-(tert-butyl)(3,5-difluorophenyl)phosphonium tetraphenyl borate, di-(tert-butyl)(3,5-dimethylphenyl)phosphonium tetraphenyl borate, di-(tert-butyl)(3,5-diethylphenyl)phosphonium tetraphenyl borate, di-(tert-butyl)(3,5-diisopropylphenyl)phosphonium tetraphenyl borate, di-(tert-butyl)(3,5-di-(tert-butyl)phenyl)phosphonium tetraphenyl borate, di-(tert-butyl)(3,5-dimethoxyphenyl)phosphonium tetraphenyl borate, di-(tert-butyl)(3,5-diethoxyphenyl)phosphonium tetraphenyl borate, di-(tert-butyl)(3,5-di-(trifluoromethoxy)phenyl)phosphonium tetraphenyl borate, di-(tert-butyl)(3,5-di-(trifluoroethoxy)phenyl)phosphonium tetraphenyl borate, di-(tert-butyl)((1,1':3',1''-terphenyl)-5'-yl)phosphonium tetraphenyl borate, di-(tert-butyl)(3,5-difluorophenyl)phosphonium tetramesityl borate, di-(tert-butyl)(3,5-dimethylphenyl)phosphonium tetramesityl borate, di-(tert-butyl)(3,5-diethylphenyl)phosphonium tetramesityl borate, di-(tert-butyl)(3,5-diisopropylphenyl)phosphonium tetramesityl borate, di-(tert-butyl)(3,5-di-(tert-butyl)phenyl)phosphonium tetramesityl borate, di-(tert-butyl)(3,5-dimethoxyphenyl)phosphonium tetramesityl borate, di-(tert-butyl)(3,5-diethoxyphenyl)phosphonium tetramesityl borate, di-(tert-butyl)(3,5-di-(trifluoromethoxy)phenyl)phosphonium tetramesityl borate, di-(tert-butyl)(3,5-di-(trifluoroethoxy)phenyl)phosphonium tetramesityl borate, di-(tert-butyl)((1,1':3',1''-terphenyl)-5'-yl)phosphonium tetramesityl borate, dicyclohexyl(3,5-difluorophenyl)phosphonium tetrafluoroborate, dicyclohexyl(3,5-dimethylphenyl)phosphonium tetrafluoroborate, dicyclohexyl(3,5-diethylphenyl)phosphonium tetrafluoroborate, dicyclohexyl(3,5-diisopropylphenyl)phosphonium tetrafluoroborate, dicyclohexyl(3,5-di-(tert-butyl)phenyl)phosphonium tetrafluoroborate, dicyclohexyl(3,5-dimethoxyphenyl)phosphonium tetrafluoroborate, dicyclohexyl(3,5-diethoxyphenyl)phosphonium tetrafluoroborate, dicyclohexyl(3,5-di-(trifluoromethoxy)phenyl)phosphonium tetrafluoroborate, dicyclohexyl(3,5-di-(trifluoroethoxy)phenyl)phosphonium tetrafluoroborate and dicyclohexyl((1,1':3',1''-terphenyl)-5'-yl)phosphonium tetrafluoroborate, dicyclohexyl(3,5-difluorophenyl)phosphonium tetraphenyl borate, dicyclohexyl(3,5-dimethylphenyl)phosphonium tetraphenyl borate, dicyclohexyl(3,5-diethylphenyl)phosphonium tetraphenyl borate, dicyclohexyl(3,5-diisopropylphenyl)phosphonium tetraphenyl borate, dicyclohexyl(3,5-di-(tert-butyl)phenyl)phosphonium tetraphenyl borate, dicyclohexyl(3,5-dimethoxyphenyl)phosphonium tetraphenyl borate, dicyclohexyl(3,5-diethoxyphenyl)phosphonium tetraphenyl borate, dicyclohexyl(3,5-di-(trifluoromethoxy)phenyl)phosphonium tetraphenyl borate, dicyclohexyl(3,5-di-(trifluoroethoxy)phenyl)phosphonium tetraphenyl borate, and dicyclohexyl((1,1':3',1''-terphenyl)-5'-yl)phosphonium tetraphenyl borate, dicyclohexyl(3,5-difluorophenyl)phosphonium tetramesityl borate, dicyclohexyl(3,5-dimethylphenyl)phosphonium tetramesityl borate, dicyclohexyl(3,5-diethylphenyl)phosphonium tetramesityl borate, dicyclohexyl(3,5-diisopropylphenyl)phosphonium tetramesityl borate, dicyclohexyl(3,5-di-(tert-butyl)phenyl)phosphonium tetramesityl borate, dicyclohexyl(3,5-dimethoxyphenyl)phosphonium tetramesityl borate, dicyclohexyl(3,5-diethoxyphenyl)phosphonium tetramesityl borate, dicyclohexyl(3,5-di-(trifluoromethoxy)phenyl)phosphonium tetramesityl borate, dicyclohexyl(3,5-di-(trifluoroethoxy)phenyl)phosphonium tetramesityl borate and dicyclohexyl((1,1':3',1''-terphenyl)-5'-yl)phosphonium tetramesityl borate, and preferable are di-(tert-butyl)(3,5-difluorophenyl)phosphonium tetrafluoroborate, di-(tert-butyl)(3,5-dimethylphenyl)phosphonium tetrafluoroborate, di-(tert-butyl)(3,5-diethylphenyl)phosphonium tetrafluoroborate, di-(tert-butyl)(3,5-diisopropylphenyl)phosphonium tetrafluoroborate, di-(tert-butyl)(3,5-di-(tert-butyl)phenyl)phosphonium tetrafluoroborate, di-(tert-butyl)(3,5-dimethoxyphenyl)phosphonium tetrafluoroborate, di-(tert-butyl)(3,5-diethoxyphenyl)phosphonium tetrafluoroborate, di-(tert-butyl)(3,5-di-(trifluoromethoxy)phenyl)phosphonium tetrafluoroborate, di-(tert-butyl)(3,5-di-(trifluoroethoxy)phenyl)phosphonium tetrafluoroborate, di-(tert-butyl)((1,1':3',1''-terphenyl)-5'-yl)phosphonium tetrafluoroborate, di-(tert-butyl)(3,5-difluorophenyl)phosphonium tetraphenyl borate, di-(tert-butyl)(3,5-dimethylphenyl)phosphonium tetraphenyl borate, di-(tert-butyl)(3,5-diethylphenyl)phosphonium tetraphenyl borate, di-(tert-butyl)(3,5-diisopropylphenyl)phosphonium tetraphenyl borate, di-(tert-butyl)(3,5-di-(tert-butyl)phenyl)phosphonium tetraphenyl borate, di-(tert-butyl)(3,5-dimethoxyphenyl)phosphonium tetraphenyl borate, di-(tert-butyl)(3,5-diethoxyphenyl)phosphonium tetraphenyl borate, di-(tert-butyl)(3,5-di-(trifluoromethoxy)phenyl)phosphonium tetraphenyl borate, di-(tert-butyl)(3,5-di-(trifluoroethoxy)phenyl)phosphonium tetraphenyl borate, di-(tert-butyl)((1,1':3',1''-terphenyl)-5'-yl)phosphonium tetraphenyl borate, di-(tert-butyl)(3,5-difluorophenyl)phosphonium tetramesityl borate, di-(tert-butyl)(3,5-dimethylphenyl)phosphonium tetramesityl borate, di-(tert-butyl)(3,5-diethylphenyl)phosphonium tetramesityl borate, di-(tert-butyl)(3,5-diisopropylphenyl)phosphonium tetramesityl borate, di-(tert-butyl)(3,5-di-(tert-butyl)phenyl)phosphonium tetramesityl borate, di-(tert-butyl)(3,5-dimethoxyphenyl)phosphonium tetramesityl borate, di-(tert-butyl)(3,5-diethoxyphenyl)phosphonium tetramesityl borate, di-(tert-butyl)(3,5-di-(trifluoromethoxy)phenyl)phosphonium tetramesityl borate, di-(tert-butyl)(3,5-di-(trifluoroethoxy)phenyl)phosphonium tetramesityl borate and di-(tert-butyl)((1,1':3',1''-terphenyl)-5'-yl)phosphonium tetramesityl borate, more preferable are di-(tert-butyl)(3,5-difluorophenyl)phosphonium tetrafluoroborate, di-(tert-butyl)(3,5-dimethylphenyl)phosphonium tetrafluoroborate, di-(tert-butyl)(3,5-diethylphenyl)phosphonium tetrafluoroborate, di-(tert-butyl)(3,5-diisopropylphenyl)phosphonium tetrafluoroborate, di-(tert-butyl)(3,5-di-(tert-butyl)phenyl)phosphonium tetrafluoroborate, di-(tert-butyl)(3,5-dimethoxyphenyl)phosphonium tetrafluoroborate, di-(tert-butyl)(3,5-diethoxyphenyl)phosphonium tetrafluoroborate, di-(tert-butyl)(3,5-di-(trifluoromethoxy)phenyl)phosphonium tetrafluoroborate, di-(tert-butyl)(3,5-di-(trifluoroethoxy)phenyl)phosphonium tetrafluoroborate and di-(tert-butyl)((1,1':3',1''-terphenyl)-5'-yl)phosphonium tetrafluoroborate.

The at least one phosphine compound selected from the group consisting of a phosphine represented by the formula (C) and a phosphonium salt represented by the formula (D) is preferably a phosphine represented by the formula (C).

The use amount of the above-described phosphine compound is usually in the range of 0.1 mol to 10 mol, preferably in the range of 0.5 mol to 5 mol with respect to 1 mol of a palladium compound.

The phosphine represented by the formula (C) can be synthesized according to known methods described in Journal of Molecular Catalysis A: Chemical 2003, 200, 81-94, and the like. Further, commercially available phosphines represented by the formula (C) can also be used.

The phosphonium salt represented by the formula (D) can be synthesized from the corresponding phosphine according to a known method described in Organic Letters 2001, Vol. 3, No. 26, 4295-4298.

The phosphine represented by the formula (E) or the phosphonium salt represented by the formula (F) can also be used, for example, as a ligand in a coupling reaction described in Metal-Catalyzed Cross-Coupling Reactions Second, Completely Revised and Enlarged Edition Volume 1,2 (de Meijere Armin, Diederich Francois ed., 2004, published by Wiley-VCH). Specific examples of the coupling reaction include the Stille coupling, the Heck coupling, the Hiyama coupling, the Sonogashira coupling, the Kumada coupling and the Buchwald-Hartwig coupling.

<Transition Metal Complex>

A transition metal complex can be produced by contacting a phosphine represented by the formula (E) and a group X transition metal complex. Here, "group X transition metal compound" includes, for example, a nickel compound, a palladium compound, a platinum compound and the like. Preferably, a palladium compound and the like are mentioned. Here, "palladium compound" includes, for example, palladium compounds described in the above-described section of explanation of <Palladium compound>, and the like.

The transition metal complex composed of a palladium compound and the above-described phosphine compound or phosphine represented by the formula (E) can be produced according to known methods described, for example, in Vol. 5 Jikken Kagaku Koza (The Chemical Society of Japan ed., published by Maruzen K.K.) 21 Organic transition metal complex•supermolecule complex, p. 308-327 (9.2 Organic palladium complex) and the like.

<Reaction Step>

The production method of the present invention comprises a step of mixing a compound represented by the formula (A) and a compound represented by the formula (B) in the presence of a base, a palladium compound, at least one phosphine compound selected from the group consisting of a phosphine represented by the formula (C) and a phosphonium salt represented by the formula (D) and an aprotic organic solvent, and an aromatic compound is generated by reacting a compound represented by the formula (A) and a compound represented by the formula (B). The mixing order of them is not particularly restricted, and for example, a palladium compound, the above-described phosphine compound, a base, a compound represented by the formula (A), a compound represented by the formula (B) and an aprotic organic solvent may be mixed simultaneously. It may also be permissible that a base, a compound represented by the formula (A), a compound represented by the formula (B) and an aprotic organic solvent are mixed, then, the resultant mixture, an aprotic organic solvent, a palladium compound and the above-described phosphine compound are mixed. Further, it may also be permissible that the above-described phosphine compound and a palladium compound are previously contacted to obtain a transition metal complex, then, a base, a compound represented by the formula (A), a compound represented by the formula (B) and an aprotic organic solvent are mixed to obtain a mixture, and this mixture is mixed with the above-described transition metal complex.

An aromatic compound represented by the following formula (G-1) is obtained by reacting a compound (A-1) and a compound (B-1).

  (G-1)

An aromatic compound represented by the following formula (G-2) is obtained by reacting a compound (A-1) and a compound (B-2).

Ar₁—Ar₂—Ar₁  (G-2)

An aromatic compound represented by the following formula (G-3) is obtained by reacting a compound (A-2) and a compound (B-1).

Ar₂—Ar₁—Ar₂  (G-3)

An aromatic compound having a repeating structural unit represented by the following formula (G-4) is obtained by reacting a compound (A-2) and a compound (B-2) (wherein, Ar¹ and Ar² represent the same meaning as described above).

  (G-4)

The reaction temperature is usually in the range of 0° C. to 180° C., preferably in the range of 30° C. to 100° C. The reaction time is usually in the range of 1 hour to 96 hours, preferably in the range of 3 hours to 48 hours.

After completion of the reaction, a reaction mixture containing an aromatic compound is obtained. The resultant aromatic compound can be isolated by a purification treatment such as chromatographic fractionation and the like. When the aromatic compound is an aromatic compound having a repeating unit represented by the above-described formula (G-4), for example, the targeted aromatic compound can be deposited by a method of mixing the reaction mixture and a poor solvent, and the aromatic compound can be isolated by a usual separation means such as filtration and the like. For removing impurities such as palladium and the like, the reaction mixture may be washed with an acidic solution such as hydrochloric acid and the like before isolation of the targeted aromatic compound.

EXAMPLES

The present invention will be illustrated further in detail by examples below.

When the resultant aromatic compound is an aromatic compound represented by the above-described formulae (G-1) to (G-3), the yield was obtained by purifying by silica gel column chromatography. When the resultant aromatic compound is an aromatic compound having a repeating unit represented by the above-described formula (G-4), analysis was performed by gel permeation chromatography (hereinafter, abbreviated as GPC) (analysis conditions are as described below), and the polystyrene-equivalent weight-average molecular weight (Mw) and the polystyrene-equivalent number-average molecular weight (Mn) were calculated from the analysis results.

<Analysis Condition of GPC>

GPC measurement apparatus: CTO-20A (column oven manufactured by Shimadzu Corp.), SPD-20A (detector manufactured by Shimadzu Corp.)

Column: PLgel 10 μm MIXED-B 300×7.5 mm (manufactured by Polymer Laboratories Ltd.)

Column temperature: 40° C.

Mobile phase: tetrahydrofuran

Flow rate: 2 mL/min

Detection: UV detection (wavelength: 228 nm)

Example 1

Under a nitrogen atmosphere, into a glass reaction vessel equipped with a cooling apparatus were added 5.98 mmol of a boronate composed of 9,9-di-n-octylfluorene-2,7-diboronic acid and pinacol, 6.00 mmol of bis(4-bromophenyl)[4-(methylpropyl)phenyl]amine, 20 ml of a 20 wt % tetraethylammonium hydroxide aqueous solution and 110 mL of toluene at room temperature. The resultant mixture was heated at a bath temperature of 100° C. while stirring. To the mixture were added 3 μmol of bis(di-tert-butyl(4-tert-butylphenyl)phosphine)dichloropalladium(II) and 12 ml of toluene. The resultant mixture was heated at a bath temperature of 100° C. while stirring and reacted for 4 hours, to obtain a reaction mixture containing an aromatic compound composed of the following repeating structural unit. The molecular weight of the resultant aromatic compound was analyzed by GPC, to find a molecular weight (Mw) of $5.0 \times 10^5$.

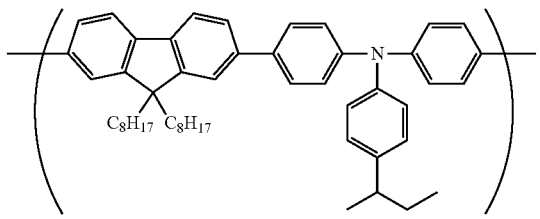

Example 2

An aromatic compound was obtained in the same manner as in Example 1 excepting that bis(di-tert-butyl(4-methylphenyl)phosphine)dichloropalladium(II) was used instead of bis(di-tert-butyl(4-tert-butylphenyl)phosphine)dichloropalladium(II) in Example 1. The resultant aromatic compound had a molecular weight (Mw) of $4.5 \times 10^5$.

Example 3

An aromatic compound was obtained in the same manner as in Example 1 excepting that bis(di-tert-butyl(2-naphthyl)phosphine)dichloropalladium(II) was used instead of bis(di-tert-butyl(4-tert-butylphenyl)phosphine)dichloropalladium(II) in Example 1. The resultant aromatic compound had a molecular weight (Mw) of $4.3 \times 10^5$.

Example 4

An aromatic compound was obtained in the same manner as in Example 1 excepting that bis(di-tert-butyl(4-fluorophenyl)phosphine)dichloropalladium(II) was used instead of bis(di-tert-butyl(4-tert-butylphenyl)phosphine)dichloropalladium(II) in Example 1. The resultant aromatic compound had a molecular weight (Mw) of $3.0 \times 10^5$.

Example 5

An aromatic compound was obtained in the same manner as in Example 1 excepting that bis(di-tert-butyl(4-trifluoromethoxyphenyl)phosphine)dichloropalladium(II) was used instead of bis(di-tert-butyl(4-tert-butylphenyl)phosphine)dichloropalladium(II) in Example 1. The resultant aromatic compound had a molecular weight (Mw) of $3.1 \times 10^5$.

Example 6

An aromatic compound was obtained in the same manner as in Example 1 excepting that bis(di-tert-butyl(2-methoxyphenyl)phosphine)dichloropalladium(II) was used instead of bis(di-tert-butyl(4-tert-butylphenyl)phosphine)dichloropalladium(II) in Example 1. The resultant aromatic compound had a molecular weight (Mw) of $7.4 \times 10^4$.

Example 7

An aromatic compound was obtained in the same manner as in Example 1 excepting that bis(dicyclohexyl(2-methoxyphenyl)phosphine)dichloropalladium(II) was used instead of bis(di-tert-butyl(4-tert-butylphenyl)phosphine)dichloropalladium(II) in Example 1. The resultant aromatic compound had a molecular weight (Mw) of $1.5 \times 10^5$.

The structural formulae of the phosphine compounds used in Examples 1 to 7 and the molecular weights (Mw) of the resultant aromatic compounds are shown in Table 1 described below.

TABLE 1

| Example | Structural formula of phosphine compound | Molecular weight (Mw) of aromatic compound |
|---|---|---|
| 1 | tBu–C6H4–P(tBu)2 | $5.0 \times 10^5$ |
| 2 | Me–C6H4–P(tBu)2 | $4.5 \times 10^5$ |
| 3 | 2-naphthyl–P(tBu)2 | $4.3 \times 10^5$ |
| 4 | F–C6H4–P(tBu)2 | $3.0 \times 10^5$ |
| 5 | OCF3–C6H4–P(tBu)2 | $3.1 \times 10^5$ |

TABLE 1-continued

| Example | Structural formula of phosphine compound | Molecular weight (Mw) of aromatic compound |
|---|---|---|
| 6 | | $7.4 \times 10^4$ |
| 7 | | $1.5 \times 10^5$ |

Example 8

Under a nitrogen atmosphere, into a glass reaction vessel equipped with a cooling apparatus were added 5.99 mmol of a boronate composed of 9,9-di-n-octylfluorene-2,7-diboronic acid and pinacol, 6.00 mmol of bis(4-bromophenyl)[4-(methylpropyl)phenyl]amine, 20 ml of a 20 wt % tetraethylammonium hydroxide aqueous solution and 110 mL of toluene at room temperature. The resultant mixture was heated at a bath temperature of 100° C. while stirring. To the mixture were added 3 μmol of bis(dicyclohexyl(4-tert-butylphenyl)phosphine)dichloropalladium(II) and 12 ml of toluene. The resultant mixture was heated at a bath temperature of 100° C. while stirring and reacted for 4 hours, to obtain a reaction mixture containing an aromatic compound composed of the following repeating structural unit. The molecular weight of the resultant aromatic compound was analyzed by GPC, to find a molecular weight (Mw) of $2.2 \times 10^5$.

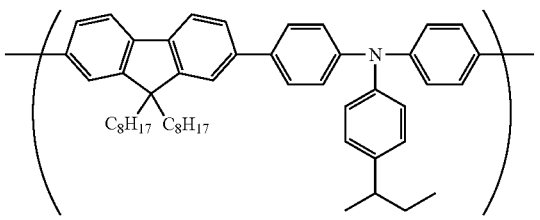

The structural formula of the phosphine compound used in Example 8 and the molecular weight (Mw) of the resultant aromatic compound are shown in Table 2 described below.

TABLE 2

| Example | Structural formula of phosphine compound | Molecular weight (Mw) of aromatic compound |
|---|---|---|
| 8 | tBu | $2.2 \times 10^5$ |

Example 9

Under a nitrogen atmosphere, into a glass reaction vessel equipped with a cooling apparatus were added 5.97 mmol of a boronate composed of 9,9-di-n-octylfluorene-2,7-diboronic acid and pinacol, 6.00 mmol of bis(4-bromophenyl)[4-(methylpropyl)phenyl]amine, 20 ml of a 20 wt % tetraethylammonium hydroxide aqueous solution and 110 mL of toluene at room temperature. The resultant mixture was heated at a bath temperature of 100° C. while stirring. To the mixture were added 3 μmol of bis(di-tert-butyl(3,5-di-(tert-butyl)phenyl)phosphine)dichloropalladium(II) and 12 ml of toluene. The resultant mixture was reacted at a bath temperature of 100° C. for 3 hours while stirring, to obtain a reaction mixture containing an aromatic compound composed of the following repeating structural unit. The molecular weight of the resultant aromatic compound was analyzed by GPC, to find a molecular weight (Mw) of $3.2 \times 10^5$.

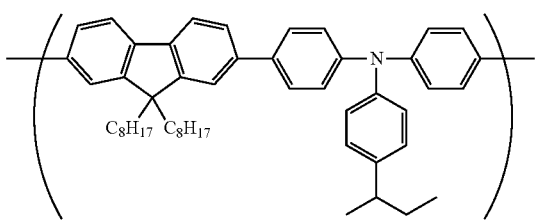

Example 10

A mixture containing an aromatic compound was obtained in the same manner as in Example 9 excepting that bis(di-tert-butyl(3,5-diethylphenyl)phosphine)dichloropalladium(II) was used instead of bis(di-tert-butyl(3,5-di-(tert-butyl)phenyl)phosphine)dichloropalladium(II) in Example 9. The resultant aromatic compound had a molecular weight (Mw) of $2.3 \times 10^5$.

Example 11

A mixture containing an aromatic compound was obtained in the same manner as in Example 9 excepting that bis(di-(tert-butyl)((1,1':3',1''-terphenyl)-5'-yl)phosphine)dichloropalladium(II) was used instead of bis(di-tert-butyl(3,5-di-(tert-butyl)phenyl)phosphine)dichloropalladium(II) in Example 9. The resultant aromatic compound had a molecular weight (Mw) of $2.3 \times 10^5$.

Example 12

A mixture containing an aromatic compound was obtained in the same manner as in Example 9 excepting that bis(di-tert-butyl(3,5-dimethoxyphenyl)phosphine)dichloropalladium(II) was used instead of bis(di-tert-butyl(3,5-di-(tert-butyl)phenyl)phosphine)dichloropalladium(II) in Example 9. The resultant aromatic compound had a molecular weight (Mw) of $2.6 \times 10^5$.

Example 13

A mixture containing an aromatic compound was obtained in the same manner as in Example 9 excepting that bis(di-tert-butyl(3,5-dimethylphenyl)phosphine)dichloropalladium(II) was used instead of bis(di-tert-butyl(3,5-di-(tert-butyl)phenyl)phosphine)dichloropalladium(II) in Example 9. The resultant aromatic compound had a molecular weight (Mw) of $2.8 \times 10^5$.

The structural formulae of the phosphine compounds used in Examples 9 to 13 and the molecular weights (Mw) of the resultant aromatic compounds are shown in Table 3 described below.

TABLE 3

| Example | Structural formula of phosphine compound | Molecular weight (Mw) of aromatic compound |
|---|---|---|
| 9 | tBu, tBu (structure) | $3.2 \times 10^5$ |
| 10 | Et, Et (structure) | $2.3 \times 10^5$ |
| 11 | Ph, Ph (structure) | $2.3 \times 10^5$ |
| 12 | MeO, OMe (structure) | $2.6 \times 10^5$ |
| 13 | Me, Me (structure) | $2.8 \times 10^5$ |

Example 14

A mixture containing an aromatic compound was obtained by conducting the reaction for 2 hours in the same manner as in Example 9 excepting that bis(di-tert-butyl(3-(tert-butyl)phenyl)phosphine)dichloropalladium(II) was used instead of bis(di-tert-butyl(3,5-di-(tert-butyl)phenyl)phosphine)dichloropalladium(II) in Example 9. The resultant aromatic compound had a molecular weight (Mw) of $2.7 \times 10^5$.

Example 15

A mixture containing an aromatic compound was obtained by conducting the reaction for 4 hours in the same manner as in Example 9 excepting that bis(di-tert-butyl(4-(methoxy)phenyl)phosphine)dichloropalladium(II) was used instead of bis(di-tert-butyl(3,5-di-(tert-butyl)phenyl)phosphine)dichloropalladium(II) in Example 9. The resultant aromatic compound had a molecular weight (Mw) of $2.6 \times 10^5$.

Example 16

A mixture containing an aromatic compound was obtained by conducting the reaction for 4 hours in the same manner as in Example 9 excepting that bis(di-tert-butyl(4-(tert-butyl)phenyl)phosphine)dichloropalladium(II) was used instead of bis(di-tert-butyl(3,5-di-(tert-butyl)phenyl)phosphine)dichloropalladium(II) in Example 9. The resultant aromatic compound had a molecular weight (Mw) of $2.5 \times 10^5$.

Example 17

A mixture containing an aromatic compound was obtained by conducting the reaction for 3 hours in the same manner as in Example 9 excepting that bis(di-tert-butyl(2-(methoxy)phenyl)phosphine)dichloropalladium(II) was used instead of bis(di-tert-butyl(3,5-di-(tert-butyl)phenyl)phosphine)dichloropalladium(II) in Example 9. The resultant aromatic compound had a molecular weight (Mw) of $6.0 \times 10^4$.

The structural formulae of the phosphine compounds used in Examples 14 to 17 and the molecular weights (Mw) of the resultant aromatic compounds are shown in Table 4 described below.

TABLE 4

| Example | Structural formula of phosphine compound | Molecular weight (Mw) of aromatic compound |
|---|---|---|
| 14 | (phenyl with tBu at meta, P(tBu)$_2$) | $2.7 \times 10^5$ |
| 15 | (4-OMe-phenyl, P(tBu)$_2$) | $2.6 \times 10^5$ |
| 16 | (4-tBu-phenyl, P(tBu)$_2$) | $2.5 \times 10^5$ |
| 17 | (2-OMe-phenyl, P(tBu)$_2$) | $6.0 \times 10^4$ |

Example 18

A mixture containing an aromatic compound was obtained by conducting the reaction for 6 hours in the same manner as in Example 9 excepting that bis(dicyclohexyl(3,5-di-(tert-butyl)phenyl)phosphine)dichloropalladium(II) was used instead of bis(di-tert-butyl(3,5-di-(tert-butyl)phenyl)phosphine)dichloropalladium(II) in Example 9. The resultant aromatic compound had a molecular weight (Mw) of $1.0 \times 10^5$.

Example 19

A mixture containing an aromatic compound was obtained by conducting the reaction for 4 hours in the same manner as in Example 9 excepting that bis(dicyclohexyl(4-(methoxy)phenyl)phosphine)dichloropalladium(II) was used instead of bis(di-tert-butyl(3,5-di-(tert-butyl)phenyl)phosphine)dichloropalladium(II) in Example 9. The resultant aromatic compound had a molecular weight (Mw) of $1.5 \times 10^5$.

Example 20

A mixture containing an aromatic compound was obtained by conducting the reaction for 4 hours in the same manner as in Example 9 excepting that bis(dicyclohexyl(3,4,5-tri-(methoxy)phenyl)phosphine)dichloropalladium(II) was used instead of bis(di-tert-butyl(3,5-di-(tert-butyl)phenyl)phosphine)dichloropalladium(II) in Example 9. The resultant aromatic compound had a molecular weight (Mw) of $1.1 \times 10^5$.

The structural formulae of the phosphine compounds used in Examples 18 to 20 and the molecular weights (Mw) of the resultant aromatic compounds are shown in Table 5 described below.

TABLE 5

| Example | Structural formula of phosphine compound | Molecular weight (Mw) of aromatic compound |
|---|---|---|
| 17 | (3,5-di-tBu-phenyl, P(Cy)$_2$) | $1.0 \times 10^5$ |
| 18 | (4-OMe-phenyl, P(Cy)$_2$) | $1.5 \times 10^5$ |
| 19 | (3,4,5-tri-OMe-phenyl, P(Cy)$_2$) | $1.1 \times 10^5$ |

Example 21

A mixture containing an aromatic compound was obtained by conducting the reaction for 3 hours in the same manner as in Example 9 excepting that 1.5 μmol of tris(dibenzylideneacetone)dipalladium(0) and 6 μmol of 3,5-di-(tert-butyl)phenyl)phosphonium tetrafluoroborate were used instead of bis(di-tert-butyl(3,5-di-(tert-butyl)phenyl)phosphine)dichloropalladium(II) in Example 9. The resultant aromatic compound had a molecular weight (Mw) of $3.4 \times 10^5$.

Comparative Example 1

A mixture containing an aromatic compound was obtained by conducting the reaction for 6 hours in the same manner as in Example 9 excepting that 1.5 μmol of tris (dibenzylideneacetone)dipalladium(0) and 6 μmol of tri-tert-butylphosphonium tetrafluoroborate were used instead of bis(di-tert-butyl(3,5-di-(tert-butyl)phenyl)phosphine)dichloropalladium(II) in Example 9. The resultant aromatic compound had a molecular weight (Mw) of 2.8×10⁴.

Example 22

A mixture containing an aromatic compound was obtained by conducting the reaction for 5 hours in the same manner as in Example 9 excepting that 3 μmol of palladium acetate and μmol of 3,5-di-(tert-butyl)phenyl)phosphonium tetrafluoroborate were used instead of bis(di-tert-butyl(3,5-di-(tert-butyl)phenyl)phosphine)dichloropalladium(II) in Example 9. The resultant aromatic compound had a molecular weight (Mw) of 3.2×10⁵.

Comparative Example 2

A mixture containing an aromatic compound was obtained by conducting the reaction for 6 hours in the same manner as in Example 9 excepting that 1.5 μmol of tris (dibenzylideneacetone)dipalladium(0) and 6 μmol of 2-dicyclohexylphosphino-2',6'-dimethoxybiphenyl were used instead of bis(di-tert-butyl(3,5-di-(tert-butyl)phenyl)phosphine)dichloropalladium(II) in Example 9. The resultant aromatic compound had a molecular weight (Mw) of 1.2×10⁴.

The structural formulae of the phosphine compounds used in Examples 21 to 22 and Comparative Examples 1 and 2 and the molecular weights (Mw) of the resultant aromatic compounds are shown in Table 5 described below.

TABLE 6

| Example | Palladium compound | Structural formula of phosphine compound | Molecular weight (Mw) of aromatic compound |
|---|---|---|---|
| 21 | Pd₂(dba)₃ | tBu / tBu / PH⁺ / BF₄⁻ structure | 3.4 × 10⁵ |
| Comparative Example 1 | Pd₂(dba)₃ | PH⁺ / BF₄⁻ structure | 2.8 × 10⁴ |
| 22 | Pd(OAc)₂ | tBu / tBu / PH⁺ / BF₄⁻ structure | 3.2 × 10⁵ |

TABLE 6-continued

| Example | Palladium compound | Structural formula of phosphine compound | Molecular weight (Mw) of aromatic compound |
|---|---|---|---|
| Comparative Example 2 | Pd(OAc)₂ | MeO / OMe biphenyl dicyclohexylphosphine | 1.2 × 10⁴ |

Example 23

Under a nitrogen atmosphere, into a glass reaction vessel equipped with a cooling apparatus were added 5.97 mmol of a boronate composed of benzene-1,4-diboronic acid and pinacol, 6.00 mmol of 2,7-dibromo-9,9-di-n-dodecylfluorene, 20 ml of a 20 wt % tetraethylammonium hydroxide aqueous solution and 110 mL of toluene at room temperature. The resultant mixture was heated at a bath temperature of 100° C. while stirring. To the mixture were added 3 μmol of bis(di-tert-butyl(3,5-di-(tert-butyl)phenyl)phosphine)dichloropalladium(II) and 12 ml of toluene. The resultant mixture was reacted for 8 hours at a bath temperature of 100° C. while stirring, to obtain a reaction mixture containing an aromatic compound composed of the following repeating structural unit. The molecular weight of the resultant aromatic compound was analyzed by GPC, to find a molecular weight (Mw) of 3.5×10⁵.

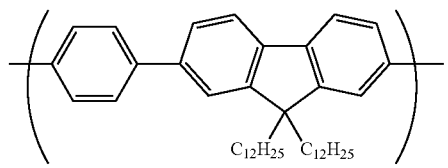

Example 24

Under a nitrogen atmosphere, into a glass reaction vessel equipped with a cooling apparatus were added 6.00 mmol of a boronate composed of benzene-1,4-diboronic acid and pinacol, 4.50 mmol of 2,7-dibromo-9,9-di-n-octylfluorene, 1.50 mmol of 4,7-dibromo-2,1,3-benzothiadiazole, 20 ml of a 20 wt % tetraethylammonium hydroxide aqueous solution and 110 mL of toluene at room temperature. The resultant mixture was heated at a bath temperature of 100° C. while stirring. To the mixture were added 3 μmol of bis(di-tert-butyl(3,5-di-(tert-butyl)phenyl)phosphine)dichloropalladium(II) and 12 ml of toluene. The resultant mixture was reacted for 5 hours at a bath temperature of 100° C. while stirring, to obtain a reaction mixture containing an aromatic compound composed of the following repeating structural unit. The molecular weight of the resultant aromatic compound was analyzed by GPC, to find a molecular weight (Mw) of 2.3×10⁵.

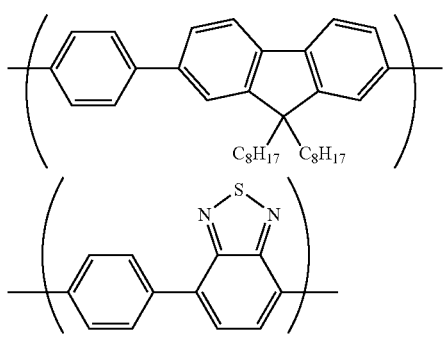

Example 25

Under a nitrogen atmosphere, into a glass reaction vessel equipped with a cooling apparatus were added 5.98 mmol of a boronate composed of 9,9-di-n-octylfluorene-2,7-diboronic acid and 1,3-propanediol, 6.00 mmol of 2,7-dibromo-9,9-di-n-dodecylfluorene, 1.2 mmol of Aliquat (registered trademark) 336 (manufactured by Sigma-Aldrich), 12 ml of a sodium carbonate aqueous solution having a concentration of 3 mol/L and 110 mL of toluene at room temperature. The resultant mixture was heated at a bath temperature of 100° C. while stirring. To the mixture were added 3 μmol of bis(di-tert-butyl(3,5-di-(tert-butyl)phenyl)phosphine)dichloropalladium(II) and 12 ml of toluene. The resultant mixture was reacted for 2 hours at a bath temperature of 100° C. while stirring, to obtain a reaction mixture containing an aromatic compound composed of the following repeating structural unit. The molecular weight of the resultant aromatic compound was analyzed by GPC, to find a molecular weight (Mw) of $2.3 \times 10^5$.

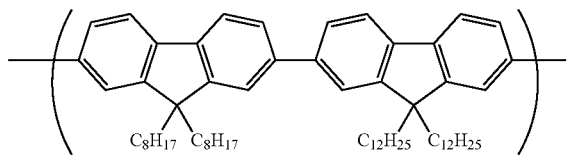

Synthesis Example 1

Synthesis Method of Catalyst Used in Examples 1 and 16

Under a nitrogen atmosphere, into a reaction vessel equipped with a dropping funnel were added 5.5 mmol of 1-bromo-4-tert-butylbenzene (bromide compound) and 20 mL of diethyl ether. The resultant solution was cooled down to −10° C., then, 3.4 ml of n-butyllithium (1.65 M/hexane solution) was dropped. The resultant mixture was stirred at the same temperature for 2 hours, then, a solution obtained by dissolving 5.5 mmol of di-tert-butylchlorophosphine in 13 ml of diethyl ether was dropped at −10° C. The resultant mixture was stirred at room temperature for 3 hours. The resultant reaction mixture was concentrated, to obtain a mixture containing di-tert-butyl(tert-butylphenyl)phosphine.

Under a nitrogen atmosphere, into the reaction vessel were added the above-described mixture containing di-tert-butyl(tert-butylphenyl)phosphine, 0.5 g of dichlorobis(acetonitrile)palladium(II) and 30 mL of ethanol. The resultant mixture was stirred at room temperature for 24 hours. A solid deposited in the resultant reaction mixture was isolated by filtration, and washed with 12 ml of ethanol three times. The resultant solid was dried under reduced pressure at 50° C. for 3 hours, to obtain 0.54 g of bis(di-tert-butyl(4-tert-butylphenyl)phosphine)dichloropalladium(II) in the form of pale yellow solid.

$^1$H-NMR (δ: ppm, CDCl$_3$ solvent, TMS basis): 7.8 (m, 2H), 7.3 (m, 2H), 1.6 (m, 18H), 1.3 (s, 9H)

$^{31}$P-NMR (δ: ppm, CDCl$_3$ solvent): 52.0

Synthesis Examples 2 to 7

Synthesis Method of Catalyst Used in Examples 2 to 6 and 15, 17

The targeted palladium chloride complexes were synthesized by conducting an experiment in the same manner as in Example 26 excepting that bromide compounds corresponding to the phosphine compounds used in Examples 2 to 6 and 15 to 17 were used as a raw material. $^1$H and $^{31}$P-NMR of the resultant complexes are shown in Table 7.

TABLE 7

| Synthesis Example | Structural formula of phosphine compound | $^1$H and $^{31}$P-NMR data |
|---|---|---|
| 2 | Me-C6H4-P(tBu)2 | $^1$H-NMR (δ: ppm, CDCl$_3$ solvent, TMS basis): 7.8 (m, 2H), 7.2 (m, 2H), 2.3 (s, 3H), 1.6 (m, 18H) $^{31}$P-NMR (δ: ppm, CDCl$_3$ solvent, TMS basis): 53.0 |
| 3 | Naphthyl-P(tBu)2 | $^1$H-NMR (δ: ppm, CDCl$_3$ solvent, TMS basis): 8.4 (m, 1H), 8.0 (m, 1H), 7.8 (m, 3H), 7.5 (m, 2H), 1.7 (m, 18H) $^{31}$P-NMR (δ: ppm, CDCl$_3$ solvent, TMS basis): 52.0 |
| 4 | F-C6H4-P(tBu)2 | $^1$H-NMR (δ: ppm, CDCl$_3$ solvent, TMS basis): 7.8 (m, 2H), 7.0 (m, 2H), 1.6 (m, 18H) $^{31}$P-NMR (δ: ppm, CDCl$_3$ solvent, TMS basis): 53.0 |

TABLE 7-continued

| Synthesis Example | Structural formula of phosphine compound | $^1$H and $^{31}$P-NMR data |
|---|---|---|
| 5 | 4-(OCF$_3$)-C$_6$H$_4$-P(tBu)$_2$ | $^1$H-NMR (δ: ppm, CDCl$_3$ solvent, TMS basis): 7.9 (m, 2H), 7.2 (m, 2H), 1.6 (m, 18H) $^{31}$P-NMR (δ: ppm, CDCl$_3$ solvent, TMS basis): 53.4 |
| 6 | 2-(OMe)-C$_6$H$_4$-P(tBu)$_2$ | $^1$H-NMR (δ: ppm, CDCl$_3$ solvent, TMS basis): 7.8 (m, 1H), 7.3 (m, 1H), 6.9 (m, 2H), 3.9 (s, 3H), 1.6 (m, 18H) $^{31}$P-NMR (δ: ppm, CDCl$_3$ solvent, TMS basis): 38.7 |
| 7 | 4-(OMe)-C$_6$H$_4$-P(tBu)$_2$ | $^1$H-NMR (δ: ppm, CDCl$_3$ solvent, TMS basis): 7.8 (m, 2H), 6.9 (m, 2H), 3.8 (s, 3H), 1.6 (m, 18H) $^{31}$P-NMR (δ: ppm, CDCl$_3$ solvent, TMS basis): 51.9 |

Synthesis Example 8

Synthesis Method of Catalyst of Example 7

Under a nitrogen atmosphere, into a reaction vessel equipped with a dropping funnel were added 4.3 mmol of 2-bromoanisole (bromide compound) and 15 mL of diethyl ether. The resultant solution was cooled down to −10° C., then, 2.6 mL of n-butyllithium (1.65 M/hexane solution) was dropped. The resultant mixture was stirred at the same temperature for 3 hours, then, a solution obtained by dissolving 4.3 mmol of chlorodicyclohexylphosphine in 13 ml of diethyl ether was dropped at −10° C. The resultant mixture was stirred at room temperature for 3 hours. The resultant reaction mixture was concentrated, to obtain a mixture containing dicyclohexyl(2-methoxyphenyl)phosphine.

Under a nitrogen atmosphere, into the reaction vessel were added the above-described mixture obtaining dicyclohexyl(2-methoxyphenyl)phosphine, 0.4 g of dichlorobis(acetonitrile)palladium(II) and 30 mL of ethanol. The resultant mixture was stirred at room temperature for 24 hours. A solid deposited in the resultant reaction mixture was isolated by filtration, and washed with 12 ml of ethanol three times. The resultant solid was dried under reduced pressure at 50° C. for 3 hours, to obtain 0.74 g of bis(dicyclohexyl(2-methoxyphenyl)phosphine)dichloropalladium(II) in the form of pale yellow solid.

$^1$H-NMR (δ: ppm, CDCl$_3$ solvent, TMS basis): 7.5 (m, 1H), 7.4 (m, 1H), 7.0 (m, 1H), 3.9 (s, 3H), 2.6 (m, 2H), 2.1 (m, 2H), 1.1-1.9 (m, 18H)

$^{31}$P-NMR (δ: ppm, CDCl$_3$ solvent): 23.0

Synthesis Example 9, Synthesis Example 10, Example 26, Example 27

Synthesis Method of Catalyst of Examples 8 and 18 to 20

The targeted palladium chloride complexes were synthesized by conducting an experiment in the same manner as in Example 33 excepting that bromide compounds corresponding to the phosphine compounds used in Examples 8 and 18 to 20 were used as a raw material. $^1$H and $^{31}$P-NMR of the resultant complexes are shown in Table 8.

TABLE 8

| Synthesis Example | Structural formula of phosphine compound | $^1$H and $^{31}$P-NMR data |
|---|---|---|
| 9 | 4-(tBu)-C$_6$H$_4$-P(Cy)$_2$ | $^1$H-NMR (δ: ppm, CDCl$_3$ solvent, TMS basis): 7.5 (m, 2H), 7.4 (m, 2H), 2.6 (m, 2H), 2.1 (m, 2H), 1.6-1.9 (m, 8H) $^{31}$P-NMR (δ: ppm, CDCl$_3$ solvent, TMS basis): 27.0 |
| Example 26 | 3,5-(tBu)$_2$-C$_6$H$_3$-P(Cy)$_2$ | $^1$H-NMR (δ: ppm, CDCl$_3$ solvent, TMS basis): 7.5 (m, 2H), 7.4 (s, 1H), 2.6 (m, 2H), 2.1 (m, 2H), 1.6-1.9 (m, 8H) $^{31}$P-NMR (δ: ppm, CDCl$_3$ solvent, TMS basis): 29.6 |
| Synthesis Example 10 | 4-(OMe)-C$_6$H$_4$-P(Cy)$_2$ | $^1$H-NMR (δ: ppm, CDCl$_3$ solvent, TMS basis): 7.5 (m, 2H), 6.9 (m, 2H), 3.8 (s, 3H), 2.4 (m, 2H), 2.2 (m, 2H), 1.6-1.9 (m, 8H), 1.6 (s, 3H), 1.2-1.9 (m, 18H) $^{31}$P-NMR (δ: ppm, CDCl$_3$ solvent, TMS basis): 50.3 |
| Example 27 | 2,4,6-(OMe)$_3$-C$_6$H$_2$-P(Cy)$_2$ | $^1$H-NMR (δ: ppm, CDCl$_3$ solvent, TMS basis): 6.9 (m, 2H), 3.90 (s, 3H), 3.88 (s, 6H), 2.6 (m, 2H), 2.1 (m, 2H), 1.6-1.9 (m, 8H), 1.1-1.9 (m, 10H) $^{31}$P-NMR (δ: ppm, CDCl$_3$ solvent, TMS basis): 31.4 |

Example 28

Synthesis Method of Catalyst of Example 9

Under a nitrogen atmosphere, into a reaction vessel equipped with a dropping funnel were added 5.5 mmol of 1-bromo-3,5-di-tert-butylbenzene (bromide compound) and 20 mL of tetrahydrofuran. The resultant solution was cooled down to −70° C., then, 3.4 ml of n-butyllithium (1.65 M/hexane solution) was dropped. The resultant mixture was stirred at the same temperature for 1 hour, then, a solution obtained by dissolving 5.5 mmol of di-tert-butylchlorophosphine in 13 ml of tetrahydrofuran was dropped at −70° C. The resultant mixture was stirred at room temperature for 4 hours. The resultant reaction mixture was concentrated, to obtain a mixture containing di-tert-butyl(3,5-di-(tert-butyl)phenyl)phosphine.

Under a nitrogen atmosphere, into the reaction vessel were added the above-described mixture containing di-tert-butyl(3,5-di-(tert-butyl)phenyl)phosphine, 0.6 g of dichlorobis(acetonitrile)palladium(II) and 40 mL of ethanol. The resultant mixture was stirred at room temperature for 24 hours. A solid deposited in the resultant reaction mixture was isolated by filtration, and washed with 12 ml of ethanol three times. The resultant solid was dried under reduced pressure at 50° C. for 3 hours, to obtain 1.23 g of bis(di-tert-butyl (3,5-di-(tert-butyl)phenyl)phosphine)dichloropalladium(II) in the form of pale yellow solid.

$^{1}$H-NMR (δ: ppm, CDCl$_3$ solvent, TMS basis): 7.7 (m, 2H), 7.3 (s, 1H), 1.6 (m, 18H), 1.3 (s, 18H)

$^{31}$P-NMR (δ: ppm, CDCl$_3$ solvent): 55.0

Examples 29 to 32, Synthesis Example 11

Synthesis Method of Catalyst of Examples 10 to 14

The targeted palladium chloride complexes were synthesized by conducting an experiment in the same manner as in Example 38 excepting that bromide compounds corresponding to the phosphine compounds used in Examples 10 to 14 were used as a raw material. $^{1}$H and $^{31}$P-NMR of the resultant complexes are shown in Table 9.

TABLE 9

| Example | Structural formula of phosphine compound | $^{1}$H and $^{31}$P-NMR data |
|---|---|---|
| 29 | Et, Et substituted phenyl phosphine | $^{1}$H-NMR (δ: ppm, CDCl$_3$ solvent, TMS basis): 7.5 (m, 2H), 7.0 (s, 1H), 2.6 (quartet, 2H), 1.6 (m, 18H), 1.2 (t, 3H) $^{31}$P-NMR (δ: ppm, CDCl$_3$ solvent, TMS basis): 53.3 |
| 30 | Ph, Ph substituted phenyl phosphine | $^{1}$H-NMR (δ: ppm, CDCl$_3$ solvent, TMS basis): 8.1 (m, 2H), 7.8 (m, 1H), 7.7 (m, 2H), 7.6 (m, 2H), 7.4 (m, 4H), 7.3 (m, 2H), 1.7 (m, 18H) $^{31}$P-NMR (δ: ppm, CDCl$_3$ solvent, TMS basis): 55.3 |
| 31 | MeO, OMe substituted phenyl phosphine | $^{1}$H-NMR (δ: ppm, CDCl$_3$ solvent, TMS basis): 7.0 (m, 2H), 7.4 (m, 1H), 3.8 (s, 3H), 1.6 (m, 18H) $^{31}$P-NMR (δ: ppm, CDCl$_3$ solvent, TMS basis): 56.0 |
| 32 | Me, Me substituted phenyl phosphine | $^{1}$H-NMR (δ: ppm, CDCl$_3$ solvent, TMS basis): 7.5 (m, 2H), 7.0 (m, 1H), 2.6 (quartet, 2H), 2.3 (s, 3H) $^{31}$P-NMR (δ: ppm, CDCl$_3$ solvent, TMS basis): 52.6 |
| Synthesis Example 11 | tBu substituted phenyl phosphine | $^{1}$H-NMR (δ: ppm, CDCl$_3$ solvent, TMS basis): 8.0 (m, 1H), 7.6 (m, 1H), 7.4 (m, 1H), 7.2 (m, 1H), 1.6 (m, 18H), 1.3 (s, 9H) $^{31}$P-NMR (δ: ppm, CDCl$_3$ solvent, TMS basis): 54.3 |

Example 33

Synthesis Method of 3,5-di-(tert-butyl)phenyl)phosphonium tetrafluoroborate Used in Examples 21 and 22

Under a nitrogen atmosphere, into a reaction vessel equipped with a dropping funnel were added 5.5 mmol of 1-bromo-3,5-di-tert-butylbenzene and 20 mL of tetrahydrofuran. The resultant solution was cooled down to −70° C., then, 3.4 ml of n-butyllithium (1.65M/hexane solution) was dropped. The resultant mixture was stirred at the same temperature for 1 hour, then, a solution obtained by dissolving 5.5 mmol of di-tert-butylchlorophosphine in 13 ml of tetrahydrofuran was dropped at −70° C. The resultant mixture was stirred at room temperature for 4 hours. The resultant reaction mixture was concentrated, to obtain a mixture containing di-tert-butyl(3,5-di-(tert-butyl)phenyl) phosphine.

Under a nitrogen atmosphere, into the reaction vessel were added the above-described mixture containing di-tert-butyl(3,5-di-(tert-butyl)phenyl)phosphine and 10 mL of diethyl ether. At room temperature, 6.6 mmol of tetrafluoroboric acid diethyl ether complex was added and the mixture was stirred vigorously for 30 minutes. The deposited solid was isolated by filtration, and washed with 10 mL of diethyl ether three times. The resultant solid was dried under reduced pressure at 50° C. for 3 hours, to obtain 1.53 g of 3,5-di-(tert-butyl)phenyl)phosphonium tetrafluoroborate in the form of white solid.

$^{1}$H-NMR (δ: ppm, CDCl$_3$ solvent, TMS basis): 7.8 (m, 3H), 7.3 (d, 1H), 1.55 (s, 9H), 1.50 (s, 9H), 1.4 (s, 18H)

$^{31}$P-NMR (δ: ppm, CDCl$_3$ solvent): 42.5

Example 34

Into a glass reaction vessel equipped with a cooling apparatus were added 0.0042 mmol of bis(di-tert-butyl(3,5-di-(tert-butyl)phenyl)phosphine)dichloropalladium(II), 1.5 mmol of 4-bromo-m-xylene, 1.65 mmol of o-tolylboronic acid, 3.0 mmol of potassium phosphate, 6 mL of toluene and 1.5 mL of water. The resultant mixture was stirred with heating at 100° C. for 3 hours. The resultant reaction mixture was cooled down to room temperature, 20 mL of water was added, and the mixture was extracted with 20 mL of diethyl ether twice. The resultant organic layers were mixed, and dried over anhydrous magnesium sulfate, then, filtrated, to obtain a solution. This solution was concentrated, and purified by silica gel column chromatography, to obtain 2,4,2'-trimethylbiphenyl with a yield of 96%.

Examples 35 to 38

Into a glass reaction vessel equipped with a cooling apparatus were added 0.0015 mmol of bis(di-tert-butyl(3,5-di-(tert-butyl)phenyl)phosphine)dichloropalladium(II), 0.3 mmol of trioctylmethylammonium chloride, 1.5 mmol of a compound (1) shown in Table 10, 1.65 mmol of a compound (2) shown in Table 10, 3.0 mmol of sodium carbonate, 6 mL of toluene and 1.5 mL of water. The resultant mixture was stirred with heating at 100° C. for 3 hours. The resultant reaction mixture was cooled down to room temperature, 20 mL of water was added, and the mixture was extracted with 20 mL of diethyl ether twice. The resultant organic layers were mixed, and dried over anhydrous magnesium sulfate, then, filtrated, to obtain a solution containing the targeted compound (3). The yield of the compound (3) was determined by concentrating the resultant solution, and purifying by silica gel column chromatography. The results are shown in Table 10.

0.0030 mmol of 3,5-di-(tert-butyl)phenyl)phosphonium tetrafluoroborate, 0.3 mmol of trioctylmethylammonium chloride, 1.5 mmol of o-tolyl bromide, 1.65 mmol of 2,6-dimethylphenylboronic acid, 3.0 mmol of sodium carbonate, 6 mL of toluene and 1.5 mL of water. The resultant mixture was stirred with heating at 100° C. for 3 hours. The resultant reaction mixture was cooled down to room temperature, 20 mL of water was added, and the mixture was extracted with 20 mL of diethyl ether twice. The resultant organic layers were mixed, and dried over anhydrous magnesium sulfate, then, filtrated, to obtain a solution. This solution was concentrated, and purified by silica gel column chromatography, to obtain 2,4,2'-trimethylbiphenyl with a yield of 91%.

Comparative Example 3

2,4,2'-trimethylbiphenyl was obtained with a yield of 47% in the same manner as in Example 50 excepting that 0.3 mmol of 2-dicyclohexylphosphino-2',6'-dimethoxybiphenyl was used instead of 3,5-di-(tert-butyl)phenyl)phosphonium tetrafluoroborate in Example 50.

Examples 40 to 43

Into a glass reaction vessel equipped with a cooling apparatus were added 0.0075 mmol of bis(di-tert-butyl(3,5-di-(tert-butyl)phenyl)phosphine)dichloropalladium(II), 1.5 mmol of a compound (1) shown in Table 11, 1.65 mmol of

TABLE 10

| Example | Compound (1) | Compound (2) | Compound (3) | Yield (%) |
|---------|--------------|--------------|--------------|-----------|
| 35 | EtO-C(=O)-C6H4-Cl | (HO)2B-C6H4-CH3 | EtO-C(=O)-C6H4-C6H4-CH3 | 67 |
| 36 | 2,6-(OMe)2-C6H3-Br | (HO)2B-C6H4-CH3 | 2,6-(OMe)2-C6H3-C6H4-CH3 | 98 |
| 37 | 2,6-dimethylphenyl-Br | (HO)2B-2-methylphenyl | 2,6-dimethyl-2'-methylbiphenyl | 91 |
| 38 | 2-methylphenyl-Br | (HO)2B-2,6-dimethylphenyl | 2,2',6'-trimethylbiphenyl | 100 |

Example 39

Into a glass reaction vessel equipped with a cooling apparatus were added 0.0015 mmol of palladium acetate, a compound (2) shown in Table 11, 3.0 mmol of potassium phosphate, 6 mL of toluene and 1.5 mL of water. The resultant mixture was stirred with heating at 100° C. for 3 hours. The resultant reaction mixture was cooled down to room temperature, 20 mL of water was added, and the mixture was extracted with 20 mL of diethyl ether twice. The resultant organic layers were mixed, and dried over anhydrous magnesium sulfate, then, filtrated, to obtain a solution containing the targeted compound (3). The yield of the compound (3) was determined by concentrating the resultant solution, and purifying the resultant coarse product by silica gel column chromatography. The results are shown in Table 11.

obtain a solution. This solution was concentrated, and purified by silica gel column chromatography, to obtain 3-(3-thienyl)-pyridine with a yield of 100%.

INDUSTRIAL APPLICABILITY

According to the present invention, an aromatic compound can be produced.

TABLE 11

| Example | Compound (1) | Compound (2) | Compound (3) | Yield (%) |
|---|---|---|---|---|
| 40 | m-tolyl-Br | thiophene-Bpin | m-tolyl-thiophene | 98 |
| 41 | 2-chloropyridine | (HO)₂B-tolyl | 2-(p-tolyl)pyridine | 94 |
| 42 | 3-bromothiophene | (HO)₂B-tolyl | 3-(p-tolyl)thiophene | 95 |
| 43 | 2-bromothiophene | thiophene-Bpin | 2,2'-bithiophene | 89 |

Example 44

Into a glass reaction vessel equipped with a cooling apparatus were added 0.015 mmol of bis(di-tert-butyl(3,5-di-(tert-butyl)phenyl)phosphine)dichloropalladium(II), 1.5 mmol of 3-bromopyridine, 2.25 mmol of 2-thiopheneboronic acid pinacol ester, 3.0 mmol of potassium phosphate, 6 mL of toluene and 1.5 mL of water. The resultant mixture was stirred with heating at 100° C. for 3 hours. The resultant reaction mixture was cooled down to room temperature, 20 mL of water was added, and the mixture was extracted with 20 mL of diethyl ether twice. The resultant organic layers were mixed, and dried over anhydrous magnesium sulfate, then, filtrated, to obtain a solution. This solution was concentrated, and purified by silica gel column chromatography, to obtain 3-(2-thienyl)-pyridine with a yield of 96%.

Example 45

Into a glass reaction vessel equipped with a cooling apparatus were added 0.015 mmol of bis(di-tert-butyl(3,5-di-(tert-butyl)phenyl)phosphine)dichloropalladium(II), 1.5 mmol of 3-bromothiophene, 2.25 mmol of 3-pyridineboronic acid, 3.0 mmol of potassium phosphate and 4 mL of n-butanol. The resultant mixture was stirred with heating at 100° C. for 4 hours. The resultant reaction mixture was cooled down to room temperature, 20 mL of water was added, and the mixture was extracted with 20 mL of diethyl ether twice. The resultant organic layers were mixed, and dried over anhydrous magnesium sulfate, then, filtrated, to

The invention claimed is:

1. A method of producing an aromatic compound, comprising a step of mixing a compound represented by the formula (A):

wherein $X^1$ represents a group represented by the formula (1), (2), (3), (4), (5) or (6):

(1)

(2)

(3)

-continued

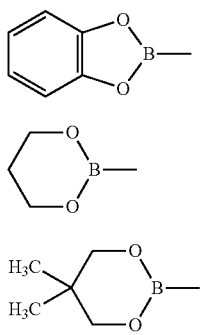

(4)

(5)

(6)

Ar¹ represents a monovalent or divalent aromatic hydrocarbon group having 6 to 36 carbon atoms, and m represents 1 or 2, wherein a carbon atom contained in the aromatic hydrocarbon group can be substituted with a heteroatom or a carbonyl group, and a hydrogen atom contained in the aromatic hydrocarbon group can be substituted with a fluorine atom, an alkyl group, a cycloalkyl group, an alkoxy group, a cycloalkoxy group, an alkylthio group, a cycloalkylthio group, an aryl group, an aryloxy group, an arylthio group, an arylalkyl group, an arylcycloalkyl group, an arylalkenyl group, an arylalkynyl group, a heterocyclic group which can have a substituent, an amino group which can have a substituent, a silyl group which can have a substituent, an acyl group, a group having a carbon atom-nitrogen atom double bond as a partial structure, an acid imide group, an alkoxycarbonyl group, a cycloalkoxycarbonyl group, an aryloxycarbonyl group, a carboxyl group, a cyano group or a nitro group, and a compound represented by the formula (B):

$$Ar^2\text{—}(X^2)_n,$$ (B)

wherein $X^2$ represents a chlorine atom, a bromine atom, an iodine atom, an alkylsulfonyloxy group, a fluorine-substituted alkylsulfonyloxy group or an arylsulfonyloxy group, $Ar^2$ represents a monovalent or divalent aromatic hydrocarbon group having 6 to 36 carbon atoms, and n represents 1 or 2, wherein a carbon atom contained in the aromatic hydrocarbon group can be substituted with a heteroatom or a carbonyl group, and a hydrogen atom contained in the aromatic hydrocarbon group can be substituted with a fluorine atom, an alkyl group, a cycloalkyl group, an alkoxy group, a cycloalkoxy group, an alkylthio group, a cycloalkylthio group, an aryl group, an aryloxy group, an arylthio group, an arylalkyl group, an arylcycloalkyl group, an arylalkenyl group, an arylalkynyl group, a heterocyclic group which can have a substituent, an amino group which can have a substituent, a silyl group which can have a substituent, an acyl group, a group having a carbon atom-nitrogen atom double bond as a partial structure, an acid imide group, an alkoxycarbonyl group, a cycloalkoxycarbonyl group, an aryloxycarbonyl group, a carboxyl group, a cyano group or a nitro group, in the presence of a base, a palladium compound, an aprotic organic solvent, and at least one phosphine compound selected from the group consisting of a phosphine represented by the formula (E):

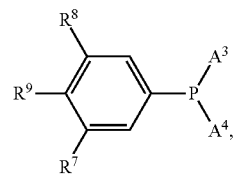

(E)

and a phosphonium salt represented by the formula (F):

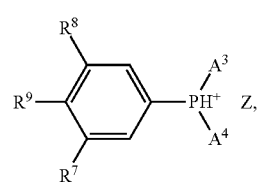

(F)

wherein $A^3$ and $A^4$ each independently represent an alkyl group having 1 to 20 carbon atoms or a saturated alicyclic hydrocarbon group having 6 to 20 carbon atoms, $R^7$ and $R^8$ each independently represent a fluorine atom, an alkyl group having 1 to 20 carbon atoms, a cycloalkyl group having 3 to 20 carbon atoms, an alkoxy group having 1 to 20 carbon atoms, a cycloalkoxy group having 3 to 20 carbon atoms, a fluoroalkoxy group having 1 to 20 carbon atoms, or an aryl group having 6 to 20 carbon atoms, $R^9$ represents a hydrogen atom, and Z represents an anion.

2. The method of producing an aromatic compound according to claim 1, wherein $R^7$ and $R^8$ are each independently a fluorine atom, an alkyl group having 1 to 6 carbon atoms, an alkoxy group having 1 to 6 carbon atoms, a fluoroalkoxy group having 1 to 6 carbon atoms or an aryl group having 6 to 20 carbon atoms.

3. The method of producing an aromatic compound according to claim 1, wherein the aprotic organic solvent is at least one selected from the group consisting of ether solvents, aromatic hydrocarbon solvents and aliphatic hydrocarbon solvents.

4. The method of producing an aromatic compound according to claim 1, wherein the palladium compound is a palladium(0) complex or a palladium(II) complex.

5. A phosphine represented by the formula (E):

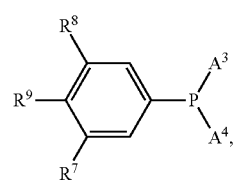

(E)

wherein $A^3$ and $A^4$ each independently represent an alkyl group having 1 to 20 carbon atoms or a saturated alicyclic hydrocarbon group having 6 to 20 carbon atoms, $R^7$ and $R^8$ each independently represent a fluorine atom, an alkyl group having 1 to 20 carbon atoms, a cycloalkyl group having 3 to 20 carbon atoms, an alkoxy group having 1 to 20 carbon atoms, a cycloalkoxy group having 3 to 20 carbon atoms, a fluoroalkoxy group having 1 to 20 carbon atoms or an aryl group having 6 to 20 carbon atoms, and $R^9$ represents a hydrogen atom.

6. The phosphine according to claim 5, wherein $R^7$ and $R^8$ are each independently a fluorine atom, an alkyl group having 1 to 6 carbon atoms, an alkoxy group having 1 to 6 carbon atoms, a fluoroalkoxy group having 1 to 6 carbon atoms or an aryl group having 6 to 20 carbon atoms.

7. A phosphonium salt represented by the formula (F):

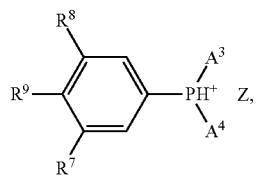

(F)

wherein $A^3$ and $A^4$ each independently represent an alkyl group having 1 to 20 carbon atoms or a saturated alicyclic hydrocarbon group having 6 to 20 carbon atoms, $R^7$ and $R^8$ each independently represent a fluorine atom, an alkyl group having 1 to 20 carbon atoms, a cycloalkyl group having 3 to 20 carbon atoms, an alkoxy group having 1 to 20 carbon atoms, a cycloalkoxy group having 3 to 20 carbon atoms, a fluoroalkoxy group having 1 to 20 carbon atoms or an aryl group having 6 to 20 carbon atoms, and $R^9$ represents a hydrogen atom.

8. The phosphonium salt according to claim 7, wherein $R^7$ and $R^8$ each independently represent a fluorine atom, an alkyl group having 1 to 6 carbon atoms, an alkoxy group having 1 to 6 carbon atoms, a fluoroalkoxy group having 1 to 6 carbon atoms or an aryl group having 6 to 20 carbon atoms.

9. A transition metal complex obtained by contacting the phosphine according to claim 5 and a group X transition metal compound.

* * * * *